(12) United States Patent
Kingsmore et al.

(10) Patent No.: US 8,029,982 B2
(45) Date of Patent: Oct. 4, 2011

(54) BIOMARKERS FOR SEPSIS

(75) Inventors: Stephen F. Kingsmore, Guilford, CT (US); Serguei J. Lejnine, Rocky Hill, CT (US); Mark Driscoll, Wallingford, CT (US); Velizar T. Tchernev, Branford, CT (US)

(73) Assignee: Alere San Diego, Inc., San Diego, CA (US)

( * ) Notice: Subject to any disclaimer, the term of this patent is extended or adjusted under 35 U.S.C. 154(b) by 0 days.

(21) Appl. No.: 12/775,382

(22) Filed: May 6, 2010

(65) Prior Publication Data
US 2010/0304981 A1  Dec. 2, 2010

Related U.S. Application Data

(63) Continuation of application No. 10/759,216, filed on Jan. 20, 2004, now abandoned.

(51) Int. Cl.
*C12Q 1/02* (2006.01)
(52) U.S. Cl. .......................................................... 435/4
(58) Field of Classification Search .................. None
See application file for complete search history.

(56) References Cited

U.S. PATENT DOCUMENTS

| | | | |
|---|---|---|---|
| 4,531,936 A | 7/1985 | Gordon | |
| 5,639,617 A | 6/1997 | Bohuon | |
| 5,710,008 A | 1/1998 | Jackowski | |
| 5,965,375 A | 10/1999 | Valkirs | |
| 6,190,872 B1 | 2/2001 | Slotman | |
| 6,207,395 B1 | 3/2001 | Valkirs et al. | |
| 6,303,321 B1 | 10/2001 | Tracey et al. | |
| 6,503,722 B1 | 1/2003 | Valkirs | |
| 6,673,562 B2 | 1/2004 | Shi | |
| 6,743,595 B1 | 6/2004 | Gosselin et al. | |
| 6,828,110 B2 | 12/2004 | Lee et al. | |
| 6,908,739 B2 | 6/2005 | Buechler et al. | |
| 7,052,858 B2 | 5/2006 | Gray et al. | |
| 7,235,368 B2 | 6/2007 | Bergmann et al. | |
| 7,329,738 B1 | 2/2008 | Lee et al. | |
| 7,374,888 B2 | 5/2008 | Valkirs et al. | |
| 7,393,647 B2 | 7/2008 | Valkirs et al. | |
| 2001/0021511 A1 | 9/2001 | Valkirs et al. | |
| 2002/0127618 A1 | 9/2002 | Gray et al. | |
| 2003/0109420 A1 | 6/2003 | Valkirs et al. | |
| 2004/0097460 A1 | 5/2004 | Ivey et al. | |
| 2004/0121343 A1 | 6/2004 | Buechler et al. | |
| 2004/0203083 A1 | 10/2004 | Buechler et al. | |
| 2004/0253637 A1 | 12/2004 | Buechler et al. | |
| 2005/0148029 A1 | 7/2005 | Buechler et al. | |
| 2005/0164238 A1 | 7/2005 | Valkirs et al. | |
| 2005/0196817 A1 | 9/2005 | Kingsmore et al. | |
| 2007/0092911 A1 | 4/2007 | Buechler et al. | |
| 2007/0172906 A1 | 7/2007 | Valkirs et al. | |
| 2008/0050832 A1 | 2/2008 | Buechler et al. | |
| 2009/0004755 A1 | 1/2009 | Lee et al. | |
| 2010/0240078 A1* | 9/2010 | Lee et al. .................. | 435/7.94 |

FOREIGN PATENT DOCUMENTS

| | | |
|---|---|---|
| WO | WO 98/14582 A1 | 4/1998 |
| WO | WO 03/073099 A1 | 9/2003 |
| WO | WO 2004/043236 A2 | 5/2004 |
| WO | WO 2004/044555 A2 | 5/2004 |
| WO | WO 2004/059293 A2 | 7/2004 |
| WO | WO 2004/044555 A3 | 9/2004 |
| WO | WO 2004/087949 A2 | 10/2004 |
| WO | WO 2004/059293 A3 | 3/2005 |
| WO | WO 2005/033327 A2 | 4/2005 |
| WO | WO 2005/048823 A2 | 6/2005 |
| WO | WO 2004/043236 A3 | 7/2005 |
| WO | WO 2004/087949 A3 | 10/2005 |
| WO | WO 2005/048823 A3 | 11/2005 |
| WO | WO 2005/033327 A3 | 8/2006 |

OTHER PUBLICATIONS

Becker et al. Procalcitonin and the calcitonin gene family of peptides in inflammation, infection, and sepsis: A journey from calcitonin back to its precursors. J. clin. endocrinol. Metab. 2004;89(4): 1512-1525.

Bernard, et al. Efficacy and safety of recombinant human activated protein C for severe sepsis. N Engl J Med. Mar. 8, 2001;344(10):699-709.

Biasucci, L.M. CDC/AHA Workshop on Markers of Inflammation and Cardiovascular Disease.Circulation. 2004;110:e560-e567.

Bone, et al. Definitions for sepsis and organ failure and guidelines for the use of innovative therapies in sepsis. Chest 1992;101:1644-53.

Bossink, et al. Plasma Levels of the Chemokines Monocyte Chemotactic Proteins-1 and -2 Are Elevated in Human Sepsis. Blood 1995;86:3841-3847.

Charpentier, et al. Brain natriuretic peptide: A marker of myocardial dysfunction and prognosis during severe sepsis. Crit Care Med. Mar. 2004;32(3):660-5.

Chinnaiyan, et al. Short Communication Molecular signatures of sepsis: Multiorgan gene expression profiles of systemic inflammation. Am J Pathol. Oct. 2001;159(4):1199-1209.

C-reactive protein. Medline Plus. http:www.nlm.nih.gov/medlineplus/ency/article/003356.htm.

Cruse, et al. Illustrated Dictionary of Immunology, 2nd edition. CRC Press. 2003; 539.

Delogu, et al. Serum neopterin and soluble interleukin-2 receptor for prediction of a shock state in gram-negative sepsis. J Crit Care. Jun. 1995;10(2):64-71.

Doellner, et al. Increased serum concentrations of soluble tumor necrosis factor receptors p55 and p75 in early onset neonatal sepsis. Early Human Development. Oct. 1, 1998;52(3)251-261.

(Continued)

*Primary Examiner* — Nita M Minnifield
*Assistant Examiner* — Brian J Gangle
(74) *Attorney, Agent, or Firm* — Wilson Sonsini Goodrich & Rosati

(57) ABSTRACT

Biomarkers for sepsis and resulting mortality can be detected by assaying blood samples. Changes in the concentration of the biomarkers can be used to indicate sepsis, risk of sepsis, progression of sepsis, remission from sepsis, and risk of mortality. Changes can be evaluated relative to data sets, natural or synthetic or semisynthetic control samples, or patient samples collected at different time points. Some biomarkers' concentrations are elevated during disease and some are depressed. These are termed informative biomarkers. Some biomarkers are diagnostic in combination with others. Individual biomarkers may be weighted when used in combinations. Biomarkers can be assessed in individual, isolated or assays, in parallel assays, or in single-pot assays.

9 Claims, 27 Drawing Sheets

OTHER PUBLICATIONS

Dollner, et al. Inflammatory mediators in umbilical plasma from neonates who develop early-onset sepsis. Biol Neonate. Jul. 2001;80:41-7-2404 PCT/US2004031769.

Dorland's Medical Dictionary. http://www.mercksource.com/pp/us/cns/cns_hl_dorlands_split.jsp?pg=/ppdocs/us/common/dorlands/dorland/seven/000095957.htm. Accessed on Oct. 6, 2008).

Fassbender, et al. Changes in coagulation and fibrinolysis markers in acute ischemic stroke treated with recombinant tissue plasminogen activator. Stroke. Oct. 1999;30(10):2101-4.

FDA 510-k summary K040887. B•R•A•H•M•S Diagnostica. Prepared on Dec. 22, 2004.

Freitag, et al. Plasma Brain Natriuretic Peptide Levels and Blood Pressure Tracking in the Framingham Heart Study. Hypertension. 2003;41:978-983.

Gabay, et al. Interleukin 1 Receptor Antagonist (IL-1Ra) Is an Acute-Phase Protein J. Clin. Invest. 1997; 99(12):2930-2940.

Hausfater, et al. Usefulness of procalcitonin as a marker of systemic infection in emergency department patients: a prospective study. Clin Infect Dis. Apr. 1, 2002;34(7):895-901.

Hotchkiss, et al. The pathophysiology and treatment of sepsis. N Engl J Med. Jan. 9, 2003;348(2):138-50.

Hurst, et al. Use of Plasma Biomarkers at Exacerbation of Chronic Obstructive Pulmonary Disease. Am. J. Respir. Crit. Care Med. 2006;174:867-874.

iHOP (Information Hyperlinked Over Proteins), entry for CRP, downloaded from http://www.ihop-net.org/UniPub/iHOP/gs/92774.html on Jan. 16, 2007.

iHOP (Information Hyperlinked Over Proteins), entry for TNFRSF1A, p. 1, downloaded from http://www.ihop-net.org/UniPub/iHOP/gs/92774.html on Jan. 17, 2007.

Indik, et al. Detection of pulmonary embolism by D-dimer assay, spiral computed tomography, and magnetic resonance imaging. Prog. Cardiovasc. Dis. 2000; 42: 261-272.

Kimura, et al. Plasma concentration of cytokine antagonists in patients with infection following liver resection. British Journal of Surgery. Dec. 1998; 85:1631-1635.

Kinasewitz, et al. Universal changes in biomarkers of coagulation and inflammation occur in patients with severe sepsis, regardless of causative micro-organism. Crit Care. 2004; 8(2): R82-R90.

Lein, et al. Metalloproteinases (MMP-1, MMP-3) and their inhibitors (TIMP) in blood plasma of patients with prostate carcinoma. Urologe A. 1998;37(4): 377-381 (English abstract only).

Liras, et al. Clinical value of an automated granulocyte elastase assay in predicting severity of acute pancreatitis. Rev Esp Enferm Dig. Sep. 1995;87(9):641-52. (In Spanish with English abstract).

Lukacs, et al. Characterization of Chemokine Function in Animal Models of Diseases. Methods. Aug. 1996;10(1):158-65.

Lundblad, et al. Endothelin concentrations in experimental sepsis: profiles of big endothelin and endothelin 1-21 in lethal peritonitis in rats. Eur J Surg. Jan. 1995;161(1):9-16.

Macias, et al. Severe protein C deficiency predicts early death in severe sepsis. Crit Care Med. May 2004;32(5 Suppl):S223-8.

Matsumori, et al. Plasma Levels of the Monocyte Chemotactic and Activating Factor/ Monocyte Chemoattractant Protein-1 are Elevated in Patients with Acute Myocardial Infarction. J. Mol. Cell. Cardiol. 1997;29:419-423.

Mitaka, et al. Endothelin-1 and atrial natriuretic peptide in septic shock. Am Heart J. Aug. 1993;126(2):466-8.

Murdoch, et al. The role of chemokines in sepsis and septic shock. Contrib Microbiol. 2003;10:38-57.

National Institute of Health. Medical Encyclopedia. Http://www.nlm.nih.gov/medlineplus/ency/article/000666.htm.Accessed on Oct. 6, 2008.

Office action issued Mar. 4, 2009 for U.S. Appl. No. 11/690,767.

Office action issued May 29, 2009 for U.S. Appl. No. 11/543,312.

Poeze, et al. An international sepsis survey: a study of doctor's knowledge and perception about sepsis. Critical Care. 2004;8(6):R409-R413.

Reddy, et al. Sepsis-induced immunosuppression: from bad to worse. Immunol Res. 2001;24(3): 273-287.

Siegel, J. P. Assessing the use of activated protein C in the treatment of severe sepsis. N Engl J Med. Sep. 26, 2002;347(13):1030-1034.

Slotwinski, et al. The soluble tumor necrosis factor receptor I is an early predictor of local infective complications after colorectal surgery. J Clin Immunol. Sep. 2002;22(5):289-96.

Standiford, et al. Macrophage inflammatory protein-1 alpha mediates lung leukocyte recruitment, lung capillary leak, and early mortality in murine endotoxemia. J Immunol. Aug. 1, 1995;155(3):1515-24.

Takano, et al. Markers of a hypercoagulable state following acute ischemic stroke. Stroke. Feb. 1992;23(2):194-8.

The Online Medical Dictionary. Http://cancerweb.ncl.ac.uk/cgi-bin/omd?sepsis. Accessed on Oct. 6, 2008.

Traber, D.L. Tumor necrosis factor and endothelins: team players in shock? J Lab Clin Med. Dec. 1994;124(6):746-7.

Triage® BNP Test package insert. Intended Use. p. 1.

Verweij, et al. Full-length von Willebrand factor (vWF) cDNA encodes a highly repetitive protein considerably larger than the mature vWF subunit. EMBO J. Aug. 1986; 5(8): 1839-1847.

Yan, et al. Low levels of protein C are associated with poor outcome in severe sepsis. Chest. Sep. 2001;120(3):915-22.

Zisman, et al. MCP-1 protects mice in lethal endotoxemia. J Clin Invest. Jun. 15, 1997;99(12):2832-6.

* cited by examiner

| GMSTEXPO | | | | |
|---|---|---|---|---|
| | | | Cumulative | Cumulative |
| GMSTEXPO | Frequency | Percent | Frequency | Percent |
| Mixed Gram | 29 | 11.93 | 29 | 11.93 |
| No Bacteria Expo | 85 | 34.98 | 114 | 46.91 |
| Pure Gram Neg | 44 | 18.11 | 158 | 65.02 |
| Pure Gram Pos | 73 | 30.04 | 231 | 95.06 |
| Unconfirm Gram | 12 | 4.94 | 243 | 100 |

FIGURE 2

| QDA Prevalence 0.3 | | | | | |
|---|---|---|---|---|---|
| Statistics | CutOff | Sensitivity | Specificity | PPV | NPV |
| Eot | 7.06 | 0.92 | 0.7 | 0.57 | 0.95 |
| IL-1b | 1.71 | 0.95 | 0.66 | 0.55 | 0.97 |
| MPIF-1 | 4.89 | 0.98 | 0.52 | 0.47 | 0.98 |
| EGF | 8.94 | 0.96 | 0.52 | 0.46 | 0.97 |
| MCP-1 | 8.17 | 0.98 | 0.44 | 0.43 | 0.98 |
| IL-2sRa | 12.55 | 0.94 | 0.46 | 0.43 | 0.94 |
| IL-1ra | 10.28 | 0.96 | 0.45 | 0.43 | 0.97 |
| TNF-R1 | 8.34 | 0.97 | 0.42 | 0.42 | 0.97 |
| IL-6 | 3.19 | 0.98 | 0.41 | 0.42 | 0.97 |
| ProteinC | 13.89 | 0.98 | 0.43 | 0.41 | 0.98 |
| MIF | 10.08 | 0.95 | 0.39 | 0.41 | 0.95 |
| ST2 | 7.54 | 0.97 | 0.38 | 0.4 | 0.97 |
| MIP3b | 7.75 | 0.97 | 0.41 | 0.4 | 0.97 |
| OSM | 7.77 | 0.9 | 0.41 | 0.39 | 0.9 |
| MIP-1a | 7.69 | 0.88 | 0.34 | 0.39 | 0.89 |
| HCC4 | 10.6 | 0.97 | 0.37 | 0.39 | 0.96 |
| ENA-78 | 9.74 | 0.94 | 0.3 | 0.39 | 0.93 |
| PARC | 10.16 | 0.94 | 0.35 | 0.37 | 0.92 |
| MMP9 | 11.09 | 0.89 | 0.29 | 0.37 | 0.88 |
| HVEM | 10.53 | 0.87 | 0.29 | 0.36 | 0.86 |
| P-Selectin | 12.41 | 0.91 | 0.26 | 0.36 | 0.89 |
| Leptin | 8.29 | 0.92 | 0.3 | 0.36 | 0.9 |
| BLC | 5.14 | 0.96 | 0.32 | 0.35 | 0.93 |
| IL-8 | 11.38 | 0.89 | 0.24 | 0.35 | 0.86 |
| GROb | 9.52 | 0.87 | 0.25 | 0.34 | 0.85 |
| MIG | 10.8 | 0.9 | 0.26 | 0.34 | 0.85 |
| MCP-2 | 7.9 | 0.93 | 0.34 | 0.34 | 0.89 |
| IL-15 | 6.33 | 0.88 | 0.26 | 0.34 | 0.83 |
| M-CSF | 9.12 | 0.9 | 0.22 | 0.33 | 0.84 |

| LDA Prevalence 0.3 | | | | | |
|---|---|---|---|---|---|
| Statistics | CutOff | Sensitivity | Specificity | PPV | NPV |
| Eot | 7 | 0.92 | 0.64 | 0.52 | 0.95 |
| IL-1b | 6.31 | 0.95 | 0.6 | 0.51 | 0.97 |
| MPIF-1 | 8.44 | 0.98 | 0.51 | 0.46 | 0.99 |
| EGF | 8.94 | 0.96 | 0.52 | 0.46 | 0.97 |
| TNF-R1 | 11.14 | 0.94 | 0.47 | 0.44 | 0.95 |
| IL-1ra | 10.38 | 0.96 | 0.44 | 0.43 | 0.96 |
| ST2 | 7.45 | 0.98 | 0.42 | 0.42 | 0.98 |
| MIF | 10.19 | 0.94 | 0.44 | 0.42 | 0.95 |
| MCP-1 | 10.73 | 0.97 | 0.42 | 0.42 | 0.97 |
| IL-6 | 9.77 | 0.97 | 0.45 | 0.42 | 0.97 |
| IL-2sRa | 12.54 | 0.93 | 0.4 | 0.41 | 0.94 |
| ProteinC | 13.18 | 0.96 | 0.38 | 0.4 | 0.96 |
| MIP3b | 7.65 | 0.95 | 0.38 | 0.4 | 0.94 |
| HCC4 | 10.92 | 0.96 | 0.4 | 0.4 | 0.96 |
| ENA-78 | 9.94 | 0.94 | 0.38 | 0.4 | 0.94 |
| PARC | 11.93 | 0.92 | 0.39 | 0.39 | 0.92 |
| OSM | 7.73 | 0.91 | 0.4 | 0.39 | 0.91 |
| MIP-1a | 7.61 | 0.9 | 0.32 | 0.37 | 0.9 |
| P-Selectin | 12.59 | 0.91 | 0.33 | 0.37 | 0.9 |
| GROb | 9.16 | 0.91 | 0.3 | 0.36 | 0.87 |
| MMP9 | 11.13 | 0.89 | 0.31 | 0.36 | 0.88 |
| Leptin | 9.32 | 0.9 | 0.29 | 0.36 | 0.88 |
| HVEM | 7.87 | 0.93 | 0.31 | 0.36 | 0.91 |
| BLC | 6.95 | 0.91 | 0.29 | 0.35 | 0.88 |
| MIG | 9.79 | 0.9 | 0.25 | 0.34 | 0.85 |
| MCP-2 | 7.39 | 0.86 | 0.29 | 0.34 | 0.83 |
| IL-8 | 11.76 | 0.87 | 0.26 | 0.34 | 0.83 |
| IL-15 | 6.25 | 0.86 | 0.26 | 0.33 | 0.81 |
| M-CSF | 9.96 | | | | |

FIGURE 3

FIGURE 4. Analyte aliases.

Array I analytes

| | Analyte | Full Name | Aliases |
|---|---|---|---|
| 1 | ANG | Angiogenin | |
| 2 | BLC | B-lymphocyte chemoattractant | CXCL13, SCYB13, BCA-1 |
| 3 | EGF | Epidermal growth factor | beta urogastrone, HMGF |
| 4 | ENA-78 | Epithelial cell-derived neutrophil-activating peptide | CXCL5, SCYB5 |
| 5 | Eot | Eotaxin | CCL11 |
| 6 | Eot-2 | Eotaxin-2 | CCL24 |
| 7 | Fas | Fibroblast-Associated | TNFRSF6, CD95, Apo-1 |
| 8 | FGF-7 | Fibroblast growth factor-7 | KGF-2 |
| 9 | FGF-9 | Fibroblast growth factor-9 | GAF, HBGF-9 |
| 10 | GDNF | Glial cell line derived neurotrophic factor | ATF, B49-derived neurotrophic factor |
| 11 | GM-CSF | Granulocyte macrophage colony stimulating factor | CSF-a, E-CSF |
| 12 | IL-1ra | Interleukin 1 receptor antagonist | IL-1F3, ILS, IL-1 inhibitor |
| 13 | IL-2 sRα | Interleukin 2 soluble receptor alpha | IL-2 Ra, CD25, IL-2R, p55 |
| 14 | IL-3 | Interleukin 3 | BPA, E-CSF |
| 15 | IL-4 | Interleukin 4 | BCDF, BCGF |
| 16 | IL-5 | Interleukin 5 | BCDFm, BCDFm |
| 17 | IL-6 | Interleukin 6 | 26-kDa protein, BSF-2 |
| 18 | IL-7 | Interleukin 7 | LP-1; Lpo-1, Pre-B cell growth factor |
| 19 | IL-8 | Interleukin 8 | CXCL8, chemotaxin, GCP |
| 20 | IL-13 | Interleukin 13 | NC30, p600 |
| 21 | IL-15 | Interleukin 15 | Interleukin T (IL-T) |
| 22 | MCP-2 | Monocyte chemotactic protein 2 | CCL8, HC14, SCYA8 |
| 23 | MCP-3 | Monocyte chemotactic protein 3 | CCL7, MARC (mouse), FIC (mouse) |
| 24 | MIP-1α | Macrophage inflammatory protein 1 alpha | CCL3, GOS19, LD78 alpha |
| 25 | MPIF | Myeloid progenitor inhibitory factor 1 | |
| 26 | OSM | Oncostatin M | OM; OncoM; ONC |
| 27 | PLGF | Placental growth factor | |

FIGURE 4 (Cont'd.)

Array 2 analytes

| | Analyte | Full Name | Aliases |
|---|---|---|---|
| 1 | AR | Amphiregulin | AMR; AREG, CRDGF, KAF, SDGF |
| 2 | BDNF | Brain-derived neurotrophic factor | |
| 3 | Flt-3 Lig | fms-like tyrosine kinase-3 ligand | Flt-3/Flk-2 ligand, FL, Stk-1 ligand |
| 4 | GCP-2 | Granulocyte chemotactic protein 2 | CXCL6, CKA-3 (mouse), LIX (mouse, rat) |
| 5 | HCC4 | Hemofiltrate CC chemokine 4 | CCL16, ILINCK, interleukin 10 inducible chemokine, NCC4 |
| 6 | I-309 | I-309 | CCL1, p500 (mouse), SCYA1 |
| 7 | IL-1α | Interleukin 1 alpha | IL-1F1, BAF; BCAF, EP |
| 8 | IL-1β | Interleukin 1 beta | IL-1F2, catabolin, H1 |
| 9 | IL-2 | Interleukin 2 | BF, costimulator |
| 10 | IL-17 | Interleukin 17 | CTLA-8 |
| 11 | MCP-1 | Monocyte chemotactic protein 1 | CCL2, GDCF, HCII |
| 12 | M-CSF | Macrophage colony stimulating factor | CSA, CSF-1 |
| 13 | MIG | Monokine induced by interferon gamma | CXCL9, SCYB9 |
| 14 | MIP-1β | Macrophage inflammatory protein 1 beta | CCL4, ACT-2, G26 |
| 15 | MIP-1α | Macrophage inflammatory protein 1 delta | LKN-1, CCL15, CC-2, HCC-2, MIP-5, NCC-3, SCYA15 |
| 16 | NT-3 | Neurotrophin 3 | HDNF, NGF-2 |
| 17 | NT-4 | Neurotrophin 4 | NT-4/5, NT-5 |
| 18 | PARC | Pulmonary and activation-regulated chemokine | CCL18, AMAC-1, Dctactin |
| 19 | RANTES | Regulated upon activation, normal T expressed and presumably secreted | CCL5, EoCP-1, SCYA5 |
| 20 | SCF | Stem cell factor | c-kit Ligand (KL), HLGF-1 |
| 21 | Sgp130 | Soluble glycoprotein 130 | CD130, IL6ST |
| 22 | TARC | Thymus and activation regulated chemokine | CCL17, SCYA17 |
| 23 | TNF-RI | Tumor necrosis factor receptor I | TNFRSF1A, CD120a, p55, p55TNFR |
| 24 | TNF-α | Tumor necrosis factor alpha | TNFSF2, cachectin, cytotoxin |
| 25 | TNF-β | Tumor necrosis factor beta | TNFSF1, differentiation-inducing factor, cytotoxin |

FIGURE 4 (Cont'd.)
Array 2 analytes

| | Analyte | Full Name | Aliases |
|---|---|---|---|
| 26 | VEGF | Vascular endothelial growth factor | VEGF-A, folliculo-stellate cell-derived growth factor, GD-VEGF, vascular endothelial cell proliferation factor, VPF, VAS |

FIGURE 4 (Cont'd.)
Array 3 analytes

| | Analyte | Full Name | Aliases |
|---|---|---|---|
| 1 | BTC | Betacellulin | BCCIP |
| 2 | DR6 | Death receptor 6 | TNFRSF21 |
| 3 | Fas Lig | Fibroblast-associated ligand | TNFSF6, CD178, Apo-1 ligand; APT1L, CD95L |
| 4 | FGF acid | Fibroblast growth factor acidic | FGF-1, a-ECGF, astroglial growth factor I |
| 5 | Fractalkine | Fractalkine | FKN; FK, CX3CL1, ABCD-3, CX3C membrane-anchored chemokine, NTN, SCYD1 |
| 6 | GRO-β | Growth related oncogene beta | CXCL2, CINC-2a (rat), GRO-2 |
| 7 | HCC-1 | Hemofiltrate CC chemokine 1 | CCL14, Chb-1, chemokine CC-1/CC-3 |
| 8 | HGF | Hepatocyte growth factor | HPTA, Scatter Factor (SF) |
| 9 | HVEM | Herpes virus entry mediator | TNFRSF14, ATAR, HveA |
| 10 | ICAM-3 | Intercellular adhesion molecule 3 | CD50 |
| 11 | IGFBP-2 | Insulin-like growth factor binding protein 2 | |
| 12 | IL-2 Rγ | Interleukin 2 receptor gamma | CD132, common gamma chain |
| 13 | IL-5 Rα | Interleukin 5 receptor alpha | CD125, CDw125 |
| 14 | IL-9 | Interleukin 9 | MCGF, MEA (mouse) |
| 15 | Leptin | Leptin | Obesity (OB) |
| 16 | L-Selectin | Leukocyte selectin | CD62L, LAM-1, LECAM-1 |
| 17 | MCP-4 | Monocyte chemotactic protein 4 | CCL13, CKb-10, NCC-1 |
| 18 | MIP-3β | Macrophage inflammatory protein 3 beta | CCL19, CKb-11, Exodus-3 |
| 19 | MMP-7 (total) | Matrix metalloproteinase 7 | Matrilysin, Pump-1 |
| 20 | MMP-9 | Matrix metalloproteinase 9 | 2 kDa gelatinase, gelatinase B |
| 21 | PECAM-1 | Platelet endothelial cell adhesion molecule-1 | CD31 |
| 22 | RANK | Receptor activator of NF-kappa-B | TNFRSF11A, ODAR, ODFR |
| 23 | SCF R | Stem cell factor receptor | CD117, c-kit |
| 24 | TIMP-1 | Tissue inhibitors of metalloproteinases 1 | |
| 25 | TRAIL R4 | TNF-related apoptosis-inducing ligand receptor 4 | TNFRSF10D, DcR2, TRUNDD |
| 26 | VEGF-R2 | Vascular endothelial growth factor receptor 2 | KDR, Flk-1 (mouse) |
| 27 | ST2 | Interleukin 1 receptor 4 | IL-1R4, DER4 (mouse) |

FIGURE 4 (Cont'd.)

Array 4 analytes

| | Analyte | Full Name | Aliases |
|---|---|---|---|
| 1 | ALCAM | Activated leukocyte cell adhesion molecule | CD166, BEN (chicken), DM-GRASP (chicken) |
| 2 | β-NGF | beta-nerve growth factor | |
| 3 | CD27 | Cluster of Differentiation 27 | TNFRSF7, S152, T14 |
| 4 | CTACK | Cutaneous T-cell attracting chemokine | CCL27, ALP, Eskin |
| 5 | CD30 | Cluster of Differentiation 30 | TNFRSF8, Ber-H2 antigen, Ki-1 antigen |
| 6 | Eot-3 | Eotaxin-3 | CCL26, MIP-4a, SCYA26 |
| 7 | FGF-2 | Fibroblast growth factor-2 | FGF-basic, astroglial GF 2, cartilage-derived growth factor |
| 8 | FGF-4 | Fibroblast growth factor-4 | Hst |
| 9 | Follistatin | Follistatin | FS, activin binding protein, FSP |
| 10 | GRO-γ | Growth related oncogene gamma | CXCL3, CINC-2b(rat), GRO-3 |
| 11 | ICAM-1 | Intercellular adhesion molecule 1 | CD54 |
| 12 | IFN-γ | Interferon gamma | Antigen-Induced Interferon |
| 13 | IFN-ω | Interferon omega | Interferon alpha II (IFN-aII) |
| 14 | IGF-1R | Insulin-like growth factor I receptor | CD221 |
| 15 | IGFBP-1 | Insulin-like growth factor binding protein 1 | 34kD IGFBP, alpha pregnancy-associated endometrial globulin |
| 16 | IGFBP-3 | Insulin-like growth factor binding protein 3 | Binding Protein 29, BP-53 |
| 17 | IGFBP-4 | Insulin-like growth factor binding protein 4 | Colon Cancer Cell Growth Inhibitor, HT29-IGFBP |
| 18 | IGF-II | Insulin-like growth factor II | growth-promoting activity for vascular endothelial cells, MSA |
| 19 | IL-1 sRI | Interleukin 1 soluble receptor I | CD121a, IL-1RI |
| 20 | IL-1 sRII | Interleukin 1 soluble receptor II | CDw121b, IL-1R2 |
| 21 | IL-10 Rβ | Interleukin 10 receptor beta | CRF2-4, CRFB-4 |
| 22 | IL-16 | Interleukin 16 | LCF |
| 23 | IL-2 Rβ | Interleukin 2 receptor beta | CD122, p75 |
| 24 | I-TAC | Interferon gamma-inducible T cell alpha chemoattractant | CXCL11, B-R1, H174 |
| 25 | Lptn | Lymphotactin | XCL1, Ltn, ATAC, SCM-1a |
| 26 | LT βR | lymphotoxin-beta receptor | TNFRSF3, TNFRIII, TNFRrp |

FIGURE 4 (Cont'd.)
Array 4 analytes

|    | Analyte    | Full Name                                    | Aliases                                                                  |
|----|------------|----------------------------------------------|--------------------------------------------------------------------------|
| 27 | M-CSF R    | Macrophage colony stimulating factor receptor | CD115, c-fms, CSFR1                                                      |
| 28 | MIP-3α     | Macrophage inflammatory protein 3 alpha      | CCL20, Exodus-1, LARC                                                    |
| 29 | MMP-10     | Matrix metalloproteinase 10                  | Stromelysin 2, Transin 2                                                 |
| 30 | PDGF Rα    | Platelet-derived growth factor receptor alpha | CD140a                                                                   |
| 31 | PF4        | Stromal cell-derived factor beta             | CXCL4, CTAP-3, Endothelial cell growth inhibitor, Platelet factor 4      |
| 32 | sVAP-1     | Soluble Vascular Adhesion Protein-1          |                                                                          |
| 33 | TGF-α      | Transforming growth factor alpha             | Sarcoma Growth Factor                                                    |
| 34 | TIMP-2     | Tissue inhibitors of metalloproteinases 2    |                                                                          |
| 35 | TRAIL R1   | TNF-related apoptosis-inducing ligand receptor 1 | TNFRSF10A, DR4                                                       |
| 36 | VE-cadherin | Vascular Endothelial Cadherin               | VECAD, CD144, 7B4, Cadherin-5                                            |
| 37 | VEGF-D     | Vascular endothelial growth factor-D         | c-fos-induced growth factor (FIGF)                                       |

FIGURE 4 (Cont'd.)

Array 5 analytes

| | Analyte | Full Name | Aliases |
|---|---|---|---|
| 1 | 4-1BB | 4-1BB | TNFRSF9, CDw137, ILA CD137 |
| 2 | ACE-2 | Angiotensin I converting enzyme-2 | |
| 3 | AFP | Alpha fetoprotein | HPAFP |
| 4 | AgRP | Agouti-related protein | ART |
| 5 | CD141 | Thrombomodulin/CD141 | Fetomodulin, TM |
| 6 | CD40 | CD40 | TNFRSF5, Bp50 |
| 7 | CNTF Rα | Ciliary neurotrophic factor receptor alpha | |
| 8 | CRP | C-reactive protein | |
| 9 | D-Dimer | D-Dimer | |
| 10 | E-Selectin | E-selectin | CD62E, ELAM-1, LECAM-2 |
| 11 | FGF-21 | Fibroblast growth factor 21 | |
| 12 | HCG | Human chorionic gonadotrophin | |
| 13 | IGFBP-6 | Insulin-like Growth Factor Binding Protein 6 | |
| 14 | IL-12 (p40) | Interleukin 12 p40 | |
| 15 | IL-18 | Interleukin 18 | IGIF, IL-1gamma |
| 16 | LIF Rα | Leukemia inhibitory factor souble receptor alpha | gp190 |
| 17 | MIF | Macrophage migration inhibitory factor | Glycosylation Inhibition Factor (GIF) |
| 18 | MMP-8 (total) | Matrix Metalloproteinase-8 | Collagenase 2, Neutrophil Collagenase |
| 19 | NAP-2 | Neutrophil Activating Peptide 2 | CXCL7 |
| 20 | Neutrophil elastase | Neutrophil elastase | |
| 21 | PAI-II | plasminogen activator inhibitor-II | PAI-2 |
| 22 | Prolactin | Prolactin | PRL, Lactotropin, LTH |
| 23 | Protein C | Human Protein C | |
| 24 | Protein S | Human Protein S | |
| 25 | P-Selectin | P-Selectin | CD62P, GMP-140, PADGEM |
| 26 | TSH | Thyroid stimulating hormone | |

FIGURE 5A
SlideMapName Pr te mics1.4

| Analyte Name | Variabl | RunDay | DX ||||| Pr > F |
|---|---|---|---|---|---|---|---|---|---|
| | | | Diff (1-2) || Sepsis || Sick || |
| | | | Mean | Std Dev | Mean | Std Dev | Mean | Std Dev | |
| BLC | visit1 | d1 | 0.63 | 1.17 | 7.32 | 1.26 | 6.69 | 0.62 | 0.00041 |
| | | d2 | 0.82 | 1.18 | 6.95 | 1.24 | 6.13 | 0.86 | 0.000004 |
| | | d3 | 0.65 | 1.2 | 7.7 | 1.27 | 7.05 | 0.84 | 0.000404 |
| EGF | visit1 | d1 | -2.2 | 1.3 | 7.89 | 1.34 | 10.09 | 1.1 | <.000001 |
| | | d2 | -2.27 | 1.31 | 7.4 | 1.23 | 9.67 | 1.63 | <.000001 |
| | | d3 | -2.31 | 1.24 | 8.13 | 1.27 | 10.44 | 1.1 | <.000001 |
| ENA-78 | visit1 | d1 | -1.35 | 1.67 | 9.36 | 1.74 | 10.7 | 1.36 | <.000001 |
| | | d2 | -1.87 | 1.59 | 8.81 | 1.64 | 10.68 | 1.35 | <.000001 |
| | | d3 | -1.63 | 1.66 | 9.29 | 1.75 | 10.92 | 1.24 | <.000001 |
| Eot | visit1 | d1 | -0.56 | 0.53 | 6.78 | 0.47 | 7.34 | 0.71 | <.000001 |
| | | d2 | -0.87 | 0.62 | 6.32 | 0.54 | 7.19 | 0.9 | <.000001 |
| | | d3 | -0.82 | 0.56 | 6.79 | 0.55 | 7.61 | 0.62 | <.000001 |
| GDNF | visit1 | d1 | -0.23 | 0.39 | 7.34 | 0.39 | 7.56 | 0.43 | 0.000152 |
| | | d2 | -0.26 | 0.46 | 6.84 | 0.44 | 7.1 | 0.53 | 0.000245 |
| IL-15 | visit1 | d2 | 0.51 | 0.72 | 6.15 | 0.72 | 5.63 | 0.7 | 0.000002 |
| | | d3 | 0.24 | 0.64 | 6.6 | 0.66 | 6.36 | 0.5 | 0.011704 |
| IL-1ra | visit1 | d1 | 4.14 | 2.43 | 12.6 | 2.62 | 8.47 | 1.39 | <.000001 |
| | | d2 | 4.27 | 2.59 | 12.25 | 2.75 | 7.97 | 1.76 | <.000001 |
| | | d3 | 3.88 | 2.44 | 12.52 | 2.65 | 8.65 | 1.33 | <.000001 |
| IL-2sRa | visit1 | d1 | 1.9 | 1.21 | 13.49 | 1.2 | 11.59 | 1.26 | <.000001 |
| | | d2 | 1.84 | 1.35 | 13.32 | 1.36 | 11.49 | 1.29 | <.000001 |
| | | d3 | 1.75 | 1.26 | 13.62 | 1.26 | 11.87 | 1.24 | <.000001 |
| IL-6 | visit1 | d1 | 3.61 | 2.53 | 11.7 | 2.73 | 8.09 | 1.4 | <.000001 |
| | | d2 | 3.94 | 2.65 | 11.4 | 2.85 | 7.47 | 1.59 | <.000001 |
| | | d3 | 3.49 | 3.4 | 11.79 | 2.58 | 8.31 | 1.42 | <.000001 |
| IL-8 | visit1 | d1 | -0.84 | 1.64 | 11.33 | 1.68 | 12.17 | 1.47 | 0.00087 |
| | | d2 | -1.02 | 1.66 | 11.08 | 1.9 | 12.1 | 1.56 | 0.000222 |
| | | d3 | -0.89 | 1.8 | 11.55 | 1.88 | 12.44 | 1.44 | 0.001392 |
| MCP-2 | visit1 | d1 | 1.01 | 1.68 | 8.18 | 1.82 | 7.16 | 0.8 | 0.00009 |
| | | d2 | 1 | 1.6 | 7.31 | 1.73 | 6.31 | 0.5 | 0.000033 |
| | | d3 | 0.67 | 1.62 | 8.06 | 1.74 | 7.4 | 0.91 | 0.007912 |
| MIP-1a | visit1 | d1 | -0.44 | 0.64 | 7.68 | 0.61 | 8.12 | 0.73 | 0.000009 |
| | | d2 | -0.58 | 0.63 | 7.11 | 0.59 | 7.68 | 0.77 | <.000001 |
| | | d3 | -0.41 | 0.58 | 7.34 | 0.59 | 7.75 | 0.54 | 0.000005 |

FIGURE 5A (Cont'd.)
SlideMapName Pr te mics1.4

| Analyte Name | Variabl | RunDay | DX | | | | | | Pr > F |
|---|---|---|---|---|---|---|---|---|---|
| | | | Diff (1-2) | | Sepsis | | Sick | | |
| | | | Mean | Std Dev | Mean | Std Dev | Mean | Std Dev | |
| MPIF-1 | visit1 | d1 | 2.12 | 1.28 | 9.72 | 1.37 | 7.6 | 0.78 | <.000001 |
| | | d2 | 2.17 | 1.32 | 9.18 | 1.4 | 7.02 | 0.9 | <.000001 |
| | | d3 | 1.96 | 1.25 | 9.62 | 1.33 | 7.66 | 0.87 | <.000001 |
| OSM | visit1 | d1 | -0.66 | 0.64 | 7.8 | 0.65 | 8.46 | 0.63 | <.000001 |
| | | d2 | -0.56 | 0.66 | 7.41 | 0.57 | 7.98 | 0.95 | <.000001 |

FIGURE 5B
SlideMapName Pr teomics2.3

| Analyt Name | Variable | RunDay | DX | | | | | | Pr > F |
|---|---|---|---|---|---|---|---|---|---|
| | | | Diff (1-2) | | Sepsis | | Sick | | |
| | | | Mean | Std Dev | Mean | Std Dev | Mean | Std Dev | |
| AR | visit1 | d1 | 0.25 | 0.59 | 7.36 | 0.62 | 7.11 | 0.46 | 0.005993 |
| | | d3 | 0.36 | 0.58 | 7.17 | 0.59 | 6.81 | 0.53 | 0.000114 |
| HCC4 | visit1 | d1 | -1.46 | 1.6 | 13.68 | 1.74 | 12.14 | 0.77 | <.000001 |
| | | d2 | -1.65 | 1.67 | 9.93 | 1.77 | 11.57 | 1.11 | <.000001 |
| | | d3 | -1.56 | 1.6 | 10.07 | 1.76 | 11.63 | 0.99 | <.000001 |
| IL-1a | visit1 | d1 | -0.24 | 0.56 | 6.68 | 0.57 | 6.92 | 0.51 | 0.003906 |
| | | d3 | 0.24 | 0.59 | 6.7 | 0.62 | 6.45 | 0.52 | 0.010592 |
| IL-1b | visit1 | d1 | -1.56 | 0.81 | 5.77 | 0.71 | 7.34 | 1.14 | <.000001 |
| | | d2 | -1.37 | 0.92 | 5.25 | 0.84 | 6.62 | 1.19 | <.000001 |
| | | d3 | -1.12 | 0.76 | 6.37 | 0.61 | 7.5 | 1.08 | <.000001 |
| M-CSF | visit1 | d1 | 0.36 | 0.83 | 10.37 | 0.87 | 10.01 | 0.66 | 0.00439 |
| | | d2 | 0.29 | 0.87 | 10.09 | 0.91 | 9.79 | 0.66 | 0.024124 |
| MCP-1 | visit1 | d1 | 2.14 | 1.57 | 12.43 | 1.69 | 10.29 | 0.84 | <.000001 |
| | | d2 | 1.97 | 1.78 | 11.75 | 1.95 | 9.78 | 0.73 | <.000001 |
| | | d3 | 2.87 | 1.64 | 11.86 | 1.83 | 9 | 0.9 | <.000001 |
| MIG | visit1 | d1 | 1.44 | 2.24 | 10.6 | 2.39 | 9.16 | 1.41 | 0.009023 |
| | | d2 | 1.39 | 2.27 | 10.47 | 2.41 | 9.08 | 1.56 | 0.000054 |
| | | d3 | 1.91 | 2.2 | 11.12 | 2.36 | 9.2 | 1.64 | <.000001 |
| PARC | visit1 | d1 | 1.1 | 0.97 | 12.62 | 0.98 | 11.52 | 0.92 | <.000001 |
| | | d2 | 0.78 | 0.97 | 12.84 | 0.97 | 12.06 | 0.94 | <.000001 |
| | | d3 | 0.87 | 1.01 | 11.93 | 1.06 | 11.06 | 0.86 | <.000001 |
| Rantes | visit1 | d2 | -0.17 | 0.51 | 15.63 | 0.56 | 15.8 | 0.18 | 0.027227 |
| | | d3 | 0.31 | 0.42 | 15.35 | 0.47 | 15.04 | 0.2 | 0.000005 |
| SCF | visit1 | d2 | 0.23 | 0.74 | 7.23 | 0.74 | 7 | 0.7 | 0.033637 |
| | | d3 | 0.4 | 0.6 | 7.27 | 0.64 | 6.88 | 0.46 | 0.000057 |
| TNF-R1 | visit1 | d1 | 1.79 | 1.02 | 12.46 | 1.07 | 10.68 | 0.79 | <.000001 |
| | | d2 | 1.68 | 1.18 | 12.36 | 1.2 | 10.68 | 1.07 | <.000001 |
| | | d3 | 1.47 | 1.26 | 11.23 | 1.27 | 9.76 | 1.26 | <.000001 |
| TNF-a | visit1 | d2 | 0.37 | 0.64 | 7.56 | 0.66 | 7.19 | 0.56 | 0.000122 |
| | | d3 | 0.25 | 0.62 | 8.08 | 0.6 | 7.84 | 0.66 | 0.013088 |
| VEGF | visit1 | d1 | 0.23 | 0.59 | 8.47 | 0.62 | 8.24 | 0.49 | 0.010748 |
| | | d2 | 0.22 | 0.56 | 7.92 | 0.62 | 7.7 | 0.39 | 0.012154 |
| sgp130 | visit1 | d1 | -0.15 | 0.47 | 12.52 | 0.48 | 12.67 | 0.41 | 0.039511 |
| | | d3 | -0.16 | 0.44 | 13.11 | 0.45 | 13.28 | 0.44 | 0.023336 |

FIGURE 5C
SlideMapNam  Pr teomics3.4

| | | | DX ||||||  |
|---|---|---|---|---|---|---|---|---|---|
| | | | Diff (1-2) || Sepsis || Sick || |
| | | | Mean | Std Dev | Mean | Std Dev | M an | Std Dev | Pr > F |
| Analyte Name | Variabl | RunDay | | | | | | | |
| DR6 | visit1 | d1 | 0.39 | 0.52 | 9.47 | 0.56 | 9.08 | 0.33 | 0.000001 |
| | | d2 | 0.25 | 0.58 | 9.01 | 0.61 | 8.76 | 0.43 | 0.004055 |
| GROb | visit1 | d2 | -0.57 | 1.1 | 8.38 | 1.17 | 8.95 | 0.76 | 0.000664 |
| | | d3 | -0.74 | 1.19 | 9.42 | 1.26 | 10.17 | 0.84 | 0.000202 |
| HCC1 | visit1 | d1 | 0.33 | 0.52 | 11.27 | 0.52 | 10.95 | 0.49 | 0.000045 |
| | | d2 | 0.61 | 0.48 | 11.08 | 0.51 | 10.47 | 0.31 | <.000001 |
| | | d3 | 0.23 | 0.3 | 11.16 | 0.31 | 10.93 | 0.28 | 0.000002 |
| HVEM | visit1 | d1 | 0.87 | 0.77 | 8.45 | 0.84 | 7.58 | 0.43 | <.000001 |
| | | d2 | 0.6 | 0.86 | 8.09 | 0.95 | 7.49 | 0.51 | 0.000009 |
| | | d3 | 0.36 | 0.84 | 8.19 | 0.87 | 7.83 | 0.69 | 0.007135 |
| IGFBP2 | visit1 | d1 | 0.58 | 0.75 | 13.95 | 0.79 | 13.37 | 0.52 | <.000001 |
| | | d2 | 1 | 0.7 | 13.66 | 0.72 | 12.65 | 0.63 | <.000001 |
| | | d3 | 0.15 | 0.47 | 13.61 | 0.45 | 13.46 | 0.52 | 0.033055 |
| Leptin | visit1 | d1 | -1.41 | 2.56 | 9.64 | 2.62 | 11.05 | 2.08 | 0.037093 |
| | | d2 | -1.06 | 2.27 | 8.63 | 2.37 | 9.69 | 1.81 | 0.001948 |
| | | d3 | -0.92 | 2.25 | 9.24 | 2.35 | 10.16 | 1.63 | 0.009683 |
| MIP3b | visit1 | d1 | 1.34 | 0.97 | 8.47 | 1.06 | 7.13 | 0.49 | <.000001 |
| | | d2 | 1.09 | 1.03 | 8 | 1.11 | 6.91 | 0.58 | <.000001 |
| | | d3 | 1.03 | 1.03 | 8.27 | 1.1 | 7.25 | 0.62 | <.000001 |
| MMP9 | visit1 | d1 | 1.18 | 1.07 | 11.72 | 1.07 | 10.54 | 1.1 | <.000001 |
| | | d2 | 1.06 | 1.07 | 11.59 | 1.07 | 10.53 | 1.03 | <.000001 |
| | | d3 | 0.86 | 1.01 | 11.62 | 0.97 | 10.76 | 1.16 | <.000001 |
| SCF R | visit1 | d1 | -0.21 | 0.6 | 9.21 | 0.63 | 9.42 | 0.46 | 0.02359 |
| | | d2 | -0.3 | 0.61 | 8.88 | 0.69 | 9.18 | 0.39 | 0.0011 |
| | | d3 | -0.29 | 0.52 | 9.16 | 0.53 | 9.44 | 0.48 | 0.000432 |
| ST2 | visit1 | d1 | 1.75 | 1.24 | 8.6 | 1.34 | 6.85 | 0.67 | <.000001 |
| | | d2 | 1.43 | 1.25 | 8 | 1.36 | 6.57 | 0.59 | <.000001 |
| | | d3 | 1.49 | 1.32 | 8.37 | 1.44 | 6.88 | 0.59 | <.000001 |
| TIMP1 | visit1 | d1 | 1.15 | 0.52 | 13.44 | 0.53 | 12.3 | 0.5 | <.000001 |
| | | d2 | 1.09 | 0.61 | 13.27 | 0.64 | 12.18 | 0.45 | <.000001 |
| | | d3 | 0.53 | 0.41 | 13.17 | 0.4 | 12.64 | 0.45 | <.000001 |

FIGURE 5D
SlideMapName Prot mics4.5

| Analyte Name | Variable | RunDay | DX Diff (1-2) Mean | DX Diff (1-2) Std Dev | Sepsis Mean | Sepsis Std Dev | Sick Mean | Sick Std Dev | Pr > F |
|---|---|---|---|---|---|---|---|---|---|
| ALCAM | visit1 | d1 | -0.37 | 0.6 | 10.97 | 0.62 | 11.34 | 0.51 | 0.000045 |
|  |  | d2 | -0.57 | 0.74 | 10.38 | 0.74 | 10.95 | 0.73 | <.000001 |
| FGF-4 | visit1 | d1 | -0.5 | 0.42 | 7.63 | 0.42 | 8.14 | 0.44 | <.000001 |
|  |  | d2 | -0.55 | 0.47 | 7.71 | 0.48 | 8.26 | 0.43 | <.000001 |
| Follistatin | visit1 | d1 | 0.36 | 0.86 | 9 | 0.92 | 8.64 | 0.58 | 0.005153 |
|  |  | d2 | 0.35 | 0.93 | 9.05 | 0.99 | 8.71 | 0.61 | 0.011832 |
|  |  | d3 | 0.46 | 0.81 | 8.9 | 0.84 | 8.43 | 0.7 | 0.008234 |
| GRO-g | visit1 | d1 | -1.37 | 1.47 | 10.44 | 1.56 | 11.81 | 1.03 | <.000001 |
|  |  | d2 | -1.7 | 1.83 | 9.99 | 1.98 | 11.69 | 1.17 | <.000001 |
|  |  | d3 | -0.69 | 1.44 | 10.06 | 1.49 | 10.74 | 1.18 | 0.002013 |
| I-TAC | visit1 | d1 | -2.25 | 1.66 | 8.21 | 1.63 | 10.47 | 1.79 | <.000001 |
|  |  | d2 | -1.79 | 1.52 | 8.17 | 1.47 | 9.96 | 1.71 | <.000001 |
|  |  | d3 | -1.61 | 1.61 | 8.2 | 1.57 | 9.81 | 1.78 | <.000001 |
| ICAM-1 | visit1 | d1 | -0.28 | 0.66 | 12.31 | 0.61 | 12.59 | 0.84 | 0.004909 |
|  |  | d2 | -0.33 | 0.73 | 11.91 | 0.73 | 12.24 | 0.66 | 0.002788 |
|  |  | d3 | -0.18 | 0.46 | 12.91 | 0.45 | 13.09 | 0.48 | 0.008961 |
| IFN-g | visit1 | d1 | -0.82 | 0.78 | 6.15 | 0.79 | 6.96 | 0.74 | <.000001 |
|  |  | d2 | -0.56 | 0.64 | 6.05 | 0.64 | 6.61 | 0.67 | <.000001 |
|  |  | d3 | -0.52 | 0.84 | 5.93 | 0.87 | 6.45 | 0.73 | 0.000093 |
| IGF-II | visit1 | d1 | -1.14 | 0.91 | 11.25 | 0.97 | 12.4 | 0.55 | <.000001 |
|  |  | d2 | -1.17 | 0.92 | 10.85 | 0.99 | 12.02 | 0.53 | <.000001 |
|  |  | d3 | -1.09 | 0.84 | 11.94 | 0.91 | 13.04 | 0.44 | <.000001 |
| IGF-IR | visit1 | d1 | -0.52 | 0.47 | 9.07 | 0.46 | 9.59 | 0.51 | <.000001 |
|  |  | d2 | -0.26 | 0.46 | 8.6 | 0.47 | 8.87 | 0.45 | 0.000152 |
|  |  | d3 | -0.24 | 0.32 | 8.84 | 0.33 | 9.08 | 0.29 | 0.000002 |
| IGFBP-1 | visit1 | d1 | 2.52 | 1.19 | 14.79 | 1.07 | 12.27 | 1.61 | <.000001 |
|  |  | d2 | 2.54 | 1.23 | 14.18 | 1.16 | 11.64 | 1.5 | <.000001 |
|  |  | d3 | 2.69 | 1.16 | 14.62 | 1.03 | 11.93 | 1.63 | <.000001 |
| IGFBP-3 | visit1 | d1 | -0.49 | 0.7 | 12.43 | 0.73 | 12.91 | 0.56 | 0.000004 |
|  |  | d2 | -0.71 | 0.88 | 10.78 | 0.92 | 11.49 | 0.69 | <.000001 |
|  |  | d3 | -0.58 | 0.58 | 12.77 | 0.59 | 13.36 | 0.43 | <.000001 |
| IGFBP-4 | visit1 | d2 | -0.28 | 0.69 | 10.67 | 0.72 | 10.95 | 0.53 | 0.006516 |
|  |  | d3 | -0.18 | 0.47 | 11.59 | 0.46 | 11.78 | 0.5 | 0.010541 |
| IL-10rb | visit1 | d1 | -0.31 | 0.64 | 8.59 | 0.65 | 8.9 | 0.58 | 0.001268 |
|  |  | d3 | 0.35 | 0.64 | 8.6 | 0.64 | 8.25 | 0.66 | 0.000563 |

FIGURE 5D (Cont'd.)
SlideMapName Prot mics4.5

| | | | DX | | | | | | |
|---|---|---|---|---|---|---|---|---|---|
| | | | Diff (1-2) | | Sepsis | | Sick | | |
| | | | Mean | Std Dev | Mean | Std Dev | Mean | Std Dev | Pr > F |
| Analyte Name | Variable | RunDay | | | | | | | |
| IL-16 | visit1 | d1 | -1.34 | 0.68 | 6.79 | 0.82 | 8.12 | 1.09 | <.000001 |
| | | d2 | -0.77 | 0.75 | 6.61 | 0.72 | 7.38 | 0.87 | <.000001 |
| | | d3 | -1.28 | 0.87 | 6.57 | 0.77 | 7.85 | 1.2 | <.000001 |
| IL-1srII | visit1 | d1 | 1.06 | 1.27 | 9.15 | 1.36 | 8.09 | 0.84 | <.000001 |
| | | d2 | 0.73 | 1.26 | 8.97 | 1.35 | 8.24 | 0.79 | 0.000112 |
| | | d3 | 1.58 | 1.37 | 9.26 | 1.48 | 7.68 | 0.71 | <.000001 |
| IL-2rb | visit1 | d2 | -0.51 | 0.49 | 7.34 | 0.49 | 7.85 | 0.48 | <.000001 |
| LT bR | visit1 | d1 | 0.63 | 0.88 | 9.76 | 0.89 | 9.12 | 0.82 | 0.000002 |
| | | d2 | 1.01 | 1.03 | 9.78 | 1.04 | 8.77 | 1 | <.000001 |
| | | d3 | 1.28 | 1 | 9.61 | 1 | 8.32 | 0.97 | <.000001 |
| MIP-3a | visit1 | d1 | 0.69 | 1.44 | 9.2 | 1.54 | 8.51 | 0.88 | 0.001427 |
| | | d2 | 0.95 | 1.49 | 9.22 | 1.63 | 8.27 | 0.87 | 0.000023 |
| | | d3 | 0.92 | 1.43 | 9.27 | 1.52 | 8.35 | 0.99 | 0.000028 |
| PDGF-Ra | visit1 | d2 | -0.18 | 0.57 | 7.25 | 0.59 | 7.43 | 0.48 | 0.045536 |
| | | d3 | 0.31 | 0.56 | 7.51 | 0.56 | 7.19 | 0.55 | 0.000332 |
| PF4 | visit1 | d1 | -0.57 | 0.51 | 14.69 | 0.55 | 15.26 | 0.27 | <.000001 |
| | | d3 | -0.35 | 0.42 | 14.71 | 0.46 | 15.06 | 0.21 | <.000001 |
| VAP-1 | visit1 | d1 | -0.24 | 0.61 | 13.57 | 0.65 | 13.81 | 0.39 | 0.008642 |
| | | d2 | -0.38 | 0.6 | 13.47 | 0.63 | 13.85 | 0.42 | 0.000021 |
| | | d3 | -0.65 | 0.54 | 13.35 | 0.58 | 14 | 0.34 | <.000001 |
| VE-cadherin | visit1 | d1 | -0.61 | 0.65 | 11.76 | 0.67 | 12.37 | 0.59 | <.000001 |
| | | d2 | -0.52 | 0.78 | 11.11 | 0.82 | 11.63 | 0.62 | 0.000012 |
| | | d3 | -0.61 | 0.56 | 12.46 | 0.57 | 13.07 | 0.54 | <.000001 |
| VEGF-D | visit1 | d2 | -0.53 | 0.59 | 6.29 | 0.56 | 6.82 | 0.73 | 0.000002 |
| | | d3 | -0.23 | 0.46 | 8.05 | 0.43 | 8.29 | 0.55 | 0.001004 |

FIGURE 5E
SlideMapName Proteomics5.3I

| Analyte Name | Variable | RunDay | DX | | | | | | Pr > F |
|---|---|---|---|---|---|---|---|---|---|
| | | | Diff (1-2) | | Sepsis | | Sick | | |
| | | | Mean | Std Dev | Mean | Std Dev | Mean | Std Dev | |
| AFP | visit1 | d1 | -1.06 | 0.95 | 8.57 | 0.97 | 9.63 | 0.85 | <.000001 |
| | | d2 | -0.97 | 0.95 | 8.59 | 0.96 | 9.57 | 0.88 | <.000001 |
| | | d3 | -1.03 | 0.97 | 8.3 | 1 | 9.33 | 0.83 | <.000001 |
| CD141 | visit1 | d1 | 0.4 | 0.9 | 9.9 | 0.94 | 9.5 | 0.72 | 0.002805 |
| | | d2 | 0.55 | 0.85 | 9.29 | 0.87 | 8.74 | 0.78 | 0.00002 |
| | | d3 | 0.52 | 0.84 | 9.57 | 0.66 | 9.05 | 0.6 | 0.000045 |
| CNTF Ra | visit1 | d1 | -0.15 | 0.51 | 7.19 | 0.54 | 7.35 | 0.39 | 0.043545 |
| | | d2 | -0.46 | 0.5 | 7.25 | 0.49 | 7.71 | 0.57 | <.000001 |
| | | d3 | -0.34 | 0.54 | 7.08 | 0.52 | 7.42 | 0.59 | 0.000028 |
| CRP | visit1 | d1 | -0.3 | 0.43 | 13.1 | 0.46 | 13.4 | 0.28 | 0.000003 |
| | | d2 | -0.46 | 0.57 | 13.21 | 0.62 | 13.67 | 0.26 | <.000001 |
| | | d3 | -0.48 | 0.47 | 13.08 | 0.5 | 13.56 | 0.32 | <.000001 |
| E-Selectin | visit1 | d1 | 1.15 | 1.23 | 12.46 | 1.39 | 11.31 | 0.94 | <.000001 |
| | | d2 | 1.38 | 1.25 | 12.43 | 1.31 | 11.05 | 0.94 | <.000001 |
| | | d3 | 1.32 | 1.21 | 12.5 | 1.29 | 11.18 | 0.8 | <.000001 |
| FGF21 | visit1 | d1 | 1.28 | 1.39 | 9.43 | 1.51 | 8.15 | 0.62 | <.000001 |
| | | d2 | 1.27 | 1.41 | 9.69 | 1.52 | 8.43 | 0.8 | <.000001 |
| | | d3 | 1.24 | 1.35 | 9.3 | 1.46 | 8.07 | 0.78 | <.000001 |
| HCG | visit1 | d1 | -0.32 | 0.82 | 6.52 | 0.72 | 6.84 | 1.15 | 0.009049 |
| | | d2 | -0.28 | 0.76 | 6.66 | 0.66 | 6.93 | 1.1 | 0.015729 |
| | | d3 | -0.43 | 0.76 | 6.64 | 0.7 | 7.07 | 1.04 | 0.000248 |
| IGFBP-6 | visit1 | d2 | 0.31 | 0.44 | 12.85 | 0.47 | 12.54 | 0.3 | 0.000003 |
| | | d3 | 0.26 | 0.45 | 12.9 | 0.48 | 12.64 | 0.3 | 0.000137 |
| IL-18 | visit1 | d1 | 0.48 | 1.03 | 10.7 | 1.07 | 10.22 | 0.81 | 0.002857 |
| | | d3 | 0.62 | 1 | 10.78 | 1.04 | 10.16 | 0.85 | 0.000033 |
| LIF Ra | visit1 | d2 | -0.18 | 0.37 | 7.49 | 0.39 | 7.67 | 0.3 | 0.001838 |
| | | d3 | -0.15 | 0.38 | 7.5 | 0.38 | 7.65 | 0.36 | 0.007441 |
| MIF | visit1 | d1 | -1.39 | 1.25 | 9.36 | 1.28 | 10.75 | 1.08 | <.000001 |
| | | d2 | -1.24 | 1.16 | 9.32 | 1.21 | 10.57 | 0.89 | <.000001 |
| | | d3 | -1.09 | 1.16 | 9.06 | 1.21 | 10.15 | 0.88 | <.000001 |
| MMP-8 | visit1 | d1 | 1.85 | 1.26 | 14.26 | 1.11 | 12.41 | 1.75 | <.000001 |
| | | d2 | 1.78 | 1.16 | 14.3 | 1.02 | 12.52 | 1.61 | <.000001 |
| | | d3 | 1.91 | 1.2 | 14.07 | 1.09 | 12.16 | 1.58 | <.000001 |

FIGURE 5E (Cont'd.)
SlideMapName Proteomics5.31

| Analyt Name | Variable | RunDay | DX | | | | | | Pr > F |
|---|---|---|---|---|---|---|---|---|---|
| | | | Diff (1-2) | | Sepsis | | Sick | | |
| | | | Mean | Std Dev | Mean | Std Dev | Mean | Std D v | |
| Neut Elast | visit1 | d2 | 0.32 | 0.55 | 12.52 | 0.55 | 12.2 | 0.57 | 0.00011 |
| | | d3 | 0.34 | 0.51 | 12.28 | 0.52 | 11.94 | 0.48 | 0.000012 |
| P-Selectin | visit1 | d1 | -0.7 | 1.04 | 12.04 | 1.07 | 12.74 | 0.9 | 0.000009 |
| | | d2 | -0.58 | 0.97 | 12.06 | 1.03 | 12.65 | 0.71 | 0.000069 |
| | | d3 | -0.34 | 0.79 | 12.11 | 0.81 | 12.45 | 0.69 | 0.004137 |

FIGURE 5E (Cont'd.)
SlideMapName Proteomics5.31

| Analyte Name | Variable | RunDay | DX | | | | | | Pr > F |
|---|---|---|---|---|---|---|---|---|---|
| | | | Diff (1-2) | | Sepsis | | Sick | | |
| | | | Mean | Std Dev | Mean | Std Dev | Mean | Std Dev | |
| PAI-II | visit1 | d1 | -1.01 | 0.94 | 6.98 | 0.94 | 7.99 | 0.96 | <.000001 |
| | | d2 | -0.69 | 1.04 | 7.02 | 1.04 | 7.71 | 1.03 | 0.000011 |
| ProteinC | visit1 | d1 | -0.39 | 0.49 | 12.87 | 0.49 | 13.27 | 0.49 | <.000001 |
| | | d2 | -0.17 | 0.42 | 12.75 | 0.45 | 12.92 | 0.24 | 0.007921 |
| | | d3 | -0.16 | 0.43 | 12.63 | 0.47 | 12.8 | 0.23 | 0.011405 |
| ProteinS | visit1 | d1 | 0.26 | 0.4 | 12 | 0.38 | 11.74 | 0.44 | 0.09001 |
| | | d2 | 0.28 | 0.44 | 12 | 0.46 | 11.72 | 0.35 | 0.009033 |
| | | d3 | 0.1 | 0.3 | 11.85 | 0.32 | 11.75 | 0.21 | 0.039524 |
| TSH | visit1 | d1 | -0.32 | 0.49 | 6.83 | 0.48 | 7.15 | 0.53 | 0.000014 |
| | | d2 | -0.48 | 0.44 | 7.03 | 0.46 | 7.51 | 0.35 | <.000001 |
| | | d3 | -0.18 | 0.39 | 6.96 | 0.4 | 7.14 | 0.32 | 0.001454 |

FIGURE 6A

| Analyt Name | THERAPY | Variabl | RunDay | SURVQUES | | | | | | Pr > F |
|---|---|---|---|---|---|---|---|---|---|---|
| | | | | Aliv at Day 28 | | D ad at Day 28 | | Diff (1-2) | | |
| | | | | Mean | Std Dev | Mean | Std D v | Mean | Std Dev | |
| BLC | PLACEBO | visit1 | d1 | 7.05 | 1.01 | 7.65 | 1.44 | -0.61 | 1.25 | 0.003882 |
| | | | d2 | 6.74 | 1.04 | 7.23 | 1.35 | -0.49 | 1.22 | 0.0089 |
| | | | d3 | 7.34 | 1.09 | 8.05 | 1.36 | -0.71 | 1.24 | 0.001369 |
| | | visit2 | d1 | 7.07 | 1.13 | 7.54 | 1.39 | -0.47 | 1.28 | 0.01435 |
| | | | d2 | 6.68 | 1.13 | 7.15 | 1.25 | -0.47 | 1.2 | 0.009799 |
| | | | d3 | 7.36 | 1.12 | 7.85 | 1.34 | -0.49 | 1.25 | 0.021498 |
| EGF | PLACEBO | visit1 | d1 | 8.12 | 1.4 | 7.52 | 1.12 | 0.61 | 1.26 | 0.012925 |
| | | | d3 | 8.36 | 1.44 | 7.82 | 1.11 | 0.54 | 1.28 | 0.025237 |
| Eot2 | PLACEBO | visit1 | d1 | 11.13 | 1.03 | 10.57 | 1.07 | 0.55 | 1.05 | 0.00118 |
| | | | d2 | 10.77 | 0.96 | 10.27 | 1.13 | 0.5 | 1.06 | 0.005755 |
| | | | d3 | 11.05 | 1.03 | 10.55 | 1.15 | 0.5 | 1.1 | 0.00662 |
| | | visit2 | d1 | 11.09 | 1.23 | 10.68 | 1 | 0.41 | 1.11 | 0.02131 |
| | | | d2 | 10.73 | 1.07 | 10.31 | 1.13 | 0.43 | 1.1 | 0.041176 |
| | | | d3 | 11.03 | 1.13 | 10.59 | 1.09 | 0.45 | 1.11 | 0.023063 |
| IL-15 | PLACEBO | visit1 | d1 | 6.22 | 0.68 | 6.52 | 0.61 | -0.3 | 0.69 | 0.006281 |
| | | | d2 | 5.93 | 6.64 | 6.26 | 0.72 | -0.33 | 0.68 | 0.001209 |
| | | | d3 | 6.47 | 0.63 | 6.69 | 0.64 | -0.22 | 0.63 | 0.019567 |
| | | visit2 | d1 | 6.25 | 0.62 | 6.64 | 0.69 | -0.39 | 0.66 | 0.000391 |
| | | | d2 | 5.81 | 0.78 | 6.38 | 0.76 | -0.57 | 0.77 | 0.000004 |
| | | | d3 | 6.33 | 0.62 | 6.74 | 0.79 | -0.41 | 0.72 | 0.002256 |
| IL-1ra | PLACEBO | visit1 | d1 | 11.84 | 2.86 | 13.21 | 2.22 | -1.37 | 2.54 | 0.00091 |
| | | | d2 | 11.46 | 2.97 | 12.78 | 2.4 | -1.33 | 2.68 | 0.001348 |
| | | | d3 | 11.67 | 2.9 | 13.18 | 2.56 | -1.51 | 2.63 | 0.000309 |
| | | visit2 | d1 | 9.42 | 2.52 | 11.52 | 2.87 | -2.1 | 2.63 | 0.000016 |
| | | | d2 | 9.06 | 2.8 | 11.1 | 2.66 | -2.04 | 2.72 | 0.000022 |
| | | | d3 | 9.58 | 2.46 | 11.5 | 2.69 | -1.92 | 2.58 | 0.000061 |
| IL-2sRa | PLACEBO | visit1 | d2 | 13.1 | 1.38 | 13.45 | 1.35 | -0.35 | 1.36 | 0.034864 |
| | | | d3 | 13.43 | 1.33 | 13.75 | 1.24 | -0.33 | 1.28 | 0.064056 |
| | | visit2 | d2 | 12.87 | 1.45 | 13.48 | 1.28 | -0.61 | 1.36 | 0.001498 |
| | | | d3 | 13.23 | 1.29 | 13.79 | 1.11 | -0.57 | 1.19 | 0.001056 |
| IL-6 | PLACEBO | visit1 | d1 | 10.93 | 2.92 | 12.03 | 2.51 | -1.1 | 2.71 | 0.008392 |
| | | | d2 | 10.55 | 3.17 | 11.94 | 2.47 | -1.39 | 2.81 | 0.00127 |
| | | | d3 | 10.98 | 2.93 | 12.39 | 2.3 | -1.41 | 2.6 | 0.000781 |
| | | visit2 | d1 | 9.09 | 2.19 | 11.03 | 2.33 | -1.94 | 2.27 | 0.003007 |
| | | | d2 | 8.68 | 2.31 | 10.6 | 2.51 | -1.91 | 2.42 | 0.00901 |
| | | | d3 | 9.28 | 2.01 | 11.05 | 2.4 | -1.78 | 2.24 | 0.000096 |
| IL-8 | PLACEBO | visit1 | d1 | 11 | 1.36 | 11.6 | 1.72 | -0.6 | 1.56 | 0.013805 |
| | | | d2 | 10.54 | 1.71 | 11.41 | 1.96 | -0.87 | 1.86 | 0.002776 |
| | | | d3 | 10.79 | 1.85 | 11.99 | 1.83 | -1.2 | 1.83 | 0.000156 |
| | | visit2 | d1 | 10.05 | 0.83 | 10.9 | 1.73 | -0.85 | 1.39 | 0.000356 |
| | | | d2 | 9.66 | 1.19 | 10.81 | 1.63 | -1.15 | 1.45 | 0.000005 |
| | | | d3 | 10.04 | 0.7 | 11.21 | 1.74 | -1.17 | 1.38 | 0.000012 |
| MCP-2 | PLACEBO | visit1 | d1 | 7.44 | 1.32 | 8.53 | 2.01 | -1.09 | 1.73 | 0.000421 |
| | | | d2 | 6.78 | 1.2 | 7.62 | 1.82 | -0.85 | 1.56 | 0.00078 |
| | | | d3 | 7.32 | 1.1 | 8.63 | 1.84 | -1.31 | 1.54 | 0.000092 |
| | | visit2 | d1 | 7.07 | 1.37 | 8.21 | 1.71 | -1.13 | 1.44 | 0.000036 |
| | | | d2 | 6.42 | 1 | 7.2 | 1.38 | -0.79 | 1.22 | 0.000108 |
| | | | d3 | 7 | 1.02 | 8.13 | 1.66 | -1.1 | 1.42 | 0.000028 |
| MCP-3 | PLACEBO | visit1 | d1 | 5.96 | 0.59 | 6.18 | 0.73 | -0.22 | 0.67 | 0.034811 |
| | | | d2 | 5.43 | 0.63 | 5.79 | 0.73 | -0.35 | 0.67 | 0.001009 |
| | | | d3 | 6 | 0.52 | 6.25 | 0.57 | -0.25 | 0.55 | 0.014756 |
| | | visit2 | d1 | 5.88 | 0.5 | 6.24 | 0.72 | -0.37 | 0.63 | 0.00014 |
| | | | d2 | 5.5 | 0.61 | 5.86 | 0.73 | -0.36 | 0.68 | 0.000469 |
| | | | d3 | 5.86 | 0.61 | 6.21 | 0.66 | -0.35 | 0.64 | 0.006039 |

FIGURE 6B

| Analyt Name | THERAPY | Variable | RunDay | SURVQUES Aliv at Day 28 Mean | Std Dv | D ad at Day 28 Mean | Std Dv | Diff (1-2) Mean | Std Dev | Pr > F |
|---|---|---|---|---|---|---|---|---|---|---|
| AR | PLACEBO | visit1 | d1 | 7.23 | 0.54 | 7.53 | 0.65 | -0.3 | 0.6 | 0.000864 |
|  |  |  | d2 | 7.17 | 0.6 | 7.53 | 0.68 | -0.36 | 0.64 | 0.000462 |
|  |  | visit2 | d1 | 7.11 | 0.42 | 7.5 | 0.7 | -0.39 | 0.53 | 0.000035 |
|  |  |  | d2 | 7.08 | 0.67 | 7.56 | 0.65 | -0.48 | 0.66 | 0.000004 |
| BDNF | PLACEBO | visit1 | d1 | 12.8 | 1.19 | 11.99 | 1.18 | 0.81 | 1.35 | 0.000237 |
|  |  |  | d2 | 12.33 | 1.11 | 11.64 | 1.27 | 0.69 | 1.2 | 0.000612 |
|  |  |  | d3 | 12.8 | 1.42 | 12.1 | 1.24 | 0.7 | 1.31 | 0.012337 |
|  |  | visit2 | d1 | 12.33 | 1.29 | 11.26 | 1.37 | 1.07 | 1.34 | 0.000002 |
|  |  |  | d2 | 11.81 | 1.29 | 10.87 | 1.3 | 0.94 | 1.3 | 0.000023 |
|  |  |  | d3 | 12.47 | 0.92 | 11.18 | 1.31 | 1.29 | 1.17 | <.000001 |
| GCP-2 | PLACEBO | visit2 | d1 | 6.66 | 0.7 | 6.94 | 0.73 | -0.28 | 0.72 | 0.014131 |
|  |  |  | d2 | 6.89 | 0.8 | 7.32 | 0.69 | -0.43 | 0.65 | 0.001527 |
| HCC4 | PLACEBO | visit1 | d1 | 11.08 | 1.58 | 10.62 | 1.73 | 0.47 | 1.66 | 0.012266 |
|  |  |  | d2 | 10.34 | 1.69 | 9.96 | 1.73 | 0.38 | 1.71 | 0.063299 |
|  |  | visit2 | d1 | 11.83 | 1.24 | 11.11 | 1.7 | 0.71 | 1.5 | 0.001485 |
|  |  |  | d2 | 10.97 | 1.76 | 10.4 | 1.63 | 0.57 | 1.69 | 0.022365 |
|  |  |  | d3 | 11.62 | 1.31 | 10.05 | 1.87 | 1.57 | 1.67 | 0.000288 |
| I-309 | PLACEBO | visit2 | d1 | 6.48 | 0.51 | 6.69 | 0.54 | -0.21 | 0.53 | 0.011069 |
|  |  |  | d2 | 6.85 | 0.77 | 7.33 | 0.78 | -0.48 | 0.78 | 0.000069 |
| IL-1b | PLACEBO | visit2 | d1 | 5.62 | 0.53 | 5.92 | 0.58 | -0.3 | 0.55 | 0.09116 |
|  |  |  | d2 | 4.88 | 0.7 | 5.52 | 0.92 | -0.64 | 0.82 | 0.000025 |
| M-CSF | PLACEBO | visit1 | d1 | 10.13 | 0.7 | 10.42 | 0.93 | -0.29 | 0.83 | 0.041699 |
|  |  |  | d2 | 9.75 | 0.76 | 10.24 | 1 | -0.49 | 0.89 | 0.00166 |
| MCP-1 | PLACEBO | visit1 | d1 | 12.03 | 1.64 | 12.63 | 1.78 | -0.6 | 1.73 | 0.036096 |
|  |  |  | d2 | 11.1 | 1.99 | 12.15 | 2.03 | -1.06 | 2.01 | 0.001137 |
|  |  | visit2 | d1 | 11.23 | 1.29 | 12.37 | 1.65 | -1.13 | 1.49 | 0.000073 |
|  |  |  | d2 | 10.29 | 1.33 | 11.67 | 1.76 | -1.38 | 1.58 | 0.000004 |
|  |  |  | d3 | 10.63 | 1.55 | 11.78 | 1.76 | -1.15 | 1.68 | 0.001709 |
| MIG | PLACEBO | visit1 | d1 | 10.07 | 2.17 | 10.92 | 2.31 | -0.85 | 2.25 | 0.025287 |
|  |  |  | d2 | 9.87 | 2.07 | 10.8 | 2.4 | -0.94 | 2.26 | 0.011627 |
|  |  | visit2 | d1 | 9.42 | 1.83 | 10.66 | 2.21 | -1.24 | 2.03 | 0.000573 |
|  |  |  | d2 | 8.94 | 1.91 | 10.58 | 2.34 | -1.64 | 2.15 | 0.000043 |
| NT4 | PLACEBO | visit2 | d1 | 6.5 | 0.55 | 6.8 | 0.63 | -0.3 | 0.59 | 0.000959 |
|  |  |  | d2 | 6.77 | 0.8 | 7.31 | 0.85 | -0.54 | 0.85 | 0.000064 |
| Rantes | PLACEBO | visit1 | d1 | 15.52 | 0.35 | 15.3 | 0.77 | 0.21 | 0.61 | 0.023814 |
|  |  |  | d2 | 15.76 | 0.4 | 15.49 | 0.74 | 0.27 | 0.61 | 0.005673 |
|  |  | visit2 | d1 | 15.42 | 0.53 | 15.15 | 0.82 | 0.28 | 0.7 | 0.009634 |
|  |  |  | d2 | 15.62 | 0.67 | 15.27 | 0.88 | 0.35 | 0.79 | 0.065664 |
|  |  |  | d3 | 15.43 | 0.36 | 14.81 | 1.04 | 0.62 | 0.84 | 0.000331 |
| SCF | PLACEBO | visit2 | d1 | 6.95 | 0.53 | 7.23 | 0.57 | -0.28 | 0.55 | 0.005563 |
|  |  |  | d2 | 7.15 | 0.75 | 7.44 | 0.79 | -0.28 | 0.77 | 0.013957 |
| TNF-R1 | PLACEBO | visit1 | d1 | 12.22 | 1.16 | 12.72 | 1 | -0.5 | 1.08 | 0.02922 |
|  |  |  | d2 | 12.08 | 1.32 | 12.66 | 1.16 | -0.57 | 1.24 | 0.014364 |
|  |  | visit2 | d1 | 11.99 | 1.2 | 12.72 | 1.08 | -0.73 | 1.14 | 0.001318 |
|  |  |  | d2 | 11.85 | 1.36 | 12.75 | 1.24 | -0.9 | 1.3 | 0.000385 |

FIGURE 6B (Cont'd.)

| | | | | SURVQUES | | | | | | |
| | | | | Alive at Day 28 | | Dead at Day 28 | | Diff (1-2) | | |
| Analyte Name | THERAPY | Variabl | RunDay | M an | Std Dev | M an | Std D v | Mean | Std Dev | Pr > F |
|---|---|---|---|---|---|---|---|---|---|---|
| TNF-a | PLACEBO | visit1 | d1 | 7.52 | 0.79 | 7.78 | 0.69 | -0.26 | 0.76 | 0.03848 |
| | | | d2 | 7.44 | 0.65 | 7.67 | 0.68 | -0.23 | 0.67 | 0.030127 |
| | | visit2 | d1 | 7.45 | 0.69 | 7.75 | 0.72 | -0.3 | 0.71 | 0.008657 |
| | | | d2 | 7.43 | 0.67 | 7.74 | 0.73 | -0.31 | 0.69 | 0.0093 |

FIGURE 6C

| | | | | SURVQUES | | | | | |
|---|---|---|---|---|---|---|---|---|---|
| | | | | Aliv at Day 28 | | D ad at Day 28 | | Diff (1-2) | |
| | | | | Mean | Std D v | Mean | Std D v | M an | Std D v | Pr > F |
| Analyt Name | THERAPY | Variabl | RunDay | | | | | | | |
| HVEM | PLACEBO | visit2 | d2 | 7.85 | 0.94 | 8.34 | 1.04 | -0.5 | 0.99 | 0.009427 |
| | | | d3 | 7.93 | 0.8 | 8.43 | 0.92 | -0.5 | 0.87 | 0.004603 |
| IGFBP2 | PLACEBO | visit1 | d2 | 13.55 | 0.66 | 13.88 | 0.7 | -0.33 | 0.68 | 0.018424 |
| | | | d3 | 13.49 | 0.38 | 13.78 | 0.49 | -0.29 | 0.44 | 0.000894 |
| | | visit2 | d2 | 13.57 | 0.7 | 13.94 | 0.73 | -0.37 | 0.72 | 0.007514 |
| | | | d3 | 13.55 | 0.38 | 13.79 | 0.53 | -0.24 | 0.47 | 0.004706 |
| MIP3b | PLACEBO | visit2 | d1 | 8.1 | 0.85 | 8.46 | 1.06 | -0.36 | 0.96 | 0.04498 |
| | | | d2 | 7.51 | 0.94 | 7.85 | 1.07 | -0.34 | 1.01 | 0.042278 |
| | | | d3 | 7.69 | 0.96 | 8.27 | 1.04 | -0.58 | 1 | 0.001433 |
| SCF R | PLACEBO | visit1 | d1 | 9.39 | 0.51 | 9.08 | 0.68 | 0.31 | 0.6 | 0.018749 |
| | | | d2 | 9.07 | 0.61 | 8.73 | 0.69 | 0.33 | 0.66 | 0.02022 |
| | | | d3 | 9.31 | 0.46 | 9.04 | 0.51 | 0.27 | 0.49 | 0.013796 |
| ST2 | PLACEBO | visit2 | d1 | 7.8 | 0.97 | 8.49 | 1.31 | -0.69 | 1.16 | 0.001416 |
| | | | d2 | 7.11 | 0.84 | 7.71 | 1.19 | -0.6 | 1.04 | 0.0017 |
| | | | d3 | 7.35 | 1.05 | 8.25 | 1.44 | -0.9 | 1.29 | 0.000076 |

FIGURE 6D

| Analyt Name | THERAPY | Variable | RunDay | SURVQUES ||||||  |
|---|---|---|---|---|---|---|---|---|---|---|
| | | | | Aliv at Day 28 || D ad at Day 28 || Diff (1-2) || Pr > F |
| | | | | Mean | Std D v | Mean | Std D v | M an | Std D v | |
| CD27 | PLACEBO | visit2 | d1 | 8.54 | 1.09 | 9.33 | 1.25 | -0.79 | 1.18 | 0.000864 |
| | | | d2 | 8.13 | 1.19 | 8.69 | 1.35 | -0.55 | 1.27 | 0.029206 |
| | | | d3 | 8.63 | 1.43 | 9.28 | 1.28 | -0.66 | 1.35 | 0.016086 |
| Follistatin | PLACEBO | visit2 | d1 | 8.64 | 0.54 | 9.13 | 0.96 | -0.49 | 0.82 | 0.001338 |
| | | | d2 | 8.92 | 0.71 | 9.29 | 0.96 | -0.37 | 0.85 | 0.03658 |
| | | | d3 | 8.66 | 0.52 | 8.95 | 0.85 | -0.28 | 0.75 | 0.028197 |
| I-TAC | PLACEBO | visit2 | d1 | 7.54 | 0.97 | 8.03 | 1.37 | -0.49 | 1.19 | 0.009538 |
| | | | d2 | 7.62 | 0.81 | 8.01 | 1.26 | -0.38 | 1.07 | 0.027429 |
| | | | d3 | 7.61 | 0.97 | 8.13 | 1.34 | -0.52 | 1.18 | 0.007295 |
| IFN-g | PLACEBO | visit1 | d1 | 5.94 | 0.54 | 6.2 | 0.7 | -0.26 | 0.63 | 0.014403 |
| | | | d3 | 5.74 | 0.4 | 5.93 | 0.72 | -0.19 | 0.59 | 0.03821 |
| | | visit2 | d1 | 5.89 | 0.46 | 6.19 | 0.62 | -0.3 | 0.55 | 0.000266 |
| | | | d3 | 5.66 | 0.39 | 5.88 | 0.72 | -0.22 | 0.59 | 0.004331 |
| IGF-II | PLACEBO | visit1 | d1 | 11.53 | 0.76 | 10.96 | 1.18 | 0.57 | 1.01 | 0.003911 |
| | | | d2 | 11.15 | 0.72 | 10.59 | 1.15 | 0.57 | 0.98 | 0.003829 |
| | | | d3 | 12.28 | 0.73 | 11.75 | 0.99 | 0.53 | 0.87 | 0.003578 |
| | | visit2 | d1 | 11.81 | 0.71 | 11.29 | 0.86 | 0.53 | 0.79 | 0.000126 |
| | | | d2 | 11.4 | 0.79 | 10.99 | 0.94 | 0.41 | 0.87 | 0.005136 |
| | | | d3 | 12.59 | 0.66 | 11.97 | 0.93 | 0.62 | 0.82 | 0.000058 |
| IGFBP-1 | PLACEBO | visit1 | d1 | 14.55 | 1.39 | 15.03 | 0.87 | -0.48 | 1.14 | 0.028029 |
| | | | d2 | 13.77 | 1.46 | 14.48 | 0.93 | -0.71 | 1.2 | 0.00142 |
| | | | d3 | 14.32 | 1.31 | 14.85 | 0.92 | -0.54 | 1.13 | 0.012389 |
| | | visit2 | d1 | 14.09 | 1.43 | 14.85 | 1.1 | -0.77 | 1.26 | 0.000936 |
| | | | d2 | 13.3 | 1.49 | 14.28 | 1.18 | -0.98 | 1.33 | 0.000922 |
| | | | d3 | 13.88 | 1.36 | 14.72 | 1.06 | -0.84 | 1.23 | 0.000296 |
| IGFBP-4 | PLACEBO | visit2 | d1 | 10.72 | 0.58 | 11.13 | 0.58 | -0.41 | 0.55 | 0.000309 |
| | | | d2 | 10.62 | 0.57 | 10.84 | 0.61 | -0.22 | 0.59 | 0.030527 |
| IL-18rb | PLACEBO | visit2 | d1 | 8.48 | 0.67 | 8.79 | 0.55 | -0.31 | 0.63 | 0.005013 |
| | | | d2 | 8.1 | 0.63 | 8.36 | 0.7 | -0.27 | 0.66 | 0.026761 |
| IL-16 | PLACEBO | visit2 | d1 | 6.47 | 0.47 | 6.79 | 0.72 | -0.32 | 0.61 | 0.007043 |
| | | | d2 | 6.35 | 0.47 | 6.64 | 0.67 | -0.29 | 0.59 | 0.005638 |
| | | | d3 | 6.32 | 0.45 | 6.6 | 0.71 | -0.28 | 0.6 | 0.006612 |
| IL-1srII | PLACEBO | visit1 | d1 | 8.68 | 1.15 | 9.4 | 1.48 | -0.72 | 1.34 | 0.000408 |
| | | | d2 | 8.57 | 0.92 | 9.13 | 1.49 | -0.56 | 1.26 | 0.001622 |
| | | | d3 | 8.74 | 1.17 | 9.52 | 1.57 | -0.78 | 1.39 | 0.000348 |
| | | visit2 | d1 | 8.86 | 1.27 | 9.72 | 1.67 | -0.85 | 1.49 | 0.000122 |
| | | | d2 | 8.8 | 1.03 | 9.64 | 1.65 | -0.84 | 1.38 | 0.000051 |
| | | | d3 | 8.92 | 1.34 | 9.97 | 1.66 | -1.05 | 1.53 | 0.000027 |
| LT bR | PLACEBO | visit1 | d1 | 9.51 | 0.79 | 9.87 | 0.95 | -0.37 | 0.88 | 0.010092 |
| | | | d3 | 9.34 | 0.98 | 9.76 | 0.97 | -0.42 | 0.96 | 0.008539 |
| | | visit2 | d1 | 9.53 | 0.91 | 10.22 | 0.98 | -0.69 | 0.95 | 0.000038 |
| | | | d2 | 9.58 | 0.98 | 10.24 | 0.95 | -0.66 | 0.97 | 0.000179 |
| | | | d3 | 9.36 | 0.91 | 10.01 | 0.99 | -0.65 | 0.96 | 0.000076 |
| MIP-3a | PLACEBO | visit1 | d1 | 8.79 | 1.23 | 9.47 | 1.69 | -0.68 | 1.49 | 0.00294 |
| | | | d2 | 8.84 | 1.23 | 9.42 | 1.67 | -0.58 | 1.48 | 0.012387 |
| | | | d3 | 8.9 | 1.24 | 9.44 | 1.51 | -0.54 | 1.39 | 0.007058 |
| | | visit2 | d1 | 8.12 | 0.68 | 9.03 | 1.4 | -0.91 | 1.13 | 0.000001 |
| | | | d2 | 8.2 | 0.78 | 9.02 | 1.37 | -0.82 | 1.14 | 0.000024 |
| | | | d3 | 8.3 | 0.74 | 8.99 | 1.3 | -0.69 | 1.07 | 0.000055 |

FIGURE 6E
Slid MapNam Prot omics5.3l

| | | | | SURVQUES | | | | | |
|---|---|---|---|---|---|---|---|---|---|
| | | | | Aliv at Day 28 | | D ad at Day 28 | | Diff (1-2) | |
| | | | | M an | Std Dev | Mean | Std D v | Mean | Std Dev | Pr > F |
| Analyte Name | THERAPY | Variabl | RunDay | | | | | | | |
| 4-1BB | PLACEBO | visit2 | d2 | 7.03 | 0.53 | 7.22 | 0.65 | -0.22 | 0.6 | 0.026256 |
| | | | d3 | 6.76 | 0.4 | 6.97 | 0.48 | -0.2 | 0.45 | 0.005293 |
| AFP | PLACEBO | visit1 | d1 | 8.84 | 1.16 | 8.36 | 0.86 | 0.48 | 1.02 | 0.016371 |
| | | | d2 | 8.91 | 1.15 | 8.3 | 0.89 | 0.61 | 1.03 | 0.002057 |
| | | | d3 | 8.6 | 1.21 | 8.09 | 0.8 | 0.51 | 1.01 | 0.009839 |
| | | visit2 | d1 | 8.8 | 1.2 | 8.29 | 0.93 | 0.51 | 1.07 | 0.014505 |
| | | | d2 | 8.87 | 1.3 | 8.44 | 0.84 | 0.44 | 1.03 | 0.034755 |
| | | | d3 | 8.53 | 1.27 | 8.03 | 0.83 | 0.5 | 1.05 | 0.022269 |
| AgRP | PLACEBO | visit2 | d1 | 6.5 | 0.65 | 6.89 | 0.85 | -0.39 | 0.76 | 0.002308 |
| | | | d2 | 6.74 | 0.49 | 7.07 | 0.75 | -0.32 | 0.64 | 0.001259 |
| | | | d3 | 6.65 | 0.66 | 7.18 | 0.86 | -0.53 | 0.77 | 0.00009 |
| CD141 | PLACEBO | visit2 | d1 | 9.68 | 0.98 | 10.21 | 0.98 | -0.53 | 0.98 | 0.003046 |
| | | | d2 | 9.24 | 0.9 | 9.59 | 0.91 | -0.35 | 0.86 | 0.010765 |
| | | | d3 | 9.39 | 0.89 | 9.83 | 0.86 | -0.43 | 0.88 | 0.00765 |
| FGF21 | PLACEBO | visit2 | d1 | 8.86 | 1.28 | 9.52 | 1.64 | -0.65 | 1.49 | 0.012856 |
| | | | d2 | 9.17 | 1.31 | 9.91 | 1.55 | -0.73 | 1.44 | 0.003844 |
| | | | d3 | 8.62 | 1.28 | 9.29 | 1.53 | -0.67 | 1.42 | 0.009077 |
| IL-18 | PLACEBO | visit1 | d1 | 10.5 | 0.94 | 10.83 | 1.17 | -0.33 | 1.06 | 0.024614 |
| | | | d3 | 10.51 | 0.91 | 10.93 | 1.07 | -0.42 | 1 | 0.005675 |
| | | visit2 | d1 | 10.31 | 1 | 10.91 | 1.11 | -0.6 | 1.06 | 0.000343 |
| | | | d2 | 10.66 | 0.94 | 11.27 | 1.12 | -0.61 | 1.04 | 0.0001 |
| | | | d3 | 10.48 | 0.87 | 11.11 | 1.11 | -0.63 | 1.01 | 0.000154 |
| MIF | PLACEBO | visit1 | d1 | 8.95 | 0.96 | 9.73 | 1.32 | -0.72 | 1.17 | 0.000379 |
| | | | d2 | 8.88 | 0.96 | 9.6 | 1.19 | -0.73 | 1.09 | 0.000168 |
| | | | d3 | 8.55 | 1.01 | 9.37 | 1.17 | -0.82 | 1.1 | 0.000049 |
| | | visit2 | d1 | 9.76 | 1.18 | 9.55 | 1.32 | -0.78 | 1.37 | 0.00128 |
| | | | d2 | 8.72 | 1.05 | 9.57 | 1.25 | -0.85 | 1.22 | 0.000164 |
| | | | d3 | 8.45 | 0.86 | 9.12 | 1.08 | -0.67 | 0.99 | 0.000133 |
| MMP-8 | PLACEBO | visit2 | d1 | 13.75 | 1.46 | 14.23 | 1.43 | -0.49 | 1.44 | 0.017177 |
| | | | d2 | 13.89 | 1.31 | 14.27 | 1.29 | -0.39 | 1.3 | 0.026793 |
| P-Selectin | PLACEBO | visit1 | d2 | 12.3 | 0.65 | 11.84 | 1.2 | 0.46 | 1.05 | 0.013654 |
| | | | d3 | 12.3 | 0.59 | 11.92 | 0.9 | 0.38 | 0.78 | 0.011523 |
| PAI-II | PLACEBO | visit1 | d1 | 6.76 | 0.52 | 7.23 | 1.23 | -0.44 | 0.97 | 0.001098 |
| | | | d2 | 6.76 | 0.71 | 7.15 | 1.37 | -0.39 | 1.12 | 0.006891 |
| | | | d3 | 7.71 | 1.11 | 8.68 | 1.53 | -0.97 | 1.41 | 0.000014 |
| | | visit2 | d1 | 6.73 | 0.74 | 7.44 | 1.43 | -0.71 | 1.16 | 0.000124 |
| | | | d2 | 6.74 | 0.8 | 7.4 | 1.32 | -0.66 | 1.11 | 0.000165 |
| | | | d3 | 7.72 | 1.23 | 8.69 | 1.48 | -0.96 | 1.37 | 0.000006 |
| ProteinS | PLACEBO | visit2 | d1 | 11.93 | 0.47 | 12.09 | 0.41 | -0.16 | 0.44 | 0.038102 |
| | | | d3 | 11.73 | 0.36 | 11.89 | 0.29 | -0.16 | 0.32 | 0.004756 |

P-values < $10^{-4}$

BIOMARKERS FOR SEPSIS

TECHNICAL FIELD OF THE INVENTION

This invention is related to the area of diagnosis. In particular, it relates to diagnosis, risk assessment, and monitoring of sepsis.

BACKGROUND OF THE INVENTION

Sepsis is the name given to infection when symptoms of inflammatory response are present. Of patients hospitalized in an intensive care unit (ICU) who have an infection, 82% have sepsis. Sepsis is defined as an infection-induced syndrome involving two or more of the following features of systemic inflammation: fever or hypothermia, leukocytosis or leukopenia, tachycardia, and tachypnea or a supranormal minute ventilation. Sepsis may be defined by the presence of any of the following ICD-9-CM codes: 038 (septicemia), 020.0 (septicemic), 790.7 (bacteremia), 117.9 (disseminated fungal infection), 112.5 (disseminated *Candida* infection), and 112.81 (disseminated fungal endocarditis).

Sepsis is diagnosed either by clinical criteria or by culture of microorganisms from the blood of patients suspected of having sepsis plus the presence of features of systemic inflammation. Culturing some microorganisms can be tedious and time-consuming, and may provide a high rate of false negatives. Bloodstream infection is diagnosed by identification of microorganisms in blood specimens from a patient suspected of having sepsis after 24 to 72 hours of laboratory culture. Currently, gram-positive bacteria account for 52% of cases of sepsis, gram-negative bacteria account for 38%, polymicrobial infections for 5%, anaerobes for 1%, and fungi for 5%. For each class of infection listed, there are several different types of microorganisms that can cause sepsis. The high rate of false negative microbiologic cultures leads frequently today to empiric treatment for sepsis in the absence of definitive diagnosis. Infection at many different sites can result in sepsis. The most common sites of infection in patients with sepsis are lung, gut, urinary tract, and primary blood stream site of infection. Since sepsis can be caused by many infection with microorganisms at many different sites, sepsis is a very heterogeneous disease. The heterogeneity of sepsis increases the difficulty in devising a diagnostic test The number of patients with sepsis per year is increasing at 13.7% per year, and was 659,935 in 2000. The incidence of sepsis in the United States in 2000 was 240.4 cases per 100,000 population. Sepsis accounted for 1.3% of all hospitalizations in the U.S. from 1979 to 2000. During this period, there were 750 million hospitalizations in the U.S. and 10.5 million reported cases of sepsis.

Sepsis is the leading cause of death in critically ill patients, the second leading cause of death among patients in non-coronary intensive care units (ICUs), and the tenth leading cause of death overall in the United States. Overall mortality rates for sepsis are 18%. In-hospital deaths related to sepsis were 120,491 (43.9 per 100,000 population) in 2000.

Care of patients with sepsis is expensive and accounts for $17 billion annually in the United States alone. Sepsis is often lethal, killing 20 to 50 percent of severely affected patients. Furthermore, sepsis substantially reduces the quality of life of those who survive: only 56% of patients surviving sepsis are discharged home; 32% are discharged to other health care facilities (i.e., rehabilitation centers or other long-term care facilities), accruing additional costs of care.

Cost of care, morbidity and mortality related to sepsis are largely associated with delayed diagnosis and specific treatment of sepsis and the causal infection. Early diagnosis of sepsis is expected to result in decreased morbidity, mortality and cost of care. The average length of hospital stay in patients with sepsis is twelve days.

Severe sepsis is defined as sepsis associated with acute organ dysfunction. The proportion of patients with sepsis who had any organ failure is 34%, resulting in the identification of 256,033 cases of severe sepsis in 2000. Organ failure had a cumulative effect on mortality: approximately 15% of patients without organ failure died, whereas 70% of patients with 3 or more failing organs (classified as having severe sepsis and septic shock) died. Risk of death from sepsis increases with increasing severity of sepsis. Currently determination of the severity of sepsis and determination of whether, in a patient with sepsis, the sepsis is increasing or decreasing in severity, is based upon clinical events such as failing organs. Determination that, in a patient with sepsis, the sepsis is increasing in severity, may allow more intensive therapy to be given which may increase the likelihood of the patient surviving. The availability of a diagnostic test that would allow monitoring of patients with sepsis to determine whether the sepsis is increasing or decreasing in severity may allow early detection of deterioration and earlier intensification of therapy and less risk of death or disability.

Sepsis results either from community-acquired infections or hospital-acquired infections. Sepsis occurs in 1.3% of all U.S. hospitalizations. Hospital-acquired infections are a major source of sepsis, accounting for 65% of sepsis patients who are admitted to an intensive care unit. Sepsis is a major cause of admission to a hospital intensive care unit. 23-30% of patients admitted to an intensive care unit for longer than 24 hours will develop sepsis. Sepsis is a common complication of prolonged stay in an ICU. 8% of patients who remain in an ICU for longer than 24 hours will develop sepsis.

There is a need for screening diagnostic tests for sepsis and for tests to monitor sepsis severity with relatively few false negatives and high sensitivity and specificity.

SUMMARY OF THE INVENTION

In one embodiment of the invention a method of diagnosing sepsis in a human subject is provide. Concentration of at least one analyte in a test sample from a human subject is compared to concentration of the at least one analyte in a reference range that was determined for one or more control samples obtained from one or more human subjects not suffering from sepsis. The at least one analyte is selected from the group consisting of: IL-1Ra, MCP-1, MPIF-1, TNF-R1, MIG, BLC, HVEM, IL-15, MCP-2, M-CSF, MIP-3b, MMP-9, PARC, and ST-2. Sepsis is diagnosed in the human subject if the concentration of the at least one analyte is elevated in the test sample relative to the reference range for the control samples.

According to another embodiment of the invention a method is provided for diagnosing sepsis in a human subject. Concentration of at least two analytes in a test sample from a human subject is compared to concentration of the at least two analytes in a reference range that was determined for one or more control samples obtained from one or more human subjects not suffering from sepsis. A first analyte of said two analytes is selected from a first group and a second analyte of said two analytes is selected from a second group. The first group consists of: IL-1Ra, MCP-1, MPIF-1, TNF-R1, MIG, BLC, HVEM, IL-15, MCP-2, M-CSF, MIP-3b, MMP-9, PARC, and ST-2. The second group consists of IL-6, sIL-2R, CD141, and MMP-9. Sepsis is diagnosed in the human subject if the concentration of at least one analyte in the first group and at least one analyte in the second group is elevated in the test sample relative to the reference range for the control samples.

According to still another embodiment of the invention a method of diagnosing sepsis in a human subject is provided. Concentration of at least one analyte in a test sample from said human subject is compared to concentration of the at least one analyte in a reference range that was determined for one or more control samples obtained from one or more human subjects not suffering from sepsis. The at least one analyte is selected from the group consisting of: EGF, ENA-78, EOT, Gro-beta, IL-1b, Leptin, MIF, MIP-1a, OSM, Protein C, P-Selectin, and HCC4. Sepsis is diagnosed in the human subject if the concentration of the at least one analyte is depressed in the test sample relative to the reference range for the control samples.

According to still another embodiment of the invention a method is provided of diagnosing sepsis in a human subject. Concentration in a test sample from a human subject of at least one analyte selected from a first group and at least one analyte selected from a second group is compared to concentration of said selected analytes in a reference range that was determined for one or more control samples obtained from one or more human subjects not suffering from sepsis. The first group consists of: EL-1Ra, MCP-1, MPIF-1, TNF-R1, MIG, BLC, HVEM, IL-15, MCP-2, M-CSF, MIP-3b, MMP-9, PARC, and ST-2; and the second group consists of EGF, ENA-78, EOT, Gro-beta, IL-1b, Leptin, MIF, MIP-1a, OSM, Protein C, P-Selectin, and HCC4. Sepsis is diagnosed in the human subject if the concentration of at least one analyte in the first group is elevated in the test sample relative to the control sample and the concentration of at least one analyte in the second group is depressed in the test sample relative to the reference range for the control samples.

Another aspect of the invention is still another method of diagnosing sepsis in a human subject. Concentration of at least one analyte in a test sample from a human subject is compared to concentration of the at least one analyte in a reference range that was determined for one or more control samples obtained from one or more human subjects not suffering from sepsis. The at least one analyte is selected from the group consisting of: IL-1Ra, MCP-1, MPIF-1, TNF-R1, MIG, BLC, HVEM, IL-15, MCP-2, M-CSF, MIP-3b, MMP-9, PARC, ST-2, and fragments or metabolites thereof. Sepsis is diagnosed in the human subject if the concentration of the at least one analyte is elevated in the test sample relative to the reference range for the control samples.

Yet another aspect of the invention is a method of diagnosing sepsis in a human subject at risk of developing sepsis. Concentration in a test sample from a human subject of at least one analyte selected from a first group and at least one analyte selected from a second group is compared to concentration of a reference range that was determined for one or more control samples. The first group consists of: IL-1Ra, MCP-1, MPT-1, TNF-R1, MIG, BLC, HVEM, IL-15, MCP-2, M-CSF, MIP-3b, MMP-9, PARC, and ST-2. The second group consists of EGF, ENA-78, EOT, Gro-beta, IL-1b, Leptin, MIF, MIP-1a, OSM, Protein C, P-Selectin, and HCC4. Sepsis is diagnosed in the human subject if the concentration of at least one analyte in the first group is elevated in the test sample relative to the reference range or at least one analyte in the second group is depressed in the test sample relative to the reference range.

According to still another aspect of the invention a method is provided for diagnosis of deterioration or risk of progression to severe sepsis in a human subject suspected of having or having sepsis. The concentration of one or more analytes in a first sample obtained from a subject is determined. The one or more analytes is selected from a first group consisting of: IL-1Ra, MCP-1, MPIF-1, TNF-R1, MIG, BLC, HVEM, IL-15, MCP-2, M-CSF, MIP-3b, MMP-9, PARC, and ST-2 or a second group consisting of EGF, ENA-78, EOT, Gro-beta, IL-1b, Leptin, MIF, MIP-1a, OSM, Protein C, P-Selectin, and HCC4. The concentration of said one or more analytes is also determined in a second sample obtained from said subject; the second sample is obtained at a time later than the first sample. The concentrations of analytes from said first and second samples are compared. An elevated concentration in the second sample relative to the first of an analyte selected from the first group or a depressed concentration in the second sample relative to the first of an analyte selected from the second group indicates deterioration or risk of progression to severe sepsis in the human subject.

According to still another aspect of the invention a method is provided for diagnosis of deterioration or risk of progression to severe sepsis in a human subject suspected of having or having sepsis. The concentration of one or more analytes in a sample obtained from a subject is determined. The one or more analytes is selected from a first group consisting of: IL-1Ra, MCP-1, MPIF-1, TNF-R1, MIG, BLC, HVEM, IL-15, MCP-2, M-CSF, MIP-3b, MMP-9, PARC, and ST-2 or a second group consisting of EGF, ENA-78, EOT, Gro-beta, IL-1b, Leptin, MIF, MIP-1a, OSM, Protein C, P-Selectin, and HCC4. The concentration of said one or more analytes is compared with a reference range obtained from a one or more control samples obtained from control subjects who have sepsis but did not have severe sepsis. The concentrations of analytes from said patient and reference samples are compared. An elevated concentration in the patient sample relative to the control sample of an analyte selected from the first group or a depressed concentration in the patient sample relative to the control sample of an analyte selected from the second group indicates deterioration or risk of progression to severe sepsis in the test patient.

According to still another aspect of the invention a method is provided for diagnosing sepsis in an acutely ill human subject at risk of developing sepsis. Concentration of one or more analytes in a sample obtained from the subject is determined. The one or more analytes is selected from a first group consisting of: IL-1Ra, MCP-1, MPIF-1, TNF-R1, MIG, BLC, HVEM, IL-15, MCP-2, M-CSF, MIP-3b, MMP-9, PARC, and ST-2; and a second group comsisting of: EGF, ENA-78, EOT, Gro-beta, IL-1b, Leptin, MIF, MIP-1a, OSM, Protein C, P-Selectin, and HCC4. Sepsis in the subject is diagnosed if the concentration of at least one analyte from the first group is elevated or the concentration of at least one analyte from the second group is depressed relative to the concentration of said analyte in a control sample or a reference range that was determined for one or more control samples.

Another embodiment of the invention is a method of diagnosis of improvement in a human subject suspected of having or having sepsis. The concentration of one or more analytes in a first sample obtained from subject is determined. The one or more analytes is selected from a first group consisting of: IL-1Ra, MCP-1, MPIF-1, TNF-R1, MIG, BLC, HVEM, IL-15, MCP-2, M-CSF, MIP-3b, MMP-9, PARC, and ST-2 or a second group consisting of EGF, ENA-78, EOT, Gro-beta, IL-1b, Leptin, MIF, MIP-1a, OSM, Protein C, P-Selectin, and HCC4. The concentration of the one or more analytes is determined in a second sample obtained from said subject. The second sample is obtained at a time later than the time of obtaining the first sample. The concentrations of analytes from said first and second samples are compared. A depressed concentration in the second sample relative to the first of an analyte selected from the first group or an elevated concentration in the second sample relative to the first of an analyte selected from the second group indicates improvement of sepsis or the risk of sepsis in the human subject.

These and other embodiments which will be apparent to those of skill in the art upon reading the specification provide the art with reagents and methods for detection and diagnosis pertaining to sepsis.

BRIEF DESCRIPTION OF THE DRAWINGS

FIG. 2. Causal organisms in the septic samples. "Mixed Gram" indicates a sample containing Gram positive and Gram negative bacteria, and possibly other microorganisms. "No Bacteria Expo" indicates exposure to one or more unknown organisms other than bacteria. "Unconfirmed Gram" indicates a sample comprising bacteria of unknown Gram stain Characteristics.

FIG. 3. Two sets of data for each analyte are shown. The first set is QDA (Quadratic Discriminant Analysis) at a prevalence of 0.3 sorted by PPV. This means that—at least 30% of patients admitted to an intensive care unit for longer than 24 hours will develop sepsis, as judged by changes in concentration of the analyte shown in the first column. The second set of data is LDA (Linear Discriminant Analysis) at a prevalence of 0.3. LDA is another method of statistical analysis. QDA and LDA analysis methods are described in [1] Krzanowski, W. J., Principles of Multivariate Analysis, Oxford University Press, Oxford, 1988; and [2] Seber, G. A. F., Multivariate Observations, Wiley, New York, 1984.

FIG. 4. Tables of alternative names (aliases) for analytes are shown segregated by array.

FIG. 5A-5E. SlideMapName Proteomics for sepsis.

FIG. 6A-6E. SlideMapName Proteomics for mortality.

DETAILED DESCRIPTION OF THE INVENTION

The present invention is based on rigorous statistical analyses. Statistical terms which can be used to describe the methods and assays include:

diagnostic sensitivity=# of true positives (with Sepsis)/# of true positives+# of false negatives (Diagnostic sensitivity is the probability that an individual with the disease is screened positive.)

diagnostic specificity=# of true negatives (without Sepsis)/# of true negatives (with Sepsis)+# of false positives (Diagnostic specificity is the probability that an individual without the disease is screened negative.)

Positive Predictive Value=# of true positives/# of true positives+number of false positives (Positive Predictive Value or PPV is the probability that an individual with a positive screening result has the disease.)

Negative Predictive Value=# of true negatives/# of true negatives+# of false negatives (Negative Predictive Value or NPV is the probability that an individual with a negative screening result does not have the disease.)

The Cut-Off value is the value for a standard, or control sample (No Sepsis). Higher values indicate elevation and lower values indicate depression; both can be diagnostic of a septic sample.

Sepsis is a very heterogeneous affliction. When looking at single analytes in a small number of patients differences in profile can sometimes be observed. According to this invention, differences in profile can be overcome by coordinated analysis of data from a plurality of analytes, rather than from single analytes. Thus, samples can optionally be scored on the basis of the concentrations of several analytes grouped together and weighted using some statistical measure which provides for greater statistical power and improved prediction rate over methods employing single analytes. For example, data from two, three, four, or more analytes are grouped together and analyzed in combination. This type of analysis, termed multivariate analysis, is known to those of skill in the art. In yet another aspect, this invention features a multivariate classifier that weights each analyte in the group optimally. The multivariate classifier takes into account the relative contribution or weighting of each of these analytes in the determination of diagnosis.

The Table shows diagnostic parameters determined by a sample multivariate analysis comprising 4 analytes.

| Sensitivity | Specificity | PPV(0.1) | PPV(0.23) | PPV(0.3) | Correct Prediction Rate |
|---|---|---|---|---|---|
| 1.00 | 0.98 | 0.86 | 0.94 | 0.96 | 0.99 |

Figure 1:
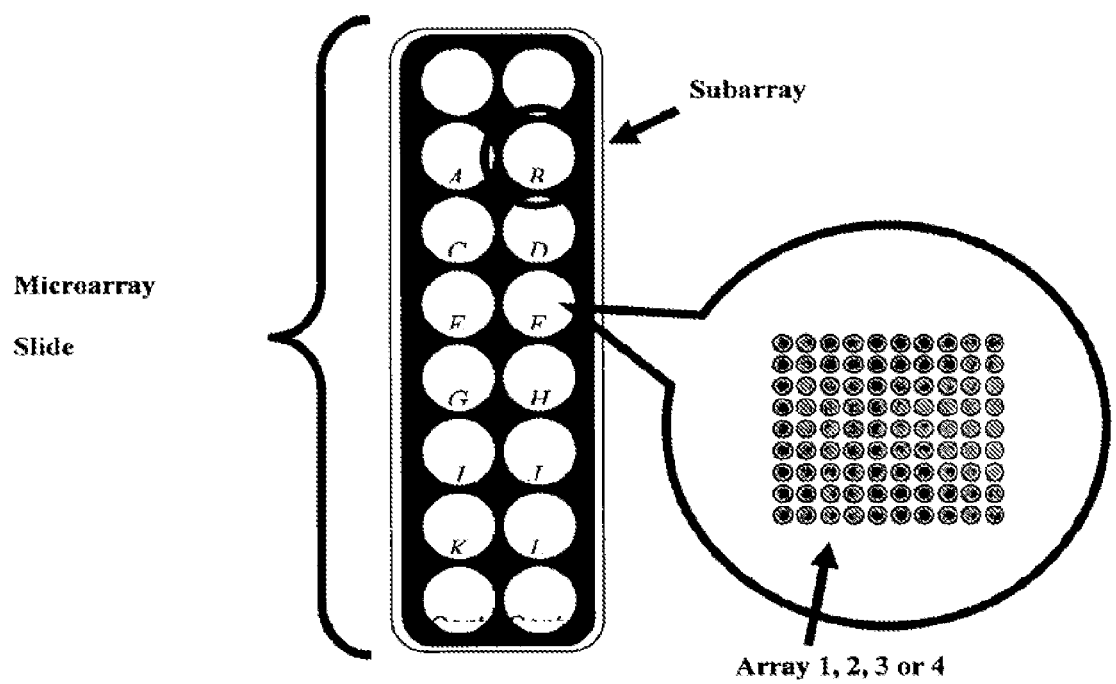
FIG. 1. Schematic representation of a sample protein microarray slide with 16 subarrays. Subarrays refer to the 16 wells, or circular analysis sites, on the slide. Array refers to the antibody content printed in a well. Each microarray slide contains only one type of array.
Figure 7:
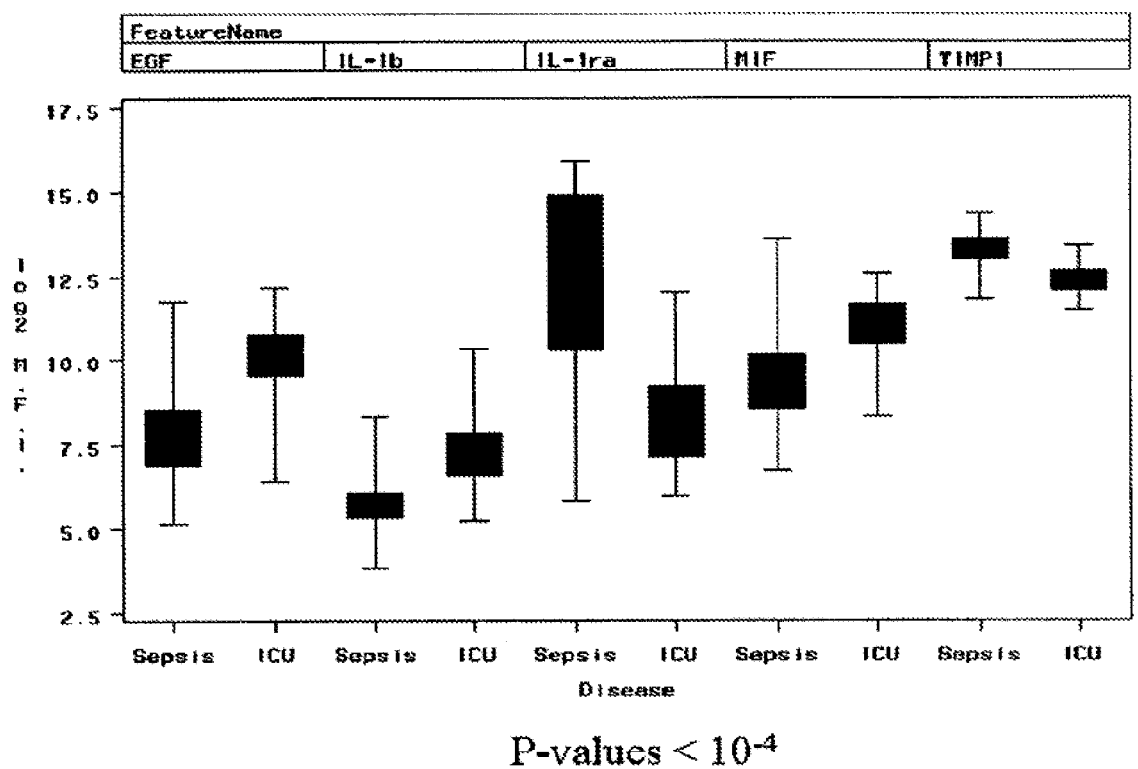
FIG. 7. A sample strategy for multivariate analysis is shown.
Figure 8:
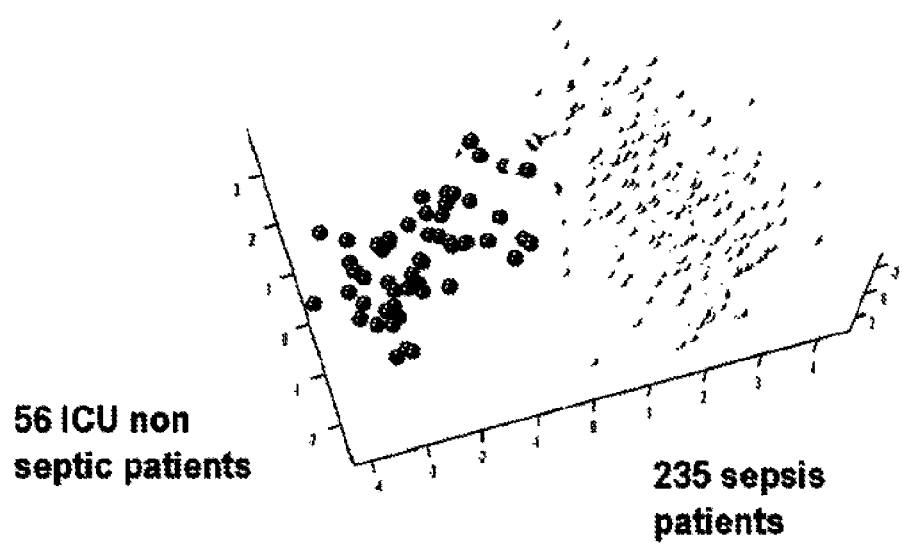
FIG. 8. Results from the sample strategy for multivariate analysis shown in FIG. 7.

For purposes of illustration only, and without limitation, a sample strategy for multivariate analysis is described below and sample results are shown in FIGS. 7 and 8.

Assuming that each group has a multivariate normal distribution, we develop a discriminant function or classification criterion using a measure of generalized squared distance. The classification criterion is based on the individual within-group covariance matrices; it also takes into account the prior probabilities of the classes. Each observation is placed in the class from which it has the smallest generalized squared distance. In addition we also compute the posterior probability of an observation belonging to each class.

The squared Mahalanobis distance from x to group t is $$d_t^2(x) = (x-m_t)'V_t^{-1}(x-m_t)$$

where $V_t = S_t$ where $S_t$ is the within-group t covariance matrice and $m_t$ is the 5-dimensional vector containing variable means in group t.

The group-specific density estimate at x from group t is then given by $$f_t(x) = (2\pi)^{-\frac{p}{2}} |V_t|^{-\frac{1}{2}} \exp(-0.5 d_t^2(x))$$

Using Bayes' theorem, the posterior probability of x belonging to group t is $$p(t \mid x) = \frac{q_i f_i(x)}{\sum_u q_u f_u(x)}$$

where the summation is over all groups.

The generalized squared distance from x to group t is defined as $$D_t^2(x) = d_t^2(x) + g_1(t) + g_2(t)$$

where $$g_1(t) = \ln |S_t|$$

and $$g_2 = -2 \ln(q_t)$$

where
$q_1$ is the prior probability of membership in group t
The posterior probability of x belonging to group t is then equal to $$p(t \mid x) = \frac{\exp(-0.5 D_t^2(x))}{\sum_u \exp(-0.5 D_u^2(x))}$$

The discriminant scores are $-0.5\, D_u^2(x)$. An observation is classified into group u if setting t=u produces the largest value of p(t|x) or the smallest value of $D_t^2(x)$.
Thus, $$D_{ICU}(x) = -0.6931 - 0.5 * (\Sigma(x - m_{icu}/S_{icu})^2 + 1.3270)$$

$$D_{sepsis}(x) = -0.6931 - 0.5 * (\Sigma(x - m_{sepsis}/S_{sepsis})^2 + 1.3270)$$

Where
$m_{icu} = [10.0691\ 8.3308\ 10.9416\ 12.3883\ 7.0395]$
$S_{isu} =$

| | | | | |
|---|---|---|---|---|
| −1.1888 | −0.5591 | −0.6561 | −0.0219 | −0.2616 |
| 0 | 1.2814 | 0.2723 | 0.0944 | 0.0139 |
| 0 | 0 | 0.6571 | −0.1357 | 0.4831 |
| 0 | 0 | 0 | −0.3875 | −0.0323 |
| 0 | 0 | 0 | 0 | 1.3280 |

And
$m_{sepsis} = [7.8059\ 12.4309\ 9.4300\ 13.2902\ 5.5798]$
$S_{sepsis} =$

| | | | | |
|---|---|---|---|---|
| 1.1977 | −0.3291 | 0.0043 | 0.1090 | −0.1464 |
| 0 | −2.6251 | −0.4601 | 0.0202 | −0.1352 |
| 0 | 0 | 1.1665 | 0.0734 | −0.1312 |
| 0 | 0 | 0 | 0.4051 | 0.0419 |
| 0 | 0 | 0 | 0 | −0.9892 |

Further, as shown in FIG. 7, samples can be grouped into septic or otherwise based on p-values alone using any of five different analytes. However, due to heterogeneity (error-bars), the strength of the diagnosis of individual samples may be weakened. Multivariate analysis of the same data using four analytes now makes it possible to diagnose individual samples with greater certitude (FIG. 8).

Those of skill in the art will be aware of several alternate methods to create a multivariate classifier that weights each analyte in the group optimally. Without limitation, these methods include supervised and unsupervised methods, including neural networks, self organizing maps, vector machine, perceptrons, clustering, multiple regression analysis, multiple linear discriminant analysis, principal component analysis and others as taught in Pattern Classification (2nd Edition) by Richard O. Duda, Peter E. Hart, David G. Stork ISBN: 0471056693. Each such multivariate classifier takes into account the relative contribution or weighting of each of these analytes in the determination of diagnosis.

Protein analytes can be detected in a sample by any means known in the art. Any immunological detection method known in the art can be used. Solid phase immunoassays are particularly useful for this purpose. Methods that apply the power of nucleic acid signal amplification to the detection of non-nucleic acid analytes can be employed for detecting, determining, and quantitating specific analytes in samples. See U.S. Pat. No. 6,531,283 which is incorporated herein by reference.

Multiple proteins can be analyzed, for example, by sandwich immunoassays on microarrays to which primary antibodies specific to the various proteins have been immobilized. First, the proteins or analytes, if present in the sample, are captured on the cognate spots on the array by incubation of the sample with the microarray under conditions favoring specific antigen-antibody interactions. Second, a rolling circle amplification (RCA) primer is associated with the various analytes using a secondary antibody that is specific for the analyte being detected and which is conjugated to the RCA primer or a hapten. In direct immunoassays, the secondary antibody is conjugated directly to the RCA primer. In indirect immunoassays, the secondary antibody is conjugated to a hapten, such as biotin and then incubated with a detector antibody conjugate or streptavidin conjugated with the RCA primer. Rolling circle replication primed by the primers results in production of a large amount of DNA at the site in the array where the proteins are immobilized. The amplified DNA serves as a readily detectable signal for the proteins.

Different proteins in the array can be distinguished in several ways. For example, the location of the amplified DNA can indicate the protein involved, if different proteins are immobilized at pre-determined locations in the array. Alternatively, each different protein can be associated with a different rolling circle replication primer that in turn primes rolling circle replication of a different DNA circle. The result is distinctive amplified DNA for each different protein. The different amplified DNAs can be distinguished using any suitable sequence-based nucleic acid detection technique. Comparison of proteins or analytes found in two or more different samples can be performed using any means known in the art. For example, a first sample can be analyzed in one array and a second sample analyzed in a second array that is a replica of the first array. The intensity of a spot for each analyte at the first array can be compared with the intensity of the corresponding spot of the second array. The differences in the intensities of the spot between the first and second array determine if the concentration of the analyte is different in the two samples. If differences exist, they are recorded as elevated analyte or depressed analyte. Alternatively, the same analyte(s) from different samples can be associated with different primers which prime replication of different DNA circles to produce different amplified DNAs. In this manner, each of many analytes present in several samples can be quantitated.

A variety of different solid phase substrates can be used to quantitate or determine the concentration of an analyte. The choice of substrate can be readily made by the routineer, based on convenience, cost, skill, or other considerations. Useful substrates include, without limitation: beads, bottles, surfaces, substrates, fibers, wires, framed structures, tubes, filaments, plates, sheets, and wells. These substrates can be made from: polystyrene, polypropylene, polycarbonate, glass, plastic, metal, alloy, cellulose, cellulose derivatives, nylon, coated surfaces, acrylamide or its derivatives and polymers thereof, agarose, or latex, or combinations thereof. This list is illustrative rather than exhaustive.

Other methods of protein detection and measurement described in the art can be used as well. For example, a single antibody can be coupled to beads or to a well in a microwell plate, and quantitated by immunoassay. In this assay format, a single analyte can be detected in each assay. The assays can be repeated with antibodies to many analytes to arrive at essentially the same results as can be achieved using the methods of this invention. Bead assays can be multiplexed by employing a plurality of beads, each of which is uniquely labeled in some manner. For example each type of bead can contain a pre-selected amount of a fluorophore. Types of beads can be distinguished by determining the amount of fluorescence (and/or wavelength) emitted by a bead. Such fluorescently labeled beads are commercially available from Luminex Corporation (Austin, Tex.) and permit up to 100 analyte measurements simultaneously.

Proteins and other analytes can alternatively be measured by enzyme-linked immunosorbent assay (ELISA), which permits a single protein measurement per microwell, and can be scaled up to 384 or more measurements per plate. Non-immunological assays can also be used. Enzyme activity-based assays can achieve a high degree of sensitivity and can be used. Specific binding protein assays can be used where a protein is a member of a specific binding pair that has a high binding affinity (low dissociation constant). The other member of the specific binding pair may be a protein or a non-protein, such as a nucleic acid sequence which is specifically bound by a protein.

Samples for testing according to the invention can be derived from any readily available patient material. Typically this will be blood, serum, or plasma. Other body samples can be used as well, including urine, sputum, tears, saliva, cerebrospinal fluid, pleural fluid, or peritoneal fluid. Body samples can be fractionated prior to testing to improve sensitivity and reduce background. Any fractionation procedure known in the art can be used, so long as the desired analyte remains in the fraction which is used as a test sample.

Some analytes may be informative of sepsis or patient condition when considered in isolation. However, more typically a plurality of analytes will be tested and considered in determining a diagnosis. Two, three, four, five, or six analytes may be considered. In the determination of diagnosis, the contribution of each of these analytes may be weighted. In some cases a larger number of analytes may be tested, but only a subset may be sufficient to provide a diagnosis. It may be desirable in order to gain increased statistical power, to test even larger number of analytes, such as at least 10, 12, 14, or 16 analytes. It may also be desirable to utilize both one or more analytes which are elevated and one or more analytes which are depressed in the same assay.

Control samples can be derived from a healthy individual or individuals, or from an individual or individuals who are ill but who do not have sepsis. Patients who are ill can be critically ill, such as patients in the intensive care unit. These samples can be assayed individually or in pools. The data from individual controls can be pooled to provide a range of "normal" values, also known as a reference range. The data can be obtained at an earlier time. Thus controls need not be run in a side-by-side fashion with test samples. For some purposes, samples from a single individual taken at different times are compared to each other. In such cases there need not be, but may be, any control or normal sample evaluated. Control samples can also be synthetically produced, by mixing known quantities of particular analytes, either in an artificial or a natural body sample fluid.

Analytes can be tested directly, or derivatives of the analytes can be tested. The derivatives can be forms of the analyte which occur in the body, or forms which are produced, either spontaneously or by design, during sample processing. Examples of derivatives include proteolytic degradation products, phosphorylated products, acetylated products, myristoylated products, transaminated products, protein complexed products, and complex dissociated products. These are collectively termed "metabolites."

The inventors have developed tests that permit the early detection, risk assessment, and monitoring of patients who have or are susceptible to sepsis. The tests are based on the identification of biomarkers whose regulation is perturbed in septic patients. Concentrations of some of the biomarkers are elevated in sepsis and concentrations of others are depressed.

The above disclosure generally describes the present invention. All references disclosed herein are expressly incorporated by reference. A more complete understanding can be obtained by reference to the following specific examples which are provided herein for purposes of illustration only, and are not intended to limit the scope of the claimed invention.

EXAMPLE 1

Materials and Methods for the Experimental Results Described in Example 2

Microarray Manufacture

Glass slides were cleaned and derivatized with 3-cyanopropyltriethoxysilane. The slides were equipped with a Teflon mask, which divided the slide into sixteen 0.65 cm diameter wells or circular analysis sites called subarrays. Printing was accomplished with a Perkin-Elmer SpotArray Enterprise non-contact arrayer equipped with piezoelectric tips, which dispense a droplet (~350 pL) for each microarray spot. Antibodies were applied at a concentration of 0.5 mg/mL at defined positions.

Each chip was printed with sixteen copies of one type of array, either Array 1.1.1, 2.1.1, 3.1.1, or 4.1. A set of cytokines was printed with quadruplicate spots in each subarray. After printing, chips were inspected using light microscopy. If the percentage of missing spots observed was greater than 5%, then the batch failed and the slides were discarded immediately. For all print runs described herein, 100% of the antibody features and >95% of the biotin calibrators were printed. Microarray chips were validated in concert with a set of qualified reagents in two ways: First, mixtures of 1-3 different cytokines were prepared so as to provide a high intensity signal and applied to 14 wells of a chip (with each well being treated with a different mixture up to the total complement of detector antibodies) and two arrays were used as blank controls. The chips were developed and scanned and the resulting signals were compared to the positional map of the particular array. Second, a titration QC for all analytes of a specified array using known sample matrices was performed. Normal human serum and heparinized plasma were assayed neat or spiked with purified recombinant cytokines representing all analytes in the array. Spiked mixtures were then titrated down the subarrays of a slide from 9,000 pg/ml to 37 pg/mL of spiked cytokine concentrations along with two subarrays for each un-spiked control sample. The data was quantified and for every analyte in the array a titration curve was generated to examine feature intensity behavior as a function of concentration. Taken together, this data was used to confirm the activity of array features and reagent sets.

Samples

A total of 48 clinical samples were provided: 24 samples of 0.5 mL serum and 24 samples of 1 mL citrate plasma from 6 patients selected from the PROWESS trial, with 4 time points per patient (preinfusion, days 1, 4 and 7). These patients were not chosen on the basis of baseline disease severity. There were 2 groups (drug treated survivors and placebo treated survivors), 3 patients per group. The researchers were not blinded to sample identity.

In addition to these 48 clinical samples, 8 serum samples and 8 citrate plasma samples from individuals presumed healthy were purchased from Biological Specialty Corporation (Colmar, Pa.) to serve as normal controls.

Clinical serum and plasma samples were received on Mar. 19, 2003, thawed, centrifuged to remove particulate matter (15 min at 10,000×g for citrate plasma, and 15 min at 1300×g for other samples). The resulting supernatants were collected, divided into 5 aliquots (one for each array) and re-frozen at −80° C. Prior to testing, samples were thawed, Immunoglobulin Inhibiting Reagent (IIR, Bioreclamation Inc) was added to a final concentration 0.25 mg/mL, Heteroblock (Omega Biologicals) was added to samples at a concentration of 0.25 mg/mL, and Tween 20 was added to final concentration of 0.1%.

RCA Immunoassay

Prior to assay, the slides were removed from storage at room temperature in sealed containers and opened in a humidity controlled chamber (45-55%). Slides were blocked with Seablock (Pierce Chemical Co.), diluted 1:1 with PBS for 1 h at 37° C. in a humidified chamber. Following removal of the blocking solution, they were washed twice with 1×PBS/0.5% Brij 35 prior to application of sample. On each slide, control serum (Jackson Immuno Research Laboratories) was applied to two subarrays, and a negative control with PBS buffer applied to two subarrays. The test samples were assayed on the remaining 12 subarrays. Twenty µL of the treated sample were then applied to each subarray. The basics of performing immunoassays with RCA signal amplification has been described (*Nat. Biotechol.* (2002) 20:359-65) and we are using SOPs dervyed from the protocols used in that study. Slides were scanned (GenePix 4000B, Axon Instruments Inc.) at 10 µm resolution with a laser setting of 100% and a PMT setting of 550 V. Mean pixel fluorescence values were quantified using the fixed circle method in GenePix Pro 4.0 (Axon Instruments). The fluorescence intensity of microarray spots was analyzed for each feature and sample, and the resulting mean intensity values were determined. Dose-response curves for selected cytokines were examined, ensuring that feature intensity is above background and exhibiting increasing intensity with increasing analyte concentration.

EXAMPLE 2

Candidate Biomarkers for Sepsis

Analyte levels from sepsis patients were compared with normal individuals to identify candidate biomarkers for sepsis. Candidate biomarkers for sepsis were posited to be manifest as a difference in blood analyte levels between time zero sepsis patients and normal controls and that trended toward the normal control value at day 7 in the surviving sepsis patients, in whom sepsis was presumably resolving. For ease of comparison, data were plotted 4 different ways for both serum and citrate plasma samples.

Of 107 analytes analyzed, six (6%) exhibited interesting differences between the sepsis patients at time zero and normal controls, and that decreased over time, including IL-8, IL-6, IL2sRα, MMP-7, MIPF-1 and IGFBP-1. A brief description for each of the analyte is provided below.

Since the value of correlation coefficient is very sensitive to outliers and multimode distributions of data, our interpretation is very conservative.

IL-8: IL-8 levels were higher in sepsis patients relative to normal controls at the pre-infusion time point, in both the plasma and serum samples. The level of IL-8 in sepsis patients declined to match levels in normal controls by day 7. Correlation analysis revealed significant correlation (correlation coefficient>0.8) between the serum IL-8 level in the sepsis group with each of MIP3β, IL-6, MCP-2, MCP-1, BLC (Table 1). Significant correlation was also observed between plasma IL-8 level and each of MCP-2, BLC, IL-2sRα, IL-6 in the citrate plasma samples (Table 1).

IL-6: Similar to IL-8, IL-6 levels were also higher in sepsis patients relative to normal controls at the pre-infusion time point, in both plasma and serum samples and levels declined to reach normal control levels by day 7. Correlation analysis revealed significant correlation (correlation coefficient>0.8) between the serum IL-6 level in the sepsis group with each of MIP-3β, MCP-1, IL-8 (Table 1). Significant correlation was also observed between plasma IL-6 level and each of MIP-3β, MCP-1, IL-8 in the citrate plasma samples (Table 1).

IL-2sRα: Sepsis patients showed higher levels of IL-2sRα relative to the normal controls in both serum and plasma at all time-points (pre-infusion, days 1, 4 and 7). Although IL-2sRα levels declined in the sepsis patients with time, they still remained higher that the levels observed in normal controls at day 7. Correlation analysis revealed significant correlation (correlation coefficient>0.8) between the serum IL-2sRα level in the sepsis group with each of RANK, MMP-7, MIP-3β, DR6 (Table 1). Significant correlation was also observed between plasma IL-2sRα level and each of IL-8, MCP-1, MCP-2, BLC, HVEM in the citrate plasma samples (Table 1).

MMP-7: Serum and plasma levels of MMP-7 levels were higher in sepsis patients at all time-points examined. Interestingly, MMP-7 levels remained fairly stable as time progressed. Examination of the sepsis patients revealed considerable individual variation. Correlation analysis revealed significant correlation (correlation coefficient>0.8) between the serum MMP-7 level in the sepsis group with each of IL-2sRα, RANK, HVEM, DR6 (Table 1). Significant correlation was also observed between plasma MMP-7 level and HVEM in the citrate plasma samples (Table 1).

MPIF-1: MPIF-1 levels were higher in the sepsis patients relative to the normal controls in both serum and plasma, at all time-points examined. As time progressed, levels of MP1F-1 declined in the sepsis groups to the levels observed in the normal controls. Correlation analysis did not reveal any significant correlation (correlation coefficient>0.8) between the serum MP1F-1 level and other analytes in the sepsis group in both serum and citrate plasma samples.

IGFBP-1: IGFBP-1 levels were higher in sepsis patients relative to the normal controls levels in both serum and plasma, at all the time-points examined. As time progressed, levels of IGFBP-1 declined in the sepsis groups but not to the levels observed in the normal controls. As with MMP-7, sepsis patients exhibited considerable individual variation.

Correlation analysis did not reveal any significant correlation (correlation coefficient>0.8) between the serum IGFBP-1 level and other analytes in the sepsis group in both serum and citrate plasma samples.

TABLE 1

Analytes that show correlation to IL-8, IL-6, IL2sRα, MMP-7, MIPF-1 and IGFBP-1 in either serum or citrate plasma samples.

| Sample Type | Analyte#1 | Analyte #2 | Correlation Coefficient |
|---|---|---|---|
| Serum | IL-8 | MIP3β | 0.90887 |
| | | IL-6 | 0.87024 |
| | | MCP-2 | 0.8397 |
| | | MCP-1 | 0.83788 |
| | | BLC | 0.8198 |
| | IL-6 | MIP3β | 0.92821 |
| | | MCP-1 | 0.88214 |
| | | IL-8 | 0.87024 |
| | IL-2sRα | RANK | 0.87464 |
| | | MMP7 | 0.84191 |
| | | MIP3β | 0.80768 |
| | | DR6 | 0.80667 |
| | MMP-7 | IL-2sRa | 0.84191 |
| | | RANK | 0.83404 |
| | | HVEM | 0.82405 |
| | | DR6 | 0.80013 |
| Plasma | IL-8 | MCP-2 | 0.90452 |
| | | BLC | 0.89497 |
| | | IL-2sRa | 0.84953 |
| | | IL-6 | 0.82152 |
| | IL-6 | MIP3β | 0.89956 |
| | | IL-8 | 0.82152 |
| | | MCP-1 | 0.81609 |
| | IL-2sRα | IL-8 | 0.84953 |
| | | MCP-1 | 0.83809 |
| | | MCP-2 | 0.8159 |
| | | BLC | 0.81149 |
| | | HVEM | 0.80799 |
| | MMP-7 | HVEM | 0.84646 |

Analytes with Differential Expression Levels in Sepsis Vs. Normal Controls

When sepsis samples were compared to normal serum at pre-infusion time-point, there were significant differences in the levels of several analytes (e.g., IL-8, IL-6, IL2sRα, MMP-7, MIPF-1 and IGFBP-1). Some of the observed changes in their levels were supported by the literature.

IL-6 (Interleukin-6) and IL-8 (Interleukin-8)

It is well known that the levels of IL-6 and IL-8 are increased in sepsis. In the present study, these cytokines were found to be elevated in sepsis samples at the pre-infusion time-point (compared to normal controls), and to gradually decrease with time, approaching normal levels at day 7. IL-6 and IL-8 are important pro-inflammatory cytokines that contribute to organ dysfunction in sepsis (Scand J Immunol 1998 48:509-14; Res Commun Chem Pathol Pharmacol 1994 84:291-300). Levels of IL-6 and IL-8 have also been shown to be associated with the severity and mortality of the disease (Eur J Haematol 1993 50:243-9; Nippon Geka Gakkai Zasshi 1996 97:1054-9). Therefore the high initial levels and reduction of IL-6 and IL-8 levels with time, observed in the present study, is in close agreement with the pro-inflammatory role of these cytokines described in the literature.

MMP-7 (Matrix Metalloproteinase 7)

Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. MMP-7 activity is upregulated in liver metastases of colorectal cancer (Clin Cancer Res 2002 8:144-8). Studies in mice suggest that MMP-7 regulates the activity of defensins in intestinal mucosa. Defensins represent an important component of host response to infection. No literature reports describing a direct association between MMP-7 levels and sepsis were found in the literature. However, other members of the MMP family of proteins have been shown to play a role in sepsis, e.g., MMP-9 (see MMP-9 discussion in next section).

IGFBP-1 (Insulin-like Growth Factor Binding Protein 1)

Insulin-like growth factors I and II (IGF-I and -II) play an active role in cell proliferation. In biological fluids, they are non-covalently bound to high-affinity binding proteins (IGFBPs), at least 6 species of which have been identified (Int J Cancer 1998 77:874-9). IGFBPs form high-affinity complexes with IGF-I and thereby either inhibit or potentiate its mitogenic and metabolic effects (Biochemistry 1999 38:6386-96). IGFBP-1 is a 28-kDa plasma protein that binds to IGF-I and IGF-II with high affinity (Endocrinology 2000 141:3156-64) and has been shown to inhibit or stimulate cellular responses to IGF in vitro (J Biol Chem 2001 276: 8740-5). IGFBP-1 was elevated in the blood as a result of sepsis (Endocrinology 2000 141:3156-64) and might, in part, be responsible for the observed wasting. IGFBP-1 is present at relatively low concentration in serum but its levels fluctuate acutely, suggesting regulation of IGF bioactivity in response to short-term metabolic changes. End organ failure, particularly of liver and kidney, significantly affects production and clearance rates of the circulating IGFBPs and may contribute to the catabolism frequently seen in these states and in chronic sepsis (Baillieres Clin Endocrinol Metab 1996 10:421-46). The liver is the principal site of IGFBP-1 synthesis, and it has been shown that pro-inflammatory cytokines can directly stimulate IGFBP-1 secretion in a human hepatoma cell line (Endocrinology 2000 141:3156-64). In mice, IL-1 alpha and TNF alpha regulate IGFBP-1 serum levels and hepatic mRNA abundance in vivo and in vitro (Horm Metab Res 1999 31:209-15). The increase in IGFBP-1 observed in sepsis may be also reproduced in vivo by IL-1β, TNF-α and dexamethasone, and in vitro by IL-1β, IL-6, and dexamethasone (Endocrinology 2001 142: 241-248). An early, short-lasting increase in IGFBP-1 (188.8+/−39% P<0.05, 3 h after LPS) was observed in sheep in response to endotoxin challenge, while no significant change was seen for either IGFBP-2, -3 or -4 (J Endocrinol 2000 164:361-9). After caecal ligation and puncture in rats, there was a reduction in both circulating and hepatic IGF-I mRNA levels associated with a specific and differential regulation of hepatic IGFBP-1, -2 and -3 mRNA levels (J Endocrinol 1996 151:287-92). IGFBP-1 was increased in the blood, liver, and muscle of septic rats (Am J Physiol 1996 270:E430-7). Critically ill, septic patients have high levels of IGFBP-1 (Horm Res 1993 40:87-91), which is in agreement with the results observed in the present study. Significant differences were found between nonsurvivors and survivors in the levels of IGFBP-1 (44.3 vs. 8.9 nmol/L) in children with meningococcal sepsis and the pediatric risk of mortality score correlated significantly with levels of IGFBP-1 (J Clin Endocrinol Metab 2002 87:3118-24).

IL-2sRα (Interleukin 2 Soluble Receptor Alpha)

The biological activity of IL-2 is mediated by binding to a high affinity receptor complex composed of IL-2 Rα, β, and γ. Alone, IL-2 Rα binds IL-2 with low affinity, but is unable to transduce a signal. A soluble form of IL-2 Rα appears in serum, concomitant with its increased expression on cells (Immunol Today 1993 14:264-70, FASEB J 1991 5:2567-74, Hybridoma 1985 4:91-102). The function of IL-2 Rα is unclear, since it would be expected to be a poor inhibitor of IL-2 because of its low binding affinity. In any case, increased levels of soluble EL-2 Rα in biological fluids reportedly correlate with increased T cell, B cell and immune system activation.

Elevated level of sIL-2R has been observed in sepsis patients in multiple studies (Br J Surg 2000 87:223-30, Intensive Care Med 1999 25:1402-6, J Infect Dis 1991 163:1145-8). An increase of soluble IL-2 receptor level was also observed in patients with systemic inflammatory response syndrome (Thromb Res 1999 95:205-13). Furthermore, the level of sIL-2 receptor was found to be higher in non-surviving patients with septic shock than in surviving patients (J Infect 1998 37:241-7, Ann Clin Lab Sci 1996 26:426-32). The concentration of sIL-2R was found to have predictive value for identifying patients with gram-negative sepsis at risk for progression toward the syndrome of septic shock (J Crit. Care 1995 10:64-71). High concentrations of IL-6, IL-8 and sIL-2R predict organ failure in patients with community-acquired septic shock, and the combination of these markers may provide the means to identify sepsis patients who will develop organ failure (Clin Sci 1999 97:529-38). Furthermore, a study suggests that soluble interleukin-2 receptor levels can be used to facilitate the diagnosis of sepsis in premature infants where sepsis diagnosis is difficult because newborn infants often suffer from bacterial and viral infections without presenting typical symptoms (J Pediatr 1995 126:982-5). Therefore literature reports corroborate the increase of sIL-2R levels observed in the present study.

MPIF-1 (Myeloid Progenitor Inhibitory Factor 1)

MPIF-1 is a member of the CC cytokine family that displays chemotactic activity on resting T lymphocytes and monocytes, and a minimal but significant activity on neutrophils. This cytokine is also a potent suppressor of bone marrow low proliferative potential colony-forming cells, a committed progenitor that gives rise to granulocyte and monocyte lineages (J Exp Med 1997 185:1163-72). The MPIF-1 signal transduction pathway appears to include binding to CCR1, transduction by G proteins, effector function by phospholipase C, protein kinase C, calcium flux, PLA2, and cytoskeletal remodeling (J Immunol 1999 162:435-44). No literature reports describing a direct association between MPIF-1 levels and sepsis were found in the literature.

In summary, changes in the levels of some cytokines observed in the present study between sepsis patients and normal controls are in agreement with findings reported in the literature.

EXAMPLE 3

Materials and Methods for Results Described in Example 4

Microarray Manufacture

Glass slides were cleaned and derivatized with 3-cyanopropyltriethoxysilane. The slides were equipped with a Teflon mask, which divided the slide into sixteen 0.65 cm diameter wells or circular analysis sites caned subarrays. Printing was accomplished with a Perkin-Elmer SpotArray Enterprise non-contact arrayer equipped with piezoelectric tips, which dispense a droplet (~350 pL) for each microarray spot. Antibodies were applied at a concentration of 0.5 mg/mL at defined positions.

Each chip was printed with sixteen copies of one type of array, i.e. Array 5. A set of cytokines was printed with quadruplicate spots in each subarray. After printing, chips were inspected using light microscopy. If the percentage of missing spots observed was greater than 5%, then the batch failed and the slides were discarded immediately. For all print runs described herein, 100% of the antibody features and >95% of the biotin calibrators were printed. Microarray chips were validated in concert with a set of qualified reagents in two ways: First, mixtures of 1-3 different cytokines were prepared so as to provide a high intensity signal and applied to 14 wells of a chip (with each well being treated with a different mixture up to the total complement of detector antibodies) and two arrays were used as blank controls. The chips were developed and scanned and the resulting signals were compared to the positional map of the particular array. Second, a titration QC for all analytes of a specified array using known sample matrices was performed. Normal human serum and heparinized plasma were assayed neat or spiked with purified recombinant cytokines representing all analytes in the array. Spiked mixtures were then titrated down the subarrays of a slide from 9,000 pg/ml to 37 pg/mL of spiked cytokine concentrations along with two subarrays for each un-spiked control sample. The data was quantified and for every analyte in the array a titration curve was generated to examine feature intensity behavior as a function of concentration. Taken together, this data was used to confirm the activity of array features and reagent sets.

Samples

A total of 48 clinical samples were provided: 24 samples of 0.5 mL serum and 24 samples of 1 mL citrate plasma from 6 patients selected from the PROWESS trial, with 4 time points per patient (preinfusion, days 1, 4 and 7). These patients were not chosen on the basis of baseline disease severity. There were 2 groups (drug treated survivors and placebo treated survivors), 3 patients per group. The researchers were not blinded to sample identity.

In addition to clinical samples, 8 serum samples and 8 citrate plasma samples from individuals presumed healthy were purchased from Biological Specialty Corporation (Colmar, Pa.) to serve as normal controls.

Clinical serum and plasma samples were thawed, centrifuged to remove particulate matter (15 min at 10,000×g for citrate plasma, and 15 min at 1300×g for other samples). The resulting supernatants were collected, divided into 5 aliquots (one for each array) and re-frozen at −80° C. Prior to testing, samples were thawed, Immunoglobulin Inhibiting Reagent (IIR, Bioreclamation Inc) was added to a final concentration 0.25 mg/mL, Heteroblock (Omega Biologicals) was added to samples at a concentration of 0.25 mg/mL, and Tween 20 was added to final concentration of 0.1%.

RCA Immunoassay

Prior to assay, the slides were removed from storage at room temperature in sealed containers and opened in a humidity-controlled chamber (45-55%). Slides were blocked with Seablock (Pierce Chemical Co.), diluted 1:1 with PBS for 1 h at 37° C. in a humidified chamber. Following removal of the blocking solution, they were washed twice with 1×PBS/0.5% Brij 35 prior to application of sample. On each slide, control serum (Jackson Immuno Research Laboratories) was applied to two subarrays, and a negative control with PBS buffer applied to two subarrays. The test samples were assayed on the remaining 12 subarrays. Twenty μL of the treated sample were then applied to each subarray. The basics of performing immunoassays with RCA signal amplification has been described (*Nat. Biotechol.* (2002) 20:359-65) and we are using SOPs derived from the protocols used in that study. Slides were scanned (GenePix 4000B, Axon Instruments Inc.) at 10 μm resolution with a laser setting of 100% and a PMT setting of 550 V. Mean pixel fluorescence values were quantified using the fixed circle method in GenePix Pro 4.0 (Axon Instruments). The fluorescence intensity of microarray spots was analyzed for each feature and sample, and the resulting mean intensity values were determined. Dose-response curves for selected cytokines were examined, ensuring that feature intensity is above background and exhibiting increasing intensity with increasing analyte concentration.

EXAMPLE 4

Candidate Biomarkers for Sepsis

Analyte levels from the 6 sepsis patients were compared with normal individuals to identify candidate biomarkers for sepsis. Biomarkers for sepsis were identified based on analyte differences observed between sepsis and normal at time zero.

Coagulation markers: Several of the analytes measured on array 5 are of potential relevance to the anticoagulation. They include protein C (the precursor of activated protein C), protein S (which acts in combination with protein C to inactivate Factor Va), D Dimer (which is a measure of intravascular coagulation), and CD141 (which binds thrombin and cleaves protein C to yield activated protein C). Analysis of D Dimer DD5 and DD6 in plasma and protein S in serum was complicated by grossly elevated values that required a sepsis sample dilution of 1:50 to bring values into the dynamic range of the assay. A difference was observed between the sepsis group and the normal controls in serum values of D Dimer DD5 and DD6, but this finding is of uncertain significance since determination of D Dimer in serum lacks clinical meaning [data not shown]. Protein C showed a small decrease in level in sepsis patient sera, but no difference in sepsis plasma. The only coagulation marker to exhibit a clear difference between the groups was CD141, which was increased in serum of septic patients at all time points. Unlike sepsis biomarker candidates identified in the previous study, CD141 did not trend toward normal values by day 7 in sepsis-surviving patients, when sepsis was presumably resolving, indicating CD141 to represent a more chronic index of sepsis or disease.

Other analytes exhibiting notable differences between sepsis patients and normal controls included MIF, MMP-8, IL-18, AgRP, and CRP. A brief description of each profile is provided below.

AgRP, MMP8, IL18, MIF: AgRP, MMP8, MIF and IL18 levels were higher in sepsis patients than in normal controls in both plasma and serum samples. The differences were more pronounced in serum than in plasma, and observed at all time points. MMP8 showed the greatest magnitude of difference between sepsis and normal controls (~25-fold). In fact, this difference was even greater than measurable in neat samples since many sepsis sample values for MMP8 were saturated. It should be noted that MMP9 exhibited a similar profile to MMP8.

CRP: CRP comparisons were complicated by the fact that levels were so high in sepsis patients that values were artefactually depressed in sepsis patients. A 1:625 dilution was necessary to bring CRP values within the dynamic range of the assay in sepsis samples whereas values were within the dynamic range in neat normal control samples (data not shown). It should be noted that 1:50 sample dilutions were run only with sepsis samples and only in singlicate in the pre-run in the present study. In longitudinal study 2, 1:50 sample dilutions will be performed for all samples and run in triplicate on array 5 to allow direct comparisons of CRP and other analytes at or near the upper limit of quantitation.

Correlation analysis revealed significant correlation (coefficient>0.8) between the serum or plasma levels of these analytes and other analytes in these samples. Since correlation coefficient values are very sensitive to outliers and multimode distributions of data, however, interpretation needs to be very conservative.

TABLE 2

Analytes correlating with AgRP, IL18, MMP8, MIF, CD141 & Protein C in serum & citrated plasma. Negative correlations indicate trends in the opposite directions.

| Index analyte | Plasma Correlate | | Serum Correlate | |
| --- | --- | --- | --- | --- |
| Protein C | NAP-2 | 0.85078 | | 0.52675 |
| | IGFBP-6 | 0.68619 | | 0.55952 |
| | Neut Blast | 0.68161 | | 0.73483 |
| | ProteinS | 0.57674 | | 0.52831 |
| | CD141 | 0.53515 | | 0.49269 |
| CD141 | IGFBP-3 | 0.77435 | | 0.62038 |
| | IL-1ra | 0.70672 | | 0.63177 |
| | MMP7 | 0.65748 | | 0.6273 |
| | AgRP | 0.69181 | | 0.58788 |
| | ALCAM | 0.7317 | DR6 | 0.62635 |
| | IGFBP-1 | 0.66008 | L Selectin | 0.61656 |
| AgRP | MMP7 | 0.87709 | | 0.8346 |
| | IL-2sRa | 0.80326 | | 0.71104 |
| | RANK | 0.72941 | | 0.72298 |
| | HVEM | 0.81839 | | 0.74574 |
| | I-309 | 0.73521 | | 0.66089 |
| | IGFBP-1 | 0.74057 | ENA-78 | -0.72375 |
| | IL-18 | 0.72091 | DR6 | 0.68636 |
| | MIG | 0.7056 | IL-1a | 0.64342 |
| | SCF R | -0.70543 | IL-7 | -0.6202 |
| MMP-8 | CRP | -0.89196 | | -0.71546 |
| | IL-10rb | -0.8444 | ENA-78 | -0.74543 |
| | GRO-g | 0.81551 | MMP7 | 0.7175 |
| | TRAIL R1 | 0.80501 | MIP-1d | 0.70679 |
| | FGF-4 | 0.79541 | IL-2sRa | 0.68527 |
| | GROb | 0.78096 | IL-18 | 0.61728 |
| | PDGF-Ra | 0.77071 | HCC1 | 0.60376 |
| | IL-1srII | 0.76559 | RANK | 0.5916 |
| | Lymphotactin | 0.74288 | HVEM | 0.56404 |
| MIF | MMP-8 | 0.72123 | D-Dimer | 0.74156 |
| | TIMP1 | 0.69271 | D-Dimer | 0.6582 |
| | TRAIL R4 | 0.66063 | D-Dimer | 0.63237 |
| | BDNF | 0.64952 | PAI-II | 0.59991 |
| | GRO-g | 0.63311 | LIF Ra | 0.59456 |
| | ICAM-1 | 0.63247 | IL-2 | 0.59085 |
| | MMP9 | 0.61095 | IL-17 | 0.58761 |
| IL-18 | HVEM | 0.8612 | | 0.88672 |
| | MMP7 | 0.79136 | | 0.80958 |
| | M-CSF | 0.75023 | | 0.80279 |
| | TNF-a | 0.72586 | | 0.71039 |
| | GCP-2 | 0.72236 | HCC1 | 0.82688 |
| | MIG | 0.72185 | IL-2sRa | 0.82065 |
| | AgRP | 0.72091 | RANK | 0.73954 |
| | CD27 | 0.71855 | ICAM3 | 0.72965 |
| | TNF-b | 0.71703 | 4-1BB | 0.72739 |

EXAMPLE 5

Analytes with Differential Expression Levels in Sepsis Vs. Normal Controls

When sepsis samples were compared to normal serum at pre-infusion time-point, there were significant differences in the levels of several analytes (e.g., CD141, AgRP, MMP-8, MIF, IL-18). Many of the observed changes in their levels were supported by the literature.

Coagulation markers: Array 5 measured several coagulation markers of potential relevance in sepsis. These include, protein C (precursor of activated Protein C), protein S (inactivates FactorVa), D-Dimer, and CD141. CD141 was the only coagulation marker that exhibited a clear difference between sepsis patients and normal controls.

CD141: CD141 also called thrombomodulin or fetomodulin belongs to C-type lectin family. It is a single chain, type I membrane glycoprotein (575 amino acids) with an approximately 500 amino acid extracellular region consisting of several domains, which include six EGF-like (epidermal growth factor) repeats which function in thrombin/protein C binding and a serine/threonine-rich region which is important for optimal anticoagulant function (Blood 1990 75:329). It is expressed on a number of cell types including endothelial cells, keratinocytes, megakaryocytes, platelets, monocytes, neutrophils, smooth muscle cells and synovial lining cells. CD141 is critical for the activation of protein C and initiation of the protein C anticoagulant effect. CD141 is a cofactor for the thrombin-mediated generation of APC (FASEB J 1995 9:946). APC then acts to degrade the cofactors Va and VIIIa on platelets and endothelial cells, thereby decreasing the production of thrombin, which is the central effector protease in clotting. Thrombin activates platelets, converts fibrinogen to fibrin and promotes fibrin cross-linking by activating factor XIII, leading to clot formation.

Elevated levels of CD141 have been reported in several studies on sepsis and sepsis-related organ failure (Am J Hematol, 199, 38:281-87; Surg Today, 1995, 25:585-90). In a study involving pediatric sepsis patients, CD141 levels were 1.5 to 3 times greater than healthy control patients (Crit. Care Med 1998, 25: 933-8). Mice carrying CD141 gene mutation, that disrupts the CD141-dependent activation of protein C, exhibit a hypercoagulable state and an increased susceptibility to thrombosis and sepsis (Arterioscler Thromb Vasc Biol 2001 September; 21(9):1531-7). There are also reports of people with mutation in the CD141 gene presenting with thromoembolic disease (Blood 1995 Jan. 15; 85(2):330-6). Therefore the elevated levels of CD141 observed in the present study in sepsis is in complete agreement with the literature.

Other analytes that exhibited differential expression between sepsis patients and normal controls:

AgRP: Agouti-Related Protein (AgRP), first identified by Ollman et al (Science 278: 135-138, 1997), is a potent antagonist of MC3-R (melanocortin-3 receptor) and MC4-R (melanocortin-4 receptor) and is an integral component in the metabolic processes that regulate feeding behavior and body weight. Present in the hypothalamus, AgRP levels are, elevated in obesity (Katsuki et al, 2001). The mature human protein is a single polypeptide chain of 112 amino acid residues, consisting of an N-terminal acidic region and a unique C-terminal cysteine-rich domain (Biochemistry 1998 Sep. 1; 37(35):12172-7). LPS has been shown to stimulate expression of pro-inflammatory cytokines, IL-1β, IL-6 and TNF-α in the hypthalamus and stimulate the hypothalamus-pituitary-adrenal (HPA) axis (Ann. N.Y. Acad. Sci., 2000, 917:169-74, Psychoneuroendocrinology, 2003, 28:481-500). It has been shown that mice deficient for corticotrophin releasing hormone (CTH), are unable to control systemic IL-6 levels in an induced inflammatory situation, suggesting the role of HPA regulating the inflammatory process (J. Clin. Invest., 2001, 108:1159-66). Alpha-MSH (alpha-melanocyte stimulating hormone) has been shown to attenuate the stimulatory effects of IL-1β on the HPA. AgRP is an alpha-MSH antagonist. In primate experiments, intracerebroventricular administration of AgRP along with IL-1β significantly enhanced ACTH (adrenocorticotropic hormone) levels over administration of IL-1β alone. ACTH is an important monitor of HPA activation. These studies suggest that, in addition to regulating appetite, AgRP may play a role in neuroendocrine regulation and specifically that AgRP may interact with alpha-MSH to modulate neuroendocrine responses to inflammation (Endocrinology 2003 144(5):1736-41). Despite its role in obesity, higher levels of AgRP have been seen in brain tissue of patients who died of prolonged illness than in obese subjects (J. Clin. Endocrinol. Metab., 2002, 87:927-37). In the present study, AgRP levels are consistently higher in sepsis patients as compared to non-septic controls. These sepsis patients are severely ill with very high levels of pro-inflammatory cytokines in their circulation (as shown in Phase I report). It is therefore reasonable to expect a significant influence of these pro-inflammatory cytokines on the HPA. Given the high levels of pro-inflammatory cytokines in these patients, the increased AgRP levels may reflect the loss of HPA-homeostasis in the sepsis patients associated with the severity of the disease. Interestingly, in this regard AgRP levels on day 4 and day 7 correlated well with day 0 APACHE II scores.

There is an increasing body of knowledge that neuroendocrine and immune systems communicate bi-directionally. This interface is mediated by cytokines acting as auto/paracrine or endocrine factors in regulating pituitary development, cell proliferation, hormone secretion and feed back control of HPA axis (Endocrinology, 2002 143:1571-4; Psychoneuroendocrinology, 2002, 26:761-88). It is interesting to note that three cytokine/hormones related to the HPA seem to be modulated in the present study namely, AgRP, Leptin (Stage I report) and Prolactin (see below).

MMP-8. MMP-8 is a member of the matrix metalloproteinase family, which are zinc and calcium dependent endopeptidases that function in the breakdown of extracellular matrix. It is stored as a latent proenzyme in specific granules of polymorphonuclear leukocytes. Matrix metalloproteinases are usually not expressed constitutively, and their expression is regulated by a variety of physiologic and pharmacologic signals, including cytokines and growth factors, bacterial endotoxin, phorbol esters, phagocytosable material, and hormones. Additionally, the activity of MMPs is regulated post-translationally through the activation of the proenzymes and the inhibition of active enzymes by endogenous inhibitors, α2-microglobulins and tissue inhibitors of metalloproteinases. What is the role of MMPs in sepsis? In early phase of endotoxinaemia or bacteraemia, the bone marrow is activated, which leads to leukocytosis. Neutrophils secrete a considerable amount of latent MMPs, including neutrophil procollagenase (MMP-8) and progelatinase B (MMP-9). It has been hypothesized that MMP-8 and MMP-9 may contribute to sepsis through the degradation of endothelial basement membranes, resulting in vascular leakage and shock (Acad Geneeskd Belg 2001; 63(6):531-8). Furthermore, in recent years, strong evidence has suggested a member of the MMP family to play a role in sepsis: plasma MMP-9 concentrations and monocyte MMP-9 mRNA levels were found be to significantly higher in non-surviving patients with septic shock than in surviving patients and normal controls (Am J Med Sci 1998 316:355-60) and MMP-9 deficient mice were resistant to endotoxin shock (Eur J Immunol 2002 32:2163-71). In rats MMP inhibitors have been shown to specifically suppress TNF-α secretion following LPS stimulation (Shock, 1997, 7:427) suggesting a possible role of MMP's in inflammatory response. Our observation that plasma and serum levels of MMP-8 were elevated in sepsis patients as compared to normal controls is in agreement with the literature, and, together with the differences in MMP-7 and MMP-9 in sepsis in the previous report, suggest an important role for this protein family in the pathophysiology of sepsis.

MIF: Macrophage migration inhibitory factor is a pleiotrophic cytokine secreted by macrophages, T cells and pituitary gland during inflammatory responses (Human Cytokines. Handbook for Basic and Clinical Research, p. 222-56; FASEB J. 199610:1607-13). It is a 147 amino acid, 15.6 Kd protein. MIF is a unique cytokine in that it can function as an enzyme (EMBO J, 1998, 13:3534-41). MIF has been found to be a critical mediator of septic shock. The corticotrophic cells of the anterior pituitary contain large stores of pre-formed MIF in secretory granules, which are released into the circulation by stress or infectious stimuli such as LPS. Injection of MIF potentiates LPS-induced death in animals, and the administration of anti-MIF antibodies fully protects animals from lethal endotoxemia. MIF is also the first protein to be identified that is secreted directly from immune cells upon glucocorticoid stimulation. Once released, MIF overrides the anti-inflammatory effects of steroids and thus appears to act physiologically as a unique, glucocorticoid-induced counter-regulatory hormone. Neutralization of MIF in animal models of additional inflammatory diseases such as arthritis, glomerulonephritis, and acute lung injury has pronounced therapeutic effects. (Curr Opin Pharmacol. 2001 December; 1(6):662-8.)

MIF regulates TLR-4 expression, the signal-transducing molecule of the LPS-receptor complex, by modulating transcription factor PU.1. This has been demonstrated by studying mouse macrophage cell lines transfected with anti-sense MIF messenger RNA. Thereby, MIF enhances the production of inflammatory cytokines such as TNF-α, and facilitates the initiation of host defense response (Nature 2001, 414:920). Experiments with MIF knock-out mice show that these mice are resistant to high doses of LPS but still retain their ability to clear bacteria indicating MIF to be an interesting target for treatment of sepsis (J. Exp. Med. 1999, 189:341-46). Anti-MIF antibody protected TNFα knockout mice from developing lethal peritonitis induced by cecal ligation and puncture, providing evidence of an intrinsic contribution of MIF to pathogenesis of sepsis (Nat. Med. 2000, 6:164-70). MIF has been shown to be elevated in sepsis. In a study with sepsis patients, severe sepsis patients demonstrated four to five times higher median MIF levels than in healthy controls (Intensive Care Med., 2001, 27:1412-5). In another study, high MIF levels were closely linked with poor outcome in patients with systemic inflammatory response syndrome (SIRS) (Intensive Care Med, 2001, 27:1187-93). In agreement with these reports we found MIF levels consistently higher in the sepsis patients at all time-points as compared to healthy controls.

IL-18: IL18 is an important pro-inflammatory cytokine that belongs to the IL-1 superfamily. It is a 24 kDa, non-glycosylated polypeptide with a structure similar to IL-1. IL-18 is synthesized as a bio-inactive propeptide that undergoes proteolytic cleavage by either ICE (interleukin-1 beta converting enzyme) or another caspase to generate a mature, bioactive, 18 kDa molecule (J. Immunol. 1996, 156:4274). IL-18 is an important regulator of IFN-γ production by immune cells. One of the most important consequences of IFN-γ secretion is the activation of macrophages. This is achieved through the induction of reactive oxygen intermediates and nitrogen monoxide (NO), which activate a variety of anti-bacterial, anti-tumor and anti-viral responses (Adv. Immunol., 1996, 62:61) In addition, IFN-γ contributes to endothelial cell activation, Th1 cell development, and upregulation of MHC expression on both professional APCs and non-APCs. This makes the regulation of IFN-gamma an extremely important step in the overall scheme of an inflammatory response (J. Immunol., 1996, 157:1350). Another important function of IL18 is the regulation of functionally distinct subsets of T-helper cells required for cell-mediated immune responses (Ann. Rev. Immunolo. 19: 423-74 2001).

A number of reports have shown elevated levels of IL-18 in sepsis patients. In a study to predict adverse outcome in post-operative sepsis, levels of IL-12 and IL-18 were evaluated. IL-18 levels were significantly increased during the course of lethal sepsis. Logistic regression analysis of IL-18 values measured on days 1 or 2 of sepsis revealed high serum values, suggesting that IL-18 represents an early predictive factor for adverse outcome of sepsis (Shock, 2002, 18:301-5). In another similar study IL-18 levels correlated significantly with APACHE II scores and other proinflammatory cytokines in sepsis patients, suggesting that levels of IL-18 are a good reflection of severity of disease (J. Med., 2000, 31:15-20). Our results are in good agreement with the literature indicating that IL-18 is indeed a good candidate biomarker for sepsis.

Overview of LIF:

Leukemia inhibitory factor (LIP), originally characterized by its ability to induce differentiation in myeloid cells of a murine leukemia cell line, has many biological actions which parallel those of IL-1, IL-6 and tumor necrosis factor-alpha. LIF is a pleiotropic cytokine expressed by multiple tissue types. The LIF receptor shares a common gp130 receptor subunit with the IL-6 cytokine superfamily. LIF signaling is mediated mainly by JAK-STAT (janus-kinase-signal transducer and activator of transcription) pathways and is abrogated by the SOCS (suppressor-of cytokine signaling) and PIAS (protein inhibitors of activated STAT) proteins. In addition to classic hematopoietic and neuronal actions, LIF plays a critical role in several endocrine functions including the utero-placental unit, the hypothalamo-pituitary-adrenal axis, bone cell metabolism, energy homeostasis, and hormonally responsive tumors. Local and systemic LIF serve to integrate multiple developmental and functional cell signals, culminating in maintaining appropriate hormonal and metabolic homeostasis. LIF thus functions as a critical molecular interface between the neuroimmune and endocrine systems.

Soluble LIF Ra has been shown to inhibit the binding of LIF to its cellular receptor, suggesting that its function may be to attenuate unwanted systemic effects of LIF.

LIF and Sepsis:

LIF levels are elevated in sepsis and correlate with shock and poor prognosis. Lipopolysaccharide (LPS) administration induces hypothalamic and pituitary LIF expression in vivo, which is associated with the acute rise in circulating adrenocorticotrophic hormone (ACTH) levels (Endocrine. 1997 December; 7(3):325-30.).

Circulating leukemia inhibitory factor levels correlate with disease severity in meningococcemia. LIF participates in the host response to infection, and it may contribute to the pathogenesis of septic shock. (J Infect Dis. 1994 November; 170 (5):1224-8.).

Passive immunization of mice against LIF (D factor) blocks lethality and cytokine release during endotoxemia. (J Exp Med. 1993 Sep. 1; 178(3): 1085-90.).

During day 1 of septic shock, peak plasma levels of G-CSF, interleukin (IL)-6, and leukemia inhibitory factor (LIF), but not GM-CSF, were greater than in sepsis or shock alone ($p<0.001$), and were correlated among themselves (rs=0.44-0.77; $p<0.02$) and with the APACHE II score (rs=0.25-0.40; p=0.03 to 0.18). Plasma levels of G-CSF, IL-6, and LIF are greatly elevated in critical illness, including septic shock, and are correlated with one another and with the severity of illness (Crit. Care Med. 2000 July; 28(7):2344-54.). Patients with rapid onset of septic shock demonstrated very high but transient tumor necrosis factor, interleukin (IL)-6, IL-8, and leukemia inhibitory factor concentrations (Crit. Care Med. 1997 March; 25(3):405-12.).

LIF, a pleiotropic cytokine with many biologic effects overlapping with those of IL-6, has been implicated in the pathogenesis of sepsis. LIF levels increased 2 h after *E. coli* challenge, and reached maximum values at 4 and 8 h after a sublethal (4.4+/−1.6 ng/ml) or lethal (40.9+/−3.8 ng/ml) dose, respectively. Circulating LIF correlated with plasma levels of IL-6, both after *E. coli* challenge (Spearman Rank coefficient of correlation (r)=0.849, p<0.001), as well as upon TNF-alpha injection (r=0.863, p<0.001). TNF-alpha is an intermediate factor in concerted release of LIF and IL-6 in vivo, and indicate that the enhanced elaboration of these cytokines may predict disease outcome in severe sepsis. (J. Immunol. 1996 Jun. 1; 156(11):4401-7.).

LIF protects against experimental lethal *Escherichia coli* septic shock in mice. This protective effect resembled endotoxin tolerance and was characterized by suppression of *E. coli*-induced serum tumor necrosis factor concentration (P<0.05), reduction in the number of viable bacteria (P<0.05), and prevention of Sepsis-induced tissue injury. Systemic LIF production is part of the host response to both endotoxin and sepsis-induced tissue injury. (Proc Natl Acad Sci USA. 1995 Feb. 28; 92(5):1337-41.)

Leukemia inhibitory factor levels are elevated in septic shock and various inflammatory body fluids. Serum LIF concentrations were transiently elevated (2-200 ng/ml) in six subjects with meningococcal or Gram-negative septic shock. Moderately elevated LIF concentrations (>10 ng/ml) were detected in cerebrospinal fluid from subjects with bacterial meningitis, in effusions associated with pneumonia and peritonitis, and in amniotic fluid from a woman with chorioamnionitis. (J Clin Invest. 1992 November; 90(5):2031-7.).

EXAMPLE 6

Biomarker Discovery

The major goals of this longitudinal study were to confirm and extend the findings of reported in the prior longitudinal study (Examples 2 and 4) in a second patient cohort and to perform a first examination for candidate biomarkers for death in sepsis.

Candidate Markers for Sepsis

Identification of sepsis biomarkers was performed using the same criteria defined in Examples 2 and 4, by identifying analyte profiles that revealed differences between the sepsis patient group and a group of normal controls at pre-infusion. The candidate sepsis biomarker profile of interest should show a marked difference in analyte level between 12 sepsis patients and 8 normal controls during acute sepsis prior to therapy (time zero). Analysis of variance (ANOVA) was used to identify significant differences between normal and sepsis patients at pre-infusion using GLM procedure of SAS. Because this analysis is limited by sample size, caution is required in interpreting p-values. With a small number of patients, there is increased potential for underestimation of p-values.

Only analytes that fulfilled the following criteria were evaluated as possible sepsis markers: (1) at least one of the group means (either sepsis group or normal controls) should be greater than 10 when MFI is expressed in log 2 scale (>1024 MFI in the linear scale), (2) there should be at least a two-fold difference between the group means, and (3) the p-value for the difference should less than 0.05. The first two criteria served as filters to ensure that (1) the data were within a fluorescent intensity range where meaningful measurements could be made, and (2) the differences were large enough so that differences due to random events in the small sample set were likely to be excluded.

63 out of 133 analytes (35 of 133 serum analytes and 48 of 133 plasma analytes) showed greater than 2-fold changes in intensity between sepsis patients and normal controls. 25% (20/83) of analytes exhibited greater than 2-fold difference in both serum and plasma matrices. Half of those (9/18) that exhibited more than a 5-fold difference in either plasma or serum also showed at least a 2-fold difference in the other matrix. Most notable among the latter were IL-6 and ST-2, because of large differences in both serum and plasma. However, several analytes exhibiting largest differences did so in only one matrix [leptin (serum only), MIP-3α, (plasma only), IL-2sRα, (serum only), IGFBP-1 (plasma only) and IL-18 (plasma only)]. IGFBP-1 is notable because in the sepsis survivors IGFBP-1 levels fell over time, whereas in the cohort that died, levels remained high. Thus, plasma IGFBP-1 level may be useful both in diagnosis of sepsis and prediction of sepsis death, albeit group sizes in the present study were very small. Discordance between serum and plasma underscores the benefit of measurements in both matrices for identification of biomarkers for sepsis.

The largest change was a 26-fold higher level of IL-6 in sepsis patients. CRP, an important acute response marker, was artifactually lower in sepsis patients than normal controls due to saturating levels of analyte in the undiluted sample. This saturation artifact was reduced upon dilution of the sample.

10 of 11 candidate sepsis biomarkers identified in the prior longitudinal study were concordant with the results obtained in this study. With the exception of AgRP, the other 10 cytokines that were previously identified as potential sepsis biomarkers also demonstrated significant differences in between sepsis patients and normal controls in Study 2. They were CD141, IL-18, IL-2sRα, IL-6, IL-8 [plasma], MIF [plasma], MMP-8 [plasma], MMP-7, MPIF (plasma) and IGFBP-1 (plasma) (Table 3). A number of other analytes including ST2 (25 fold), FGF-21 (9.5 fold), Leptin (9 fold), MCP-1 (8 fold), MIP-3β and TNF-R1 (7 fold) showed greater than >5 fold difference between sepsis patients and normal controls in this study alone. This study may have been more sensitive for identification of sepsis biomarkers than the prior study because there were more patients in this study, and sepsis was, on average, more severe, in the patients in this study.

TABLE 3

Concordance of Study 2 sepsis biomarkers with Study 1

| Analyte Name | Matrix | Study1 | Study2 |
|---|---|---|---|
| AgRP | Serum | ↑ | — |
| CD141 | Serum | ↑ | ↑ |
| CD141 | Plasma | — | ↑ |
| IL-18 | Serum | ↑ | ↑ |
| IL-18 | Plasma | — | ↑ |
| IL-2 sRα | Serum | ↑ | ↑ |
| IL-2 sRα | Plasma | ↑ | ↑ |
| IL-6 | Serum | ↑ | ↑ |
| IL-6 | Plasma | ↑ | ↑ |
| IL-8 | Serum | ↑ | — |
| IL-8 | Plasma | ↑ | ↑ |
| MIF | Plasma | ↑ | ↑ |
| MMP-8 | Plasma | ↑ | ↑ |
| MPIF-1 | Serum | ↑ | — |
| MPIF-1 | Plasma | ↑ | ↑ |
| IGFBP-1 | Serum | ↑ | — |
| IGFBP-1 | Plasma | ↑ | ↑ |
| MMP-7 | Serum | ↑ | ↑ |
| MMP-7 | Plasma | ↑ | ↑ |

Legend:
'—' no difference;
'↑' elevated in sepsis patients,
'↓' decreased in sepsis patients When sepsis samples were compared to normal serum at the pre-infusion time-point, there were significant differences in the levels of several analytes (e.g., IL-6, ST2, FGF-21, IL2sRα, MCP-1, MIP-3β, TNF-R1, Leptin, MMP-7, and MMP-8). Some of the observed changes in their levels were supported by the literature. IL-6, IL-2sRα and MMP-7 had previously been identified as candidate sepsis biomarkers in our prior study. These analytes are briefly discussed below.

IL-6 (Interleukin-6)

It is known that levels of IL-6 are increased in sepsis. In the present study, IL-6 was found to be elevated in sepsis samples at study enrollment (compared to normal controls), and to gradually decrease with time, approaching normal levels at day 7. IL-6 is an important pro-inflammatory cytokine that contributes to organ dysfunction in sepsis (Scand J Immunol 1998 48:509-14; Res Commun Chem Pathol Pharmacol 1994 84:291-300). Levels of IL-6 have also been shown to be associated with severity and mortality in sepsis (Eur J Haematol 1993 50:243-9; Nippon Geka Gakkai Zasshi 1996 97:1054-9). Therefore the high initial levels and reduction with time, observed in the present study, is in agreement with the literature.

ST2 (Suppression of Tumorigenicity 2; Interleukin 1 Receptor 4)

ST2/ST2L, a member of the IL-1R gene family, is expressed by fibroblasts, mast cells, and Th2 cells (J. Immunol. 2001; 166:6633-9). It exists in both membrane-bound (ST2L) and soluble forms (ST2). Although ST2/ST2L has immunoregulatory properties, its ligand, cellular targets, and mode of action are unknown. In the present study, ST2 was elevated in sepsis patients. This is a novel finding. It has been reported that ST2 binds to primary bone marrow-derived macrophages (BMM) and that this binding was enhanced by treatment with LPS (J. Immunol. 2001; 166:6633-9). ST2 treatment of BMMs inhibited production of the LPS-induced proinflammatory cytokines IL-6, IL-12, and TNF-alpha but did not alter IL-10 or NO production. Treatment of BMMs with ST2 down-regulated expression of Toll-like receptors-4 and -1 but induced nuclear translocation of NF-kappaB. Administration of ST2 in vivo after LPS challenge significantly reduced LPS-mediated mortality and serum levels of IL-6, IL-12, and TNF-alpha (J. Immunol. 2001; 166:6633-9). Conversely, blockade of endogenous ST2 through administration of anti-ST2 Ab exacerbated the toxic effects of LPS. Thus, ST2 has anti-inflammatory properties in sepsis by acting directly on macrophages. Increased levels of ST2 in sepsis patients observed in this study may represent a protective mechanism against the effects of LPS-induced proinflammatory cytokines. ST2 may represent a candidate for sepsis therapy.

FGF-21 (Fibroblast Growth Factor-21)

Little is known about FGF-21. It is most similar (approximately 35% amino acid identity) to FGF-19 and has a hydrophobic amino terminus (approximately 30 amino acids), with a typical signal sequence. FGF-21 mRNA was most abundantly expressed in the liver, and also in the thymus at lower levels. In the present study, FGF-21 was found to be elevated in sepsis patients. No literature reports describing a direct link between FGF-21 and sepsis were identified.

IL-2sRα (Interleukin 2 Soluble Receptor Alpha)

The biological activity of IL-2 is mediated by binding to a high affinity receptor complex composed of IL-2 Rα, β, and γ. By itself, IL-2 Rα binds IL-2 with low affinity, but is unable to transduce a signal. A soluble form of IL-2 Rα appears in serum, concomitant with its increased expression on cells (Immunol Today 1993 14:264-70, FASEB J 1991 5:2567-74, Hybridoma 1985 4:91-102). The function of IL-2 Rα is unclear, since it would be expected to be a poor inhibitor of IL-2 because of its low binding affinity. In any case, increased levels of soluble IL-2 Rα in biological fluids reportedly correlate with increased T cell, B cell and immune system activation.

Elevated level of sIL-2R has been observed in sepsis patients in multiple studies (Br J Surg 2000 87:223-30, Intensive Care Med 1999 25:1402-6, J Infect Dis 1991 163:1145-8). An increase of soluble IL-2 receptor level was also observed in patients with systemic inflammatory response syndrome (Thromb Res 1999 95:205-13). Furthermore, the level of sIL-2 receptor was found to be higher in non-surviving patients with septic shock than in surviving patients (J Infect 1998 37:241-7, Ann Clin Lab Sci 1996 26:426-32). The concentration of sIL-2R was found to have predictive value for identifying patients with gram-negative sepsis at risk for progression toward the syndrome of septic shock (J Crit. Care 1995 10:64-71). High concentrations of IL-6, IL-8 and sIL-2R predict organ failure in patients with community-acquired septic shock, and the combination of these markers may provide the means to identify sepsis patients who will develop organ failure (Clin Sci 1999 97:529-38). Furthermore, a study suggests that soluble interleukin-2 receptor levels can be used to facilitate the diagnosis of sepsis in premature infants where sepsis diagnosis is difficult because newborn infants often suffer from bacterial and viral infections without presenting typical symptoms (J Pediatr 1995 126:982-5). Therefore literature reports corroborate the increase of sIL-2R levels observed in the present study.

MCP-1 (Monocyte Chemoattractant Protein-1)

MCP-1 belongs to a superfamily of chemokines that have a leading role in the early chemotaxic events during inflammation (J Comp Neurol. 2001 434:461-77). In the present study, MCP-1 was found to be elevated in sepsis patients. This was a novel finding. It has been shown that MCP-1 protects mice in lethal endotoxemia (J Clin Invest. 1997 99:2832-6). Intraperitoneal administration of LPS to CD-1 mice induced a substantial increase in MCP-1 in plasma, lung, and liver. Immunization of mice with rabbit antimurine MCP-1 antiserum 2 h before endotoxin administration resulted in an increase in LPS-induced mortality from 10% to 65% and was associated with increases in TNF-alpha and IL-12 levels (J Clin Invest. 1997 99:2832-6). Conversely, the administration of recombinant murine MCP-1 intraperitoneally protected mice from endotoxin-induced death, and resulted in an increase in IL-10 levels and a decrease in IL-12 levels (J Clin Invest. 1997 99:2832-6). These findings suggest that MCP-1 has protective effects in murine endotoxemia. Similarly, it has been demonstrated that endogenous MCP-1 protects mice in a model of acute septic peritonitis (J. Immunol. 1999 163: 6148-54). MCP-1 appears to influence the cytokine balance in tissues in favor of anti-inflammatory and immune-enhancing cytokines, probably protecting the host from tissue/organ damage during sepsis (Exp Mol. Pathol. 2000 68:77-84). Human peritoneum rapidly reacts to abdominal surgery with increased production of MCP-1 (Shock. 2000 14:91-4). The increased levels of MCP-1 in sepsis patients, observed in this study, may represent a protective mechanism against the effects of sepsis.

MIP-3β (Macrophage-inflammatory Protein-3 Beta)

MIP-3β is a member of the CC-chemokine family. In the present study, MIP-3β was found to be elevated in sepsis patients. MIP-3β is expressed in bone marrow after induction with inflammatory cytokines and LPS, and may play a role in trafficking of macrophage progenitors in and out of the bone marrow in inflammatory conditions (J. Immunol. 1998 161: 2580-5). Addition of human MIP-3β beta to cultures of human PBMCs that have been activated with LPS resulted in a significant enhancement of IL-10 production (J. Immunol. 1999 163:4715-20). This effect was concentration-dependent. MIP-3β addition also inhibited IL-12 p40 and TNF-alpha production by monocytes and IFN-gamma production by T cells, possibly via IL-10 induction (J. Immunol. 1999 163:4715-20). These MIP-3β effects may represent a protective mechanism in sepsis. The increased levels of MIP-3β in sepsis patients, observed in the present study, is a novel finding.

TNF-R1 (Tumor Necrosis Factor Receptor 1)

TNF-α is a major mediator of apoptosis, inflammation and immunity, and it has been implicated in the pathogenesis of a wide spectrum of human diseases, including sepsis. TNF-alpha exerts its biologic effects through two distinct cell surface receptors, TNF-R1 and TNF-R2. The extracellular domain of TNF-alpha receptors inhibits TNF-α effects (Immunology. 1992 76:20-3). In the present study, TNF-R1 was found to be elevated in sepsis patients. Both soluble TNF receptor proteins (sTNF-R1 and sTNF-R2) have been described to influence the post-traumatic inflammatory response and organ dysfunction (Acta Anaesthesiol Scand. 2001 45:364-70). TNF alpha and soluble TNF receptor levels were elevated in trauma patients compared to healthy persons. Severe trauma led to enhanced sTNF-R1 levels on scene and on hospital admission. Development of systemic inflammatory response syndrome (SIRS) along with elevated sTNF-R1 began on scene and was present on admission. In trauma patients, early post-traumatic multiple organ dysfunction syndrome (MODS) and SIRS coincided with increased levels of TNF alpha and TNF receptor proteins, revealing different, time-dependent changes (Acta Anaesthesiol Scand. 2001 45:364-70). Transgenic mice expressing high levels of soluble TNF-R1 fusion protein are protected from lethal septic shock (Eur J. Immunol. 1995 25:2401-7). In children with severe meningococcaemia, the levels of sTNF-RI, -RII and TNF-alpha were markedly increased and all three correlated with the disease outcome. At admission, in patients with fatal outcome, the ratios TNF-alpha/sTNF-RI and -RII were higher than in survivors (Immunology. 1992 76:20-3). The increased levels of TNF-R1 in sepsis patients may represent a protective mechanism against the effects of proinflammatory cytokines.

Leptin

Leptin, an adipocyte-derived signaling factor, is a member of the IL-6 cytokine family. In addition to regulating food intake and energy expenditure, leptin also plays an important role in hematopoiesis. Leptin increases the proliferation of hematopoietic stem cell populations, and the proliferative effects seem to be at the level of a multilineage progenitor, as shown by increased myelopoiesis, erythropoiesis and lymphopoiesis (Curr Biol 1996 6:1170-80).

Both leptin and IL-6 are hypersecreted in acute critical illness such as sepsis. Leptin inhibits, whereas IL-6 stimulates, the hypothalamic-pituitary-adrenal axis (Horm Metab Res 1998 30:726-9). Patients with sepsis or septic shock were found to have leptin concentrations 2.3- and 4.2-fold greater, respectively, than a control group (J Infect Dis 1999 180:908-11). In a study looking at the serum leptin levels in 55 children with severe sepsis, the increase in leptin levels was higher in non-survivor patients than in survivors (Acta Paediatr 2002 91:626-31).

In the present study, leptin was found to be elevated in sepsis patients, which is in agreement with literature.

Matrix Metalloproteinase-8 (MMP-8)

Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. Matrix metalloproteinases are usually not expressed constitutively, and their expression is regulated by a variety of physiologic and pharmacologic signals, including cytokines and growth factors, bacterial endotoxin, phorbol esters, phagocytosable material, and hormones. Additionally, the activity of MMPs is regulated post-translationally through the activation of the proenzymes and the inhibition of active enzymes by endogenous inhibitors, α2-microglobulins and tissue inhibitors of metalloproteinases. Neutrophils secrete a considerable amount of MMPs, including neutrophil procollagenase (MMP-8). It has been hypothesized that MMP-8 may contribute to sepsis through the degradation of endothelial basement membranes, resulting in vascular leakage and shock (Acad Geneeskd Belg 2001; 63(6):531-8). Furthermore, in rats MMP inhibitors have been shown to specifically suppress TNF-α secretion following LPS stimulation (Shock, 1997, 7:427) suggesting a possible role of MMP's in inflammatory response.

Matrix Metalloproteinase-7 (MMP-7)

MMP-7 activity is upregulated in liver metastases of colorectal cancer (Clin Cancer Res 2002 8:144-8). Studies in mice suggest that MMP-7 regulates the activity of defensins in intestinal mucosa. Defensins represent an important component of host response to infection. No literature reports describing a direct association between MMP-7 levels and sepsis were found in the literature.

Candidate Biomarkers for Mortality in Sepsis

The profile of interest for candidate mortality markers in sepsis was a difference in analyte levels between the placebo survivors (3 patients) and placebo non-survivors (3 patients) that occurred in the days immediately preceding death. The time-period between day 0 and day 4 is of the greatest interest in this analysis, because this was the period during which most sepsis patients died. It is also important to qualify this analysis by recognizing that 3 patients per group is insufficient for the true significance of differential expression to be calculated. Given these caveats, ANOVA was used to estimate the ratio of specific to random effects, and to generate a list of analytes ranked by effect size that exhibit significant differences between the placebo survivors and placebo non-survivors. As previously described, only cytokines that fulfilled the following criteria were evaluated: (1) at least one of the group means (either sepsis group or normal controls) should be greater than 10 when MFI is expressed in log 2 scale (>1024 MFI in the linear scale) and (2) there should be at least a two-fold difference between the group means.

16 of 133 serum analytes and 3 of 133 plasma analytes exhibited a greater than 2-fold death difference in the day(s) immediately preceding death (Table 4). Analytes showing greatest difference prior to death (>3 fold change) in the analysis performed with the non-normalized data: Follistatin (15 fold), Gro-γ (11.46 fold), MIG (9.5 fold), BDNF (5.8 fold), Neutrophil elastase (3.5 fold), IL-18 (3.47) and MIP-3β (3.2 fold).

TABLE 4

Candidate biomarkers for mortality in sepsis from non-normalized data: Analytes exhibiting >2 fold differences between placebo survivors (3 patients) and placebo non-survivors (3 patients).

| Array | Cytokine | Matrix | Dilution | Time-point | Alive | Dead | Fold | F | MS | p-value |
|---|---|---|---|---|---|---|---|---|---|---|
| Array4 | Follistatin | SERUM | Neat | 3.00 | 8.40 | 12.31 | 15.02 | 1692.70 | 11.46 | <0.01 |
| Array4 | GRO-g | SERUM | Neat | 2.00 | 12.71 | 9.19 | 11.46 | 28.78 | 9.28 | 0.03 |
| Array2 | MIG | SERUM | Neat | 0.00 | 10.60 | 13.90 | 9.85 | 4.77 | 16.34 | 0.09 |
| Array2 | BDNF | SERUM | Neat | 2.00 | 13.47 | 10.92 | 5.85 | 32.87 | 9.74 | <0.01 |
| Array5 | Neut Elast | SERUM | Diluted | 0.00 | 13.44 | 15.28 | 3.58 | 6.68 | 5.81 | 0.05 |
| Array5 | IL-18 | SERUM | Neat | 0.00 | 11.87 | 13.66 | 3.47 | 6.74 | 4.82 | 0.06 |
| Array3 | MIP3β | SERUM | Neat | 3.00 | 11.41 | 9.72 | 3.24 | 194.39 | 3.45 | <0.01 |
| Array4 | Follistatin | SERUM | Neat | 0.00 | 9.69 | 11.21 | 2.87 | 167.84 | 3.47 | <0.01 |
| Array2 | Flt3Lig | SERUM | Neat | 3.00 | 11.71 | 10.22 | 2.81 | 7.34 | 2.66 | 0.07 |
| Array4 | Follistatin | SERUM | Neat | 1.00 | 8.91 | 10.26 | 2.54 | 12.47 | 1.35 | 0.07 |
| Array5 | IGFBP-6 | SERUM | Diluted | 3.00 | 12.89 | 14.13 | 2.35 | 39.92 | 1.83 | 0.01 |
| Array2 | HCC4 | SERUM | Neat | 0.00 | 14.01 | 15.21 | 2.31 | 26.91 | 2.19 | 0.01 |
| Array5 | ProteinS | SERUM | Diluted | 0.00 | 13.46 | 14.39 | 1.91 | 5.49 | 1.48 | 0.07 |
| Array5 | D-Dimer DD6 | PLASMA | Neat | 0.00 | 12.73 | 11.81 | 1.89 | 21.08 | 1.26 | 0.01 |
| Array2 | HCC4 | PLASMA | 0.00 | 0.00 | 14.47 | 15.38 | 1.88 | 13.28 | 1.24 | 0.02 |
| Array2 | MIP-1b | SERUM | 0.00 | 2.00 | 10.73 | 9.83 | 1.87 | 5.03 | 1.22 | 0.09 |
| Array5 | MIF | PLASMA | 1.00 | 0.00 | 9.66 | 10.51 | 1.80 | 5.78 | 1.08 | 0.07 |
| Array2 | SCF | SERUM | 0.00 | 0.00 | 9.74 | 10.58 | 1.79 | 6.53 | 1.07 | 0.06 |
| Array5 | ProteinC | SERUM | 0.00 | 1.00 | 12.01 | 12.85 | 1.79 | 6.32 | 1.05 | 0.07 |

See datafile 'AnovaLSMEANSEventByTherapyS2abs.xls'.

Some of the analytes in Table 4 are likely to show significant differences because of differences at the pre-infusion time-point. The data was therefore adjusted for baseline levels and ANOVA was performed on normalized data from serum samples. Plasma samples were not analyzed since samples from day 1, 2 and 3 samples were not available. Results are shown in Table 5.

TABLE 5

Candidate biomarkers for mortality in sepsis from normalized data: Analytes exhibiting >1.6 fold differences between placebo survivors (3 patients) and non-survivors (3 patient).

| Array | Cytokine | Dilution | Time-point | Therapy | Alive | Dead | Diff | Fold | MS | F | p-value |
|---|---|---|---|---|---|---|---|---|---|---|---|
| Array5 | Neut Elast | Diluted | 3.00 | PLACEBO | 0.50 | -2.64 | 3.14 | 8.81 | 11.82 | 7.60 | 0.07 |
| Array5 | MMP-8 | Diluted | 3.00 | PLACEBO | 0.38 | -2.56 | 2.93 | 7.65 | 10.33 | 5.59 | 0.10 |
| Array4 | Follistatin | Neat | 3.00 | PLACEBO | -1.29 | 1.14 | 2.43 | 5.40 | 4.44 | 202.59 | <0.01 |
| Array2 | Flt3Lig | Neat | 3.00 | PLACEBO | 0.81 | -1.15 | 1.96 | 3.88 | 4.60 | 17.59 | 0.02 |
| Array2 | BDNF | Neat | 2.00 | PLACEBO | -0.51 | -2.46 | 1.94 | 3.85 | 5.67 | 7.20 | 0.06 |
| Array4 | IL-1srII | Neat | 1.00 | PLACEBO | -1.18 | 0.32 | 1.50 | 2.82 | 1.68 | 161.83 | 0.01 |
| Array2 | MIG | Neat | 3.00 | PLACEBO | 0.27 | -1.06 | 1.33 | 2.51 | 2.11 | 131.40 | <0.01 |
| Array2 | Flt3Lig | Neat | 2.00 | PLACEBO | 0.48 | -0.78 | 1.26 | 2.39 | 2.38 | 38.54 | <0.01 |
| Array4 | IL-10rb | Neat | 3.00 | PLACEBO | -1.19 | -0.09 | 1.10 | 2.14 | 0.90 | 17.00 | 0.05 |
| Array5 | CD40 | Diluted | 3.00 | PLACEBO | 0.32 | -0.53 | 0.85 | 1.80 | 0.87 | 11.40 | 0.04 |
| Array2 | PARC | Neat | 3.00 | PLACEBO | 0.40 | -0.39 | 0.79 | 1.73 | 0.75 | 6.61 | 0.08 |
| Array2 | PARC | Neat | 2.00 | PLACEBO | 0.30 | -0.43 | 0.73 | 1.66 | 0.80 | 7.61 | 0.05 |
| Array2 | Flt3Lig | Neat | 1.00 | PLACEBO | 0.18 | -0.55 | 0.73 | 1.66 | 0.80 | 39.86 | <0.01 |
| Array5 | ProteinC | Diluted | 2.00 | PLACEBO | 0.21 | -0.50 | 0.71 | 1.64 | 0.76 | 4.78 | 0.09 |
| Array5 | ProteinS | Neat | 3.00 | PLACEBO | -0.21 | -0.90 | 0.69 | 1.61 | 0.57 | 40.49 | 0.01 |
| Array5 | TSH | Neat | 2.00 | PLACEBO | -0.37 | 0.32 | 0.68 | 1.61 | 0.70 | 7.51 | 0.05 |

See datafile 'AnovaLSMEANSEventByTherapyS2ratio.xls'.

Several analytes showed significant differences between placebo survivors and non-survivors, including neutrophil elastase, MMP-8, follistatin, MIG and BDNF. Neutrophil elastase (9 fold, day 3), MMP-8 (8 fold, day 4) and Follistatin (8 fold, day 3) showed a >5 fold change between placebo survivors and placebo non-survivors. Interestingly, Protein C rate of intensity changes were reduced 1.6-fold in patients who died as compared to survivors, suggesting a correlation between Protein C levels and survival. A complete set of results and analysis variance of placebo survivors vs. placebo non-survivors are provided in the appended excel files: 'AnovaLSMEANSEventByTherapyS2abs.xls' for non-normalized data and 'AnovaLSMEANSEventByTherapyS2ratio.xls' for normalized data.

Neutrophil Elastase

Severe inflammatory responses after surgery, trauma, and infection result in multiple organ dysfunction. Activated neutrophils are thought to be important in the pathogenesis of these responses acting via secretion of neutrophil elastase (NE), the dominant serine proteinase secreted from activated neutrophils (Inflammation. 1994 18:337-47). Neutrophil elastase is stored in azurophil granules along with other serine proteinases. As a result of its capacity to efficiently degrade extracellular matrix, NE has been implicated in a variety of destructive diseases (Nat. Med. 1998 4:615-8). In the present study, NE was found to be specifically elevated in placebo-treated sepsis patients that did not survive. This is a novel finding.

It has been shown that a recombinant human Kunitz-type proteinase inhibitor (R-020) was effective in significantly improving survival after induction of lethal peritonitis in rats (Inflammation. 1994 18:337-47). It has been suggested that various serine proteinases are implicated in the pathogenesis of neutrophil-related multiple organ failure and that recombinant human Kunitz-type proteinase inhibitors might be effective in the treatment of organ dysfunction. Similarly, in a hamster model of acute lung inflammation, analysis of BAL fluid revealed that after LPS administration the total cell number and neutrophil number, albumin concentration, and elastase-like activity were significantly lower in animals injected with an inhibitor of neutrophil elastase (ONO-5046.Na) (Eur Respir J. 1995 8:1293-9). Histological examination of the lungs of the animals treated with LPS alone showed intra-alveolar haemorrhages and inflammatory cell infiltration after LPS administration, whereas the lungs of the ONO-5046.Na-treated animals were only sparsely infiltrated by inflammatory cells. On the other hand, it has been demonstrated that mice lacking neutrophil elastase reveal impaired host defense against Gram negative bacterial sepsis (Nat. Med. 1998 4:615-8). NE−/− mice are more susceptible than their normal littermates to sepsis and death following intraperitoneal infection with Gram negative (*Klebsiella pneumoniae* and *Escherichia coli*) but not Gram positive (*Staphylococcus aureus*) bacteria. Neutrophils migrated normally to sites of infection in the absence of NE, but NE was required for maximal intracellular killing of Gram negative bacteria by neutrophils. Therefore, the levels of NE need to be precisely regulated and deviations from the optimal range could lead to severe damage and death.

Follistatin

Follistatin (FS) is the specific binding protein of activin, a growth and differentiation factor of many cell types. In the present study, follistatin was found to be elevated in placebo-treated sepsis patients that did not survive. It has been shown that the serum concentration of follistatin is elevated in patients with septicemia, consistent with a potential role of follistatin in the systemic inflammatory response (Eur J. Endocrinol. 2003 148:559-64; Clin Endocrinol (Oxf). 1998 48:413-7). It has been demonstrated that activin A and follistatin are involved in the systemic inflammatory response (Mol Cell Endocrinol. 2001 180:155-62). Activin A is released early in the cascade of circulatory cytokines during systemic inflammatory episodes. Release of activin A into the circulation occurred in sheep within 1 hour of injection of lipopolysaccharide (Endocrinology. 2000 141:1905-8). This rapid peak in activin A preceded the release of the key inflammatory cytokines, TNF-alpha and IL-6. Follistatin release into the circulation occurred some 4 hours after the peak of activin A and continued out to 24 hours from lipopolysaccharide treatment. Although the exact role of follistatin in sepsis and its outcome has not yet been revealed, the involvement of FS in systemic inflammation has been demonstrated by the changes in follistatin levels.

MMP-8

When normalized data was evaluated, a rapid decline in MMP-8 levels was observed in sepsis patients who died (Table 5). MMP-8 has previously been discussed. The rapid decline of MMP-8 in sepsis non-survivors was an unexpected and novel finding.

MIG (Monokine Induced by Interferon Gamma)

MIG belongs to the family of chemotactic cytokines known as CXC-chemokines. The MIG receptor is CXCR3, a receptor also shared by two other chemokines, I-TAC and IP-10. The synthesis of MIG is specifically induced in macrophages and in other cells by IFN-gamma, but not by IFN-alpha or bacterial lipopolysaccharides. It is thought that MIG is involved in modulating the growth, motility, and activation state of cells participating in inflammatory reactions. MIG is a chemoattractant for stimulated but not resting T-cells, and is not active on neutrophils or monocytes. As is the case with MMP-8, MIG levels also decline rapidly in sepsis patients who died.

BDNF

Brain-derived neurotrophic factor (BDNF) is a neurotrophin involved in neuronal survival and plasticity that binds to high-affinity receptors named TrkB. In the present study, BDNF was found to be decreased in placebo-treated sepsis patients that did not survive. It has been shown that LPS enhanced the production/secretion of BDNF from microglia (J. Neurochem. 2002 80:697-705; J Neurosci Res. 2001 65:322-31). LPS stimulation caused a marked increase in BDNF mRNA expression (J Neurosci Res. 1997 50:1023-9). LPS also elevated the expression of BDNF in mouse splenocytes and B cells (J. Neuroimmunol. 2000 103:112-21). The increased BDNF levels following LPS stimulation indicate a potential involvement of BDNF in systemic inflammation.

Correlation of APACHE II Scores with Cytokine Levels at Pre-infusion Time-point

Identifying cytokines that appear to represent surrogates for APACHE II scores is of interest since greatest benefit of certain drug treatments is evident in a high APACHE II score population. In addition, APACHE II scores may be used to determine the severity of sepsis in a patient suspected of having sepsis at a given time. APACHE II scores are determined subjectively based upon a number of clinical signs and symptoms. APACHE II scores may vary somewhat when determined by different physicians. An objective test that both identifies sepsis in hospitalized patients and can substitute for APACHE II score as an approved indication may be beneficial in assisting physicians select patients for certain drug therapy or identify patients with sepsis who are deteriorating or improving. If pre-infusion time-point cytokine levels correlate well with APACHE II scores, these cytokines may be useful as replacements or supplements to APACHE II scores. With this in mind, linear correlation of cytokine levels at pre-infusion time-point and APACHE II scores was performed in a manner similar to analysis done for study 1. A good correlation in this small patient subset suggests that these cytokines may have value as surrogate markers for APACHE II scores. For a simple bivariate correlation, Rho squared is qualitatively equal to R2 in linear regression analysis. The Pearson coefficient of correlation is very sensitive to outliers and non-linear relationships between variables, so the quality of the data as regards both of these aspects needs to be considered. The results of the analysis are shown in Table 6. Several analytes including AFP, CTACK and Eot-3 correlated well with baseline APACHE II scores. With the exception of CTACK, analytes that correlated with APACHE II scores in study 1 did not exhibit high correlation with baseline APACHE II scores in Study 2.

Ten analytes (6 of the 133 serum analytes and 5 of the 133 plasma analytes) correlated with baseline APACHE II score at pre-infusion point with a correlation coefficient of >0.6. Complete results of the correlation analysis are appended.

TABLE 6

Correlation analysis of analyte levels and baseline APACHE II at pre-infusion time point (cytokines with correlation coefficient >0.6 are shown.

| Cytokine | Dilution | SAMPLE TYPE | rho |
|---|---|---|---|
| AFP | Neat | PLASMA | 0.739085 |
| AFP | Neat | SERUM | 0.682285 |
| CTACK | Neat | SERUM | 0.659666 |
| Eot-3 | Neat | SERUM | 0.617859 |
| FGF-basic | Neat | SERUM | 0.615801 |
| IGFBP-4 | Neat | SERUM | 0.679348 |
| IGFBP2 | Neat | PLASMA | 0.646765 |
| sgp130 | Neat | PLASMA | 0.659828 |
| sgp130 | Neat | SERUM | 0.664349 |
| AFP | Diluted | PLASMA | 0.779448 |
| AFP | Diluted | SERUM | 0.726881 |

TABLE 6-continued

Correlation analysis of analyte levels and baseline
APACHE II at pre-infusion time point (cytokines
with correlation coefficient >0.6 are shown.

| Cytokine | Dilution | SAMPLETYPE | rho |
|---|---|---|---|
| E-Selectin | Diluted | SERUM | 0.602813 |
| IL-18 | Diluted | PLASMA | 0.618898 |

EXAMPLE 7

A Larger Longitudinal Study

Serum samples for 127 patients were provided for this study. There were 58 survivors and 69 non-survivors. Samples were run at a 1:5 dilution on five arrays. In addition, the study included 57 samples taken from acutely ill patients in an Intensive Care Unit (ICU) with non-sepsis illnesses. All samples were serum. In studies 1 and 2 shown in Examples 2, 4, and 6, all samples were run undiluted on protein arrays. For the current study, all samples were diluted five-fold. The five-fold dilution resulted in somewhat decreased signals for all analytes and increased background on array 3.

All samples were diluted 1:5 and run a total of three times on each array, on consecutive days. Each of the different runs was treated as a separate, complete dataset for analysis. Analyses of variance were completed for each day, and the results were compared. Only analytes exhibiting differences between groups that fulfilled the following significance criteria were included in this report: (1) p value for the observed difference between groups should be less than 0.05 (2) there should be a significant change identified in at least two of the 3 replicates, (3) the change should be concordant ($log_2$ ratio either positive or negative) between replicates, and (4) the size of the observed difference should be greater than the variability observed in the blank control feature on the array, to eliminate false positives attributable to random variation.

Candidate Markers for Sepsis

Sepsis biomarkers in Study 3 were identified using criteria slightly different than those which were used in Longitudinal Studies 1 and 2. In the previous two sepsis studies, analyte levels in sepsis patients at pre-infusion were compared to analyte levels in healthy individuals to identify analytes elevated in sepsis. These studies identified markers that were not necessarily specific to sepsis since elevated expression levels may have represented acute phase reactants. In an effort to identify markers specific for sepsis, the present study contained comparisons between the sepsis patient group at pre-infusion and a group of equally ill patients that had been admitted to the intensive care unit with a variety of illnesses but who did not have sepsis. The use of sick controls was expected to yield markers with greater specificity for sepsis by controlling for differential expression in acute illness. The sepsis biomarker profile sought in the present study was a significant difference in analyte level between the sepsis patient group during acute sepsis prior to therapy (pre-infusion) and the sick control group. Analysis of variance (ANOVA) was used to identify significant differences between sick and sepsis patients using the GLM procedure of SAS. Differences between the two groups were not considered relevant if they showed less variability than the blank control feature on each array. Results are shown in Table 7.

29 of 83 analytes demonstrated significant differences in mean fluorescence intensity between the sepsis patient group at pre-infusion and sick controls (Table 7). 17 of the 29 had more than a two-fold difference in mean fluorescence intensity over all three assay repeats. IL-1Ra (16x) and IL-6 (12x) showed the greatest elevated levels of expression in sepsis patients as compared to sick controls. MCP-1 (5x), MPIF-1 (4x), IL-2sRa (3.5x) TNF-R1(3x), MIG (2.5x) and ST-2 (2.5x) were also substantially elevated in sepsis patients. Interestingly, other analytes showed decreased expression in the sepsis group as compared to sick controls. For instance, EGF levels were fourfold lower in the sepsis group, and ENA-78 and HCC4 were almost 3-fold lower.

TABLE 7

Study 3 biomarkers for sepsis on Arrays 1-3: 483 sepsis and 57 ill control samples
were run a total of three times on each array, on consecutive days (replicate).

| Analyte Name | Replicate | log2 ratio (Sepsis/Sick) Mean | Std Dev | Sepsis Mean log2 MFI | Std Dev | Sick Mean log2 MFI | Std Dev | p-value |
|---|---|---|---|---|---|---|---|---|
| BLC | run 1 | 0.63 | 1.17 | 7.32 | 1.26 | 6.69 | 0.62 | 0.00041 |
| | run 2 | 0.82 | 1.18 | 6.95 | 1.24 | 6.13 | 0.86 | 0.000004 |
| | run 3 | 0.65 | 1.2 | 7.7 | 1.27 | 7.05 | 0.84 | 0.000404 |
| EGF | run 1 | −2.2 | 1.3 | 7.89 | 1.34 | 10.09 | 1.1 | <.000001 |
| | run 2 | −2.27 | 1.31 | 7.4 | 1.23 | 9.67 | 1.63 | <.000001 |
| | run 3 | −2.31 | 1.24 | 8.13 | 1.27 | 10.44 | 1.1 | <.000001 |
| ENA-78 | run 1 | −1.35 | 1.67 | 9.36 | 1.74 | 10.7 | 1.36 | <.000001 |
| | run 2 | −1.87 | 1.59 | 8.81 | 1.64 | 10.68 | 1.35 | <.000001 |
| | run 3 | −1.63 | 1.66 | 9.29 | 1.75 | 10.92 | 1.24 | <.000001 |
| Eot | run 2 | −0.87 | 0.62 | 6.32 | 0.54 | 7.19 | 0.9 | <.000001 |
| | run 3 | −0.82 | 0.56 | 6.79 | 0.55 | 7.61 | 0.62 | <.000001 |
| GROb | run 2 | −0.57 | 1.1 | 8.38 | 1.17 | 8.95 | 0.76 | 0.000664 |
| | run 3 | −0.74 | 1.19 | 9.42 | 1.26 | 10.17 | 0.84 | 0.000202 |
| HCC4 | run 1 | −1.46 | 1.6 | 10.68 | 1.74 | 12.14 | 0.77 | <.000001 |
| | run 2 | −1.65 | 1.67 | 9.93 | 1.77 | 11.57 | 1.11 | <.000001 |
| | run 3 | −1.56 | 1.6 | 10.07 | 1.76 | 11.63 | 0.99 | <.000001 |
| HVEM | run 2 | 0.6 | 0.88 | 8.09 | 0.95 | 7.49 | 0.51 | 0.000009 |
| | run 3 | 0.36 | 0.84 | 8.19 | 0.87 | 7.83 | 0.69 | 0.007135 |
| IL-15 | run 2 | 0.51 | 0.72 | 6.15 | 0.72 | 5.63 | 0.7 | 0.000002 |
| | run 3 | 0.24 | 0.64 | 6.6 | 0.66 | 6.36 | 0.5 | 0.011704 |

TABLE 7-continued

Study 3 biomarkers for sepsis on Arrays 1-3: 483 sepsis and 57 ill control samples were run a total of three times on each array, on consecutive days (replicate).

| Analyte Name | Replicate | log2 ratio (Sepsis/Sick) | | Sepsis | | Sick | | p-value |
|---|---|---|---|---|---|---|---|---|
| | | Mean | Std Dev | Mean log2 MFI | Std Dev | Mean log2 MFI | Std Dev | |
| IL-1b | run 1 | −1.56 | 0.81 | 5.77 | 0.71 | 7.34 | 1.14 | <.000001 |
| | run 2 | −1.37 | 0.92 | 5.25 | 0.84 | 6.62 | 1.19 | <.000001 |
| | run 3 | −1.12 | 0.76 | 6.37 | 0.61 | 7.5 | 1.08 | <.000001 |
| IL-1ra | run 1 | 4.14 | 2.43 | 12.6 | 2.62 | 8.47 | 1.39 | <.000001 |
| | run 2 | 4.27 | 2.59 | 12.25 | 2.75 | 7.97 | 1.76 | <.000001 |
| | run 3 | 3.88 | 2.44 | 12.52 | 2.65 | 8.65 | 1.33 | <.000001 |
| IL-2sRa | run 1 | 1.9 | 1.21 | 13.49 | 1.2 | 11.59 | 1.26 | <.000001 |
| | run 2 | 1.84 | 1.35 | 13.32 | 1.36 | 11.49 | 1.29 | <.000001 |
| | run 3 | 1.75 | 1.26 | 13.62 | 1.26 | 11.87 | 1.24 | <.000001 |
| IL-6 | run 1 | 3.61 | 2.53 | 11.7 | 2.73 | 8.09 | 1.4 | <.000001 |
| | run 2 | 3.94 | 2.65 | 11.4 | 2.85 | 7.47 | 1.59 | <.000001 |
| | run 3 | 3.49 | 2.4 | 11.79 | 2.58 | 8.31 | 1.42 | <.000001 |
| IL-8 | run 1 | −0.84 | 1.64 | 11.33 | 1.68 | 12.17 | 1.47 | 0.00087 |
| | run 2 | −1.02 | 1.84 | 11.08 | 1.9 | 12.1 | 1.56 | 0.000222 |
| | run 3 | −0.89 | 1.8 | 11.55 | 1.88 | 12.44 | 1.44 | 0.001392 |
| Leptin | run 1 | −1.41 | 2.56 | 9.64 | 2.62 | 11.05 | 2.08 | 0.027099 |
| | run 2 | −1.06 | 2.27 | 8.63 | 2.37 | 9.69 | 1.81 | 0.001948 |
| | run 3 | −0.92 | 2.25 | 9.24 | 2.35 | 10.16 | 1.83 | 0.009683 |
| MCP-1 | run 1 | 2.14 | 1.57 | 12.43 | 1.69 | 10.29 | 0.84 | <.000001 |
| | run 2 | 1.97 | 1.78 | 11.75 | 1.95 | 9.78 | 0.73 | <.000001 |
| | run 3 | 2.87 | 1.64 | 11.86 | 1.83 | 9 | 0.9 | <.000001 |
| MCP-2 | run 1 | 1.01 | 1.68 | 8.18 | 1.82 | 7.16 | 0.9 | 0.00009 |
| | run 2 | 1 | 1.6 | 7.31 | 1.73 | 6.31 | 0.9 | 0.000033 |
| | run 3 | 0.67 | 1.62 | 8.06 | 1.74 | 7.4 | 0.91 | 0.007912 |
| M-CSF | run 1 | 0.36 | 0.83 | 10.37 | 0.87 | 10.01 | 0.66 | 0.00439 |
| | run 2 | 0.29 | 0.87 | 10.09 | 0.91 | 9.79 | 0.66 | 0.024124 |
| MIG | run 1 | 1.44 | 2.24 | 10.6 | 2.39 | 9.16 | 1.41 | 0.000023 |
| | run 2 | 1.39 | 2.27 | 10.47 | 2.41 | 9.08 | 1.56 | 0.000054 |
| | run 3 | 1.91 | 2.2 | 11.12 | 2.36 | 9.2 | 1.64 | <0.000001 |
| MIP-1a | run 1 | −0.44 | 0.64 | 7.68 | 0.61 | 8.12 | 0.73 | 0.000009 |
| | run 2 | −0.58 | 0.63 | 7.11 | 0.59 | 7.68 | 0.77 | <0.000001 |
| | run 3 | −0.41 | 0.58 | 7.34 | 0.59 | 7.75 | 0.54 | 0.000005 |
| MIP3b | run 1 | 1.34 | 0.97 | 8.47 | 1.06 | 7.13 | 0.49 | <.000001 |
| | run 2 | 1.09 | 1.03 | 8 | 1.11 | 6.91 | 0.58 | <.000001 |
| | run 3 | 1.03 | 1.03 | 8.27 | 1.1 | 7.25 | 0.62 | <.000001 |
| MMP9 | run 1 | 1.18 | 1.07 | 11.72 | 1.07 | 10.54 | 1.1 | <.000001 |
| | run 2 | 1.06 | 1.07 | 11.59 | 1.07 | 10.53 | 1.03 | <.000001 |
| | run 3 | 0.86 | 1.01 | 11.62 | 0.97 | 10.76 | 1.16 | <.000001 |
| MPIF-1 | run 1 | 2.12 | 1.28 | 9.72 | 1.37 | 7.6 | 0.78 | <.000001 |
| | run 2 | 2.17 | 1.32 | 9.18 | 1.4 | 7.02 | 0.9 | <.000001 |
| | run 3 | 1.96 | 1.25 | 9.62 | 1.33 | 7.66 | 0.87 | <.000001 |
| OSM | run 1 | −0.66 | 0.64 | 7.8 | 0.65 | 8.46 | 0.63 | <.000001 |
| | run 2 | −0.56 | 0.66 | 7.41 | 0.57 | 7.98 | 0.95 | <.000001 |
| PARC | run 1 | 1.1 | 0.97 | 12.62 | 0.98 | 11.52 | 0.92 | <.000001 |
| | run 2 | 0.78 | 0.97 | 12.84 | 0.97 | 12.06 | 0.94 | <.000001 |
| | run 3 | 0.87 | 1.01 | 11.93 | 1.06 | 11.06 | 0.86 | <.000001 |
| ST2 | run 1 | 1.75 | 1.24 | 8.6 | 1.34 | 6.85 | 0.67 | <.000001 |
| | run 2 | 1.43 | 1.25 | 8 | 1.36 | 6.57 | 0.59 | <.000001 |
| | run 3 | 1.49 | 1.32 | 8.37 | 1.44 | 6.88 | 0.59 | <.000001 |
| TNF-R1 | run 1 | 1.79 | 1.02 | 12.46 | 1.07 | 10.68 | 0.79 | <.000001 |
| | run 2 | 1.68 | 1.18 | 12.36 | 1.2 | 10.68 | 1.07 | <.000001 |
| | run 3 | 1.47 | 1.26 | 11.23 | 1.27 | 9.76 | 1.26 | <.000001 |

Mean log2 fluorescence intensity values for sepsis patients and sick patients are shown. The difference between the sepsis and sick group values were calculated (log2 ratio (sepsis/sick)), with the accompanying p-value for the difference. Each of the different runs was treated as a separate, complete dataset. Identical analyses were completed for each day, and the results are shown for each analysis. Only analytes that fulfilled the following criteria were included: (1) p value for the difference less than 0.05 (2) a significant change observed in at least two of the replicates, (3) the change should be concordant ($log_2$ ratio either positive or negative) between days, and (4) the size of the observed difference should be greater than the variability of the blank control feature on the array, to eliminate false positives attributable to random variation.

Several analytes (P-Selectin, Protein C and MIF) from array 5 demonstrated excellent correlation and low variability when comparing replicates, so little or no change is expected for these analytes in the final curated dataset. Data was base 2 log transformed for all calculations.

P-Selectin, Protein C and MIF all show significant (p-value<$10^{-6}$) differences between ICU control and Sepsis patients. Expression levels of analytes were more than 1.4 fold lower in sepsis (Table 8).

TABLE 8

P-Selectin, Protein C and MIF are all decreased in sepsis as compared to sick controls.

| Analyte | Replicate | Log ratio (sepsis/sick) Mean | Std Dev | Sepsis Mean | Std Dev | Sick Mean | Std Dev | p-value |
|---|---|---|---|---|---|---|---|---|
| MIF | 1.00 | −1.5 | 1.26 | 9.56 | 1.31 | 11.06 | 1.05 | <.000001 |
|  | 2.00 | −1.52 | 1.24 | 9.3 | 1.3 | 10.82 | 0.96 | <.000001 |
| P-Selectin | 1.00 | −0.8 | 0.93 | 12.27 | 0.97 | 13.06 | 0.75 | <.000001 |
|  | 2.00 | −0.8 | 0.99 | 12.12 | 1.04 | 12.92 | 0.74 | <.000001 |
| ProteinC | 1.00 | −0.42 | 0.47 | 13.09 | 0.5 | 13.51 | 0.28 | <.000001 |
|  | 2.00 | −0.49 | 0.4 | 12.81 | 0.43 | 13.29 | 0.26 | <.000001 |

There were at least 4 major differences between Study 3 and the previous studies that might have been anticipated to impact sepsis biomarker findings. First, studies 1 and 2 were very small, with only 6 and 12 sepsis patients, respectively, whereas the current study contained 240 sepsis patients. Utilization of a greater number of patients may be expected to increase the power of the study to identify sepsis markers. Second, in Study 3 the average APACHE II score was above 25, indicating that patients in Study 3 had more severe sepsis than in studies 1 and 2, where APACHE scores for some of the patients were relatively low. The third difference was that sepsis markers were identified in Study 1 and Study 2 in comparisons between healthy controls and sepsis patients. In Study 3, comparisons were made between ill, non-septic (ICU admitted) patients and sepsis patients. Fourth, Studies 1 and 2 used plasma and serum samples whereas Study 3 used 1:5 diluted serum only. A comparison of the three studies (Table 9) showed that many sepsis markers such as IL-6, IL-2sRa, and MPIF-1 were common to all three studies, while others (MMP-7) fell away.

TABLE 9

Concordance of Study 3 sepsis serum biomarkers with Study 1 and 2.

| Analyte Name | Study1 | Study2 | Study3Prelim |
|---|---|---|---|
| AgRP | ↑ | — | N/A |
| CD141 | ↑ | ↑ | N/A |
| IL-18 | ↑ | ↑ | N/A |
| IL-2 sRα | ↑ | ↑ | ↑ |
| IL-6 | ↑ | ↑ | ↑ |
| IL-8 | ↑ | — | ↓ |
| MPIF-1 | ↑ | — | ↑ |
| IGFBP-1 | ↑ | — | N/A |
| MMP-7 | ↑ | ↑ | — |

Sepsis biomarkers were found in serum in Study 1 and 2 by comparing sepsis and healthy patients at pre-infusion. Study 3 compared sepsis patients with individuals admitted to the ICU for non-sepsis related injuries or illnesses. Analytes highlighted in gray are elevated in sepsis above levels seen for both normal and sick individuals. Data have not yet been obtained for analytes marked N/A, these will be discussed in the final report.
Legend:
'—' no difference;
'↑' elevated in sepsis patients,
'↓' decreased in sepsis patients Several additional sepsis markers were identified in Study 3 (Table 10), in addition to the markers shown above.

TABLE 10

Sepsis specific markers identified for the first time in Study 3

| Analyte Name | Level in Sepsis |
|---|---|
| BLC | ↑ |
| EGF | ↓ |

TABLE 10-continued

Sepsis specific markers identified for the first time in Study 3

| Analyte Name | Level in Sepsis |
|---|---|
| ENA-78 | ↓ |
| EOT | ↓ |
| Gro-beta | ↓ |
| HCC4 | ↓ |
| HVEM | ↑ |
| IL-15 | ↑ |
| IL-1b | ↓ |
| IL-1ra | ↑ |
| IL-8 | ↓ |
| Leptin | ↓ |
| MCP-1 | ↑ |
| MCP-2 | ↑ |
| M-CSF | ↑ |
| MIG | ↑ |
| MIF | ↓ |
| MIP-1a | ↑ |
| MIP-3b | ↑ |
| MMP-9 | ↑ |
| OSM | ↓ |
| PARC | ↑ |
| Protein C | ↓ |
| P-selectin | ↓ |
| ST-2 | ↑ |
| TNF-R1 | ↑ |

Sepsis markers were identified in study 3 by comparing analyte levels in sepsis patients with levels in individuals admitted to the ICU for non-sepsis related injuries or illnesses. This comparison screens out markers that are common to multiple diagnoses and focuses on markers that are specific to sepsis. Analytes with a 2.5-fold or greater difference are highlighted in gray.
Legend:
'—' no difference;
'↑' elevated in sepsis patients,
'↓' decreased in sepsis patients compared to ICU admitted sick controls.

Candidate Biomarkers for Mortality in Sepsis

Biomarkers for sepsis mortality in Study 3 were identified using the following criteria:

In order to avoid the influence of drug treatment, only placebo-treated patients were considered.

Samples in this study were taken either at preinfusion (visit 1) or 24 hours after infusion of placebo (visit 2). As a result, predictive mortality biomarkers could be identified using samples taken at both time points, so both were included in the analysis.

In an effort to identify biomarkers specific for mortality associated with sepsis and not other conditions, only analytes that were already identified as biomarkers for sepsis in the sepsis/sick analysis above were considered as potential biomarkers for sepsis mortality.

P-value for a given candidate biomarker should be <0.05 when sepsis survivor patients were compared to sepsis non-survivors.

Differences between the two groups were not considered meaningful if they showed less variability than the blank control feature on each array.

Analysis of variance (ANOVA) was used to identify significant differences between survivors and non-survivors at pre-infusion and day 1 using the GLM procedure of SAS. Results of the analysis are shown in Table 11.

19 out of 83 analytes demonstrated significant differences in mean fluorescence intensity between the sepsis survivors and non-survivors (Tables 11 and 12). 6 of the 19 had more than a two-fold difference in mean fluorescence intensity in at least one visit: IL-1Ra, IL-6, IL-8, MCP-1, MCP-2, and MIG. All of these analytes showed increased expression in the sepsis non-survivors as compared to sepsis survivors.

TABLE 11

Study 3 biomarkers for sepsis mortality on Arrays 1-3: Comparisons were made between survivors and nonsurvivors for samples taken at visit 1 (preinfusion) or visit 2 (24 hours after infusion).

| Analyte Name | Visit | Replicate | Alive at Day 28 | | Dead at Day 28 | | log2 ratio (Alive/Dead) | | p-value |
|---|---|---|---|---|---|---|---|---|---|
| | | | Mean log2 MFI | Std Dev | Mean log2 MFI | Std Dev | Mean | Std Dev | |
| BLC | visit1 | run1 | 7.06 | 0.99 | 7.63 | 1.39 | −0.57 | 1.21 | 0.0043 |
| | | run2 | 6.74 | 1.03 | 7.21 | 1.32 | −0.47 | 1.19 | 0.0079 |
| | | run3 | 7.33 | 1.08 | 8.06 | 1.34 | −0.73 | 1.23 | 0.0009 |
| | visit2 | run1 | 7.06 | 1.1 | 7.51 | 1.34 | −0.45 | 1.23 | 0.0125 |
| | | run2 | 6.66 | 1.11 | 7.13 | 1.22 | −0.47 | 1.17 | 0.0051 |
| | | run3 | 7.29 | 1.11 | 7.84 | 1.31 | −0.55 | 1.23 | 0.0103 |
| EGF | visit1 | run1 | 8.08 | 1.39 | 7.51 | 1.1 | 0.57 | 1.25 | 0.0089 |
| | | run2 | 7.53 | 1.17 | 7.13 | 1.12 | 0.4 | 1.14 | 0.0479 |
| | | run3 | 8.28 | 1.48 | 7.82 | 1.07 | 0.46 | 1.28 | 0.0333 |
| Eot2 | visit1 | run1 | 11.06 | 1.02 | 10.55 | 1.08 | 0.51 | 1.05 | 0.0013 |
| | | run2 | 10.76 | 0.95 | 10.26 | 1.12 | 0.5 | 1.04 | 0.0042 |
| | | run3 | 11.02 | 1.02 | 10.54 | 1.13 | 0.49 | 1.08 | 0.0041 |
| | visit2 | run1 | 11.04 | 1.2 | 10.63 | 0.98 | 0.41 | 1.09 | 0.0128 |
| | | run2 | 10.72 | 1.05 | 10.26 | 1.11 | 0.46 | 1.08 | 0.0268 |
| | | run3 | 10.99 | 1.11 | 10.51 | 1.15 | 0.48 | 1.13 | 0.0142 |
| HCC4 | visit1 | run1 | 11.06 | 1.54 | 10.65 | 1.71 | 0.42 | 1.63 | 0.014 |
| | | run2 | 10.34 | 1.64 | 10.01 | 1.69 | 0.34 | 1.67 | 0.0482 |
| | | run3 | 10.73 | 1.59 | 10 | 1.84 | 0.73 | 1.75 | 0.0495 |
| | visit2 | run1 | 11.79 | 1.2 | 11.06 | 1.72 | 0.73 | 1.5 | 0.0011 |
| | | run2 | 10.96 | 1.71 | 10.36 | 1.63 | 0.61 | 1.66 | 0.0158 |
| | | run3 | 11.64 | 1.3 | 10.07 | 1.83 | 1.57 | 1.65 | 0.0001 |
| HVEM | visit2 | run1 | 8.33 | 0.74 | 8.61 | 0.82 | −0.28 | 0.78 | 0.0464 |
| | | run2 | 7.83 | 0.92 | 8.4 | 1.01 | −0.56 | 0.97 | 0.0016 |
| | | run3 | 7.93 | 0.78 | 8.46 | 0.9 | −0.53 | 0.85 | 0.0012 |
| IL-1b | visit2 | run1 | 5.6 | 0.52 | 5.93 | 0.57 | −0.33 | 0.55 | 0.0003 |
| | | run2 | 4.87 | 0.7 | 5.51 | 0.88 | −0.64 | 0.8 | 9E−06 |
| | | run3 | 6.24 | 0.52 | 6.45 | 0.55 | −0.21 | 0.54 | 0.0327 |
| IL-1ra | visit1 | run1 | 11.93 | 2.79 | 13.33 | 2.16 | −1.4 | 2.48 | 0.0003 |
| | | run2 | 11.6 | 2.93 | 12.93 | 2.37 | −1.33 | 2.64 | 0.0006 |
| | | run3 | 11.84 | 2.89 | 13.29 | 2.31 | −1.45 | 2.59 | 0.0003 |
| | visit2 | run1 | 9.4 | 2.46 | 11.56 | 2.62 | −2.17 | 2.55 | 2E−06 |
| | | run2 | 9.08 | 2.71 | 11.11 | 2.6 | −2.03 | 2.65 | 5E−06 |
| | | run3 | 9.57 | 2.38 | 11.53 | 2.62 | −1.96 | 2.52 | 1E−05 |
| IL-2sRa | visit1 | run2 | 13.16 | 1.38 | 13.53 | 1.33 | −0.37 | 1.35 | 0.0197 |
| | | run3 | 13.53 | 1.33 | 13.8 | 1.21 | −0.27 | 1.27 | 0.0473 |
| | visit2 | run1 | 13.18 | 1.16 | 13.46 | 1.44 | −0.29 | 1.32 | 0.0482 |
| | | run2 | 12.9 | 1.44 | 13.55 | 1.26 | −0.65 | 1.35 | 0.0004 |
| | | run3 | 13.28 | 1.29 | 13.83 | 1.09 | −0.56 | 1.18 | 0.0006 |
| IL-6 | visit1 | run1 | 11.02 | 2.83 | 12.14 | 2.46 | −1.13 | 2.65 | 0.0043 |
| | | run2 | 10.64 | 3.08 | 12.05 | 2.44 | −1.41 | 2.75 | 0.0006 |
| | | run3 | 11.08 | 2.86 | 12.45 | 2.25 | −1.37 | 2.55 | 0.0006 |
| | visit2 | run1 | 9.1 | 2.11 | 11.03 | 2.32 | −1.93 | 2.23 | 2E−06 |
| | | run2 | 8.68 | 2.24 | 10.59 | 2.52 | −1.91 | 2.4 | 3E−06 |
| | | run3 | 9.25 | 1.95 | 11.04 | 2.43 | −1.79 | 2.23 | 3E−05 |
| IL-8 | visit1 | run1 | 10.94 | 1.4 | 11.63 | 1.66 | −0.7 | 1.54 | 0.0038 |
| | | run2 | 10.6 | 1.67 | 11.44 | 1.91 | −0.84 | 1.8 | 0.0019 |
| | | run3 | 10.84 | 1.81 | 12.02 | 1.77 | −1.18 | 1.79 | 1E−04 |
| | visit2 | run1 | 10.06 | 0.8 | 10.89 | 1.66 | −0.83 | 1.34 | 0.0002 |
| | | run2 | 9.71 | 1.16 | 10.77 | 1.59 | −1.06 | 1.41 | 4E−06 |
| | | run3 | 10.06 | 0.67 | 11.19 | 1.68 | −1.13 | 1.33 | 5E−06 |
| MCP-1 | visit1 | run1 | 12.07 | 1.6 | 12.73 | 1.76 | −0.66 | 1.68 | 0.0164 |
| | | run2 | 11.15 | 1.92 | 12.23 | 1.99 | −1.08 | 1.96 | 0.0004 |
| | visit2 | run1 | 11.25 | 1.26 | 12.39 | 1.61 | −1.13 | 1.46 | 3E−05 |
| | | run2 | 10.31 | 1.3 | 11.67 | 1.75 | −1.35 | 1.56 | 1E−06 |
| | | run3 | 10.69 | 1.52 | 11.68 | 1.74 | −0.99 | 1.66 | 0.0025 |
| MCP-2 | visit1 | run1 | 7.51 | 1.38 | 8.64 | 2.03 | −1.13 | 1.76 | 0.0002 |
| | | run2 | 6.83 | 1.23 | 7.73 | 1.89 | −0.9 | 1.61 | 0.0004 |
| | | run3 | 7.28 | 1.08 | 8.68 | 1.87 | −1.4 | 1.55 | <.000001 |

TABLE 11-continued

Study 3 biomarkers for sepsis mortality on Arrays 1-3: Comparisons were made between survivors and nonsurvivors for samples taken at visit 1 (preinfusion) or visit 2 (24 hours after infusion).

| Analyte Name | Visit | Replicate | Alive at Day 28 Mean log2 MFI | Std Dev | Dead at Day 28 Mean log2 MFI | Std Dev | log2 ratio (Alive/Dead) Mean | Std Dev | p-value |
|---|---|---|---|---|---|---|---|---|---|
| | visit2 | run1 | 7.09 | 1.06 | 8.26 | 1.73 | −1.17 | 1.46 | 5E−06 |
| | | run2 | 6.44 | 0.98 | 7.23 | 1.4 | −0.8 | 1.23 | 5E−05 |
| | | run3 | 6.95 | 1 | 8.15 | 1.68 | −1.2 | 1.41 | 3E−06 |
| M-CSF | visit1 | run1 | 10.14 | 0.68 | 10.43 | 0.96 | −0.29 | 0.84 | 0.032 |
| | | run2 | 9.79 | 0.76 | 10.28 | 1.02 | −0.5 | 0.91 | 0.0013 |
| MIG | visit1 | run1 | 10.08 | 2.11 | 11.04 | 2.31 | −0.96 | 2.22 | 0.0069 |
| | | run2 | 9.86 | 2.04 | 10.93 | 2.41 | −1.07 | 2.25 | 0.0027 |
| | visit2 | run1 | 9.36 | 1.79 | 10.72 | 2.21 | −1.36 | 2.02 | 9E−05 |
| | | run2 | 8.88 | 1.86 | 10.65 | 2.34 | −1.77 | 2.13 | 4E−06 |
| | | run3 | 10.15 | 1.81 | 11.01 | 2.29 | −0.86 | 2.11 | 0.049 |
| MIP3b | visit2 | run1 | 8.06 | 0.85 | 8.45 | 1.03 | −0.38 | 0.94 | 0.0222 |
| | | run2 | 7.52 | 0.95 | 7.87 | 1.05 | −0.35 | 1 | 0.0189 |
| | | run3 | 7.67 | 0.94 | 8.25 | 1.03 | −0.58 | 0.99 | 0.0005 |
| ST2 | visit2 | run1 | 7.7 | 0.99 | 8.47 | 1.28 | −0.77 | 1.15 | 0.0002 |
| | | run2 | 7.06 | 0.83 | 7.67 | 1.15 | −0.61 | 1.01 | 0.0007 |
| | | run3 | 7.36 | 1.02 | 8.19 | 1.4 | −0.83 | 1.25 | 7E−05 |
| TNF-R1 | visit1 | run1 | 12.25 | 1.15 | 12.79 | 0.99 | −0.54 | 1.07 | 0.0097 |
| | | run2 | 12.13 | 1.33 | 12.74 | 1.15 | −0.61 | 1.24 | 0.0048 |
| | visit2 | run1 | 12 | 1.19 | 12.78 | 1.06 | −0.78 | 1.12 | 0.0003 |
| | | run2 | 11.87 | 1.35 | 12.8 | 1.22 | −0.93 | 1.28 | 9E−05 |

All samples were run a total of three times on each array, on consecutive days (replicate). Mean log2 fluorescence intensity values for placebo treated sepsis survivors and nonsurvivors are shown. The difference between the sepsis and sick values were calculated (log2 ratio (alive/dead)), with the accompanying p-value for the difference. Each of the different runs was treated as a separate, complete dataset. Identical analyses were completed for each day, and the results are shown for each analysis. Only analytes that fulfilled the following criteria were considered: (1) p value for the difference should be less than 0.05 (2) there should be a significant change identified for at least two of the days, (3) the change should be concordant (log2 ratio either positive or negative) between days, and (4) the size of the observed difference should be greater than the variability of the blank control feature on the array, to eliminate false positives attributable to random variation.

On the selected array 5 analyte data, significant (p-value<0.001) differences in MIF levels were found between survivors and non-survivors at visit1 and visit2. Expression levels of MIF were ~1.7 fold lower in survivors at baseline (Table 12). Expression levels of P-Selectin were decreased (p-value<0.04) by 1.2 fold in survivors (Table 12).

TABLE 12

Array 5 mortality biomarkers

| Analyte | THERAPY | Variable | Replicate | Alive at Day 28 Mean | Std Dev | Dead at Day 28 Mean | Std Dev | Diff (1-2) Mean | Std Dev | p-value |
|---|---|---|---|---|---|---|---|---|---|---|
| MIF | PLACEBO | visit1 | 1.00 | 9.2 | 1.01 | 9.96 | 1.26 | −0.75 | 1.15 | 0.000137 |
| | | | 2.00 | 8.94 | 1.07 | 9.6 | 1.2 | −0.66 | 1.14 | 0.000288 |
| | | visit2 | 1.00 | 8.98 | 1.14 | 9.76 | 1.57 | −0.78 | 1.39 | 0.001274 |
| | | | 2.00 | 8.77 | 1.06 | 9.57 | 1.46 | −0.81 | 1.29 | 0.000349 |
| P-Selectin | PLACEBO | Logratio | 1.00 | −0.29 | 0.61 | 0.01 | 0.93 | −0.3 | 0.8 | 0.036262 |
| | | | 2.00 | −0.28 | 0.66 | 0.07 | 0.96 | −0.35 | 0.83 | 0.019712 |

(p-value < 0.05)

As mentioned above, there were at least three major differences (number of patients, average APACHE scores and control populations) between Study 3 and the previous studies that were expected to impact mortality biomarker findings. Nevertheless, a comparison of Studies 2 and 3 (no mortality biomarkers could be identified in Study 1 due to experimental design) showed that some sepsis mortality markers such as MIG, MIP-3b, and HCC-4 were common to both studies (Table 13).

TABLE 13

Concordance of Study 3 sepsis mortality serum biomarkers with Study 2 (non-normalized data).

| Analyte Name | Study2 | Study3Prelim |
|---|---|---|
| BDNF | ↓ | — |
| Flt3Lig | ↓ | — |
| Follistatin | ↑ | N/A |
| Gro-g | ↓ | N/A |
| HCC-4 | ↑ | ↓ |
| IGFBP-6 | ↑ | N/A |

TABLE 13-continued

Concordance of Study 3 sepsis mortality serum
biomarkers with Study 2 (non-normalized data).

| Analyte Name | Study2 | Study3Prelim |
|---|---|---|
| IL-18 | ↑ | N/A |
| MIG | ↑ | ↑ |
| MIP-1b | ↓ | — |
| MIP-3b | ↓* | ↑* |
| Neutr. elastase | ↑ | N/A |
| Protein C | ↑ | — |
| Protein S | ↑ | N/A |
| SCF | ↑ | — |

Data have not yet been obtained for analytes marked N/A, these will be discussed in the final report.
Legend:
'—' no difference;
'↑' elevated in non-survivors,
'↓' decreased in non-survivors
*different time point Other sepsis markers were identified in Study 3 (Table 14), in addition to the markers shown above.

TABLE 14

Sepsis mortality markers identified only in Study 3.

| Analyte Name | Levels in non-survivors |
|---|---|
| BLC | ↑ |
| EGF | ↓ |
| Eot2 | ↓ |
| HVEM | ↑ |
| IL-1b | ↑ |
| IL-1ra | ↑ |
| IL-2sRa | ↑ |
| IL-6 | ↑ |
| IL-8 | ↑ |
| MCP-1 | ↑ |
| MCP-2 | ↑ |
| M-CSF | ↑ |
| MIF | ↑ |
| P-selectin | ↑ |
| ST-2 | ↑ |
| TNF-R1 | ↑ |

Legend:
'—' no difference;
'↑' elevated in non-survivors,
'↓' decreased in non-survivors Cytokines play an essential role in the coordination of the cellular and humoral responses in systemic inflammation. In the present study, three array 5 analytes, MIF, P-selectin and protein C, were found to be differentially expressed when sepsis patients and ICU controls were compared and are discussed in more detail here. MIF and P-selectin were identified also as potential biomarkers for mortality.

In the present study, macrophage migration inhibitory factor (MIF) was identified as a potential biomarker for sepsis and mortality. MIF has been shown to carry out important functions as a mediator of the immune system. Constitutively expressed by a broad spectrum of cells and tissues, including monocytes and macrophages, MIF is rapidly released after exposure to microbial products and pro-inflammatory mediators, and in response to stress. After it is released, MIF induces pro-inflammatory biological responses that act as a regulator of immune responses. MIF activates the extracellular signal-regulated kinase 1 (ERK1)/ERK2-mitogen-activated protein kinase pathway, inhibits the activity of JUN activation domain-binding protein 1 (JAB1), upregulates the expression of Toll-like receptor 4 to promote the recognition of endotoxin-expressing bacterial pathogens, sustains pro-inflammatory function by inhibiting p53-dependent apoptosis of macrophages and counter-regulates the immunosuppressive effects of glucocorticoids on immune cells (Nature Reviews Immunology 2003 3, 791-800). As a pro-inflammatory mediator, MIF has been shown to be implicated in the pathogenesis of severe sepsis and septic shock, acute respiratory distress syndrome, and several other inflammatory and autoimmune diseases, including rheumatoid arthritis, glomerulonephritis and inflammatory bowel diseases. MIF has been shown to be a critical mediator of septic shock. High concentrations of MIF were detected in the peritoneal exudate fluid and in the systemic circulation of mice with bacterial peritonitis (Nat. Med. 2000 6:164-70). Anti-MIF antibody protected TNF-α knockout mice from lethal peritonitis induced by cecal ligation and puncture (CLP), providing evidence of an intrinsic contribution of MIF to the pathogenesis of sepsis. Anti-MIF antibody also protected normal mice from lethal peritonitis induced by both CLP and E. coli, even when treatment was started up to 8 h after CLP. Conversely, co-injection of recombinant MIF and E. coli markedly increased the lethality of peritonitis. Finally, high concentrations of MIF were detected in the plasma of patients with severe sepsis or septic shock (Nat. Med. 2000 6:164-70). These studies define a critical part for MIF in the pathogenesis of septic shock and identify a new target for therapeutic intervention. Furthermore, it has been shown that activated protein C (APC) inhibits MIF and TNF production in monocytes (Eur Cytokine Netw. 2000 11:407-13). Inhibition of MIF release by APC was found to be independent of TNF, as stimulation of MIF release by LPS was unaltered in the presence of anti-TNF antibodies. These results suggest that the anti-inflammatory properties of APC are mediated via inhibition of the release of the pro-inflammatory cytokines MIF and TNF. Given its crucial role as a regulator of sepsis, pharmacological or immunological modulation of MIF activity might offer new treatment opportunities for the management of systemic inflammation.

Another analyte that was identified as a potential biomarker for sepsis was protein C(PC). In the coagulation cascade, PC is activated by the thrombin-thrombomodulin-complex and inactivates factors V a and VIM. Additionally, activated protein C has a profibrinolytic effect. The relevance of protein C to the pathogenesis of sepsis is well known.

P-selectin was identified in the present study as a potential biomarker for sepsis and mortality. P-selectin is a protein found in the alpha-granules of platelets and the Weibel-Palade bodies of endothelial cells. On cell activation it is expressed on the cell surface and also secreted into plasma (Thromb Haemost. 1997 77:1081-5). P-selectin in the plasma membrane surface is exposed and serves as a cell adhesion receptor to interact with other cell receptors, including PSGL-1 and GPM (Thromb Haemost. 2001 86:214-21). P-selectin upregulates tissue factor in monocytes and leads to leukocyte accumulation in areas of vascular injury associated with thrombosis and inflammation. High levels of soluble P-selectin were found in patients with sepsis (398+/−203 ng/mL) compared to healthy controls (122+/−38 ng/mL). Similarly, the concentration of P-selectin per platelet was higher in patients with sepsis (4.8+/−4.3 fg/platelet) than in the control group (0.6+/−0.2 fg/platelet) (Thromb Haemost. 1997 77:1081-5). P-selectin expression was increased in various organs within the peritoneum of mice exposed to polymicrobial sepsis (Am J Physiol Gastrointest Liver Physiol. 2001 280:G291-7). The plasma concentrations of soluble P-selectin, platelet factor-4 (PF-4) and beta-thromboglobulin (betaTG) in patients with septic shock were significantly higher than those in healthy control subjects (p<0.001), suggesting that these mediators could be associated with septic shock (Inflamm Res. 1999 48:171-5). Interestingly, in whole blood APC was found to inhibit recombinant tissue factor-induced platelet activation, measured by the amount of P-selectin (Thromb Res. 1997 87:197-204). The anticoagulant effect of APC is believed to be based mainly on the inhibition of thrombin generation. This is also supported by in vitro studies using human plasma in which APC, after activation by a thrombin-thrombomodulin complex (Thr+Tm) formed during coagulation via the extrinsic pathway, caused a delay in thrombin generation and a reduction of the maximum thrombin concentration (Thromb Haemost. 1993 70:423-6). The generation of APC by the thrombin-thrombomodulin complex is stimulated by platelet factor-4 (PF-4), which interacts with both the thrombomodulin's glycosaminoglycan and the protein C Gla domain to enhance markedly the affinity of the thrombin-thrombomodulin complex for protein C (J Biol. Chem. 1994 269:25549-56). By this mechanism, PF-4 may play an important role in the physiologic regulation of clotting. PF-4 is a novel analyte measured on the latest version of MSI array 4. Very preliminary analysis indicates that it also demonstrates differential expression in the present study.

EXAMPLE 8

Summary of Final Array 4 Dataset 480 sepsis and 57 ICU control patient samples were assayed in triplicate on MSI Array 4, which contains 37 analytes.

515 samples passed in triplicate, 21 samples passed in duplicate and 1 samples passed in singlicate (Table 15). More than 99% of samples passed in duplicate or triplicate, exceeding the 85% minimum acceptable pass rate, indicative of successful completion of Array 4 data generation.

TABLE 15

Statistics For Passed Replicates

| Passed replicates | Number of Samples | Percentage (%) |
|---|---|---|
| 0 | 0 | 0 |
| 1 | 1 | 0.19 |
| 2 | 21 | 3.91 |
| 3 | 515 | 95.9 |
| Total | 537 | 100 |

Data Processing and Experimental Set Up

Three replicates for each sample were run on 3 consecutive days on three different microarray lots. A four-point concentration titration curve ("anchor points", Type=CurveC in attached dataset) was run on every slide for normalization and quality control purposes. The four-point concentration titration curve comprised four wells on each slide that were interrogated with a standard buffer supplemented with 12, 37, 333 and 1000 pg/mL of each array 1 analyte. In addition, expanded 16- or 8-point concentration curves (full-titration, Type=CurveD) were run on up to 9 slides.

Individual sample values were normalized using linear regression of that slide's anchor points within a day to reduce slide to slide imprecision. Day-to-day imprecision was reduced using regression-based normalization of day-to-day averages of anchor points. Between-day variability (CV) was 32%, on average, for samples, 15% for the anchor points, and 28% for the full-titration wells, respectively (Table 16). These values are consistent with standard platform performance.

TABLE 16

Day-to-day Variability On A Linear Scale (CV in %)

| Sample Type | <CV> | N | Std Dev | Median CV |
|---|---|---|---|---|
| Sample | 32.18 | 19869 | 19.07 | 29.01 |
| Anchor Point | 15.55 | 152 | 12.01 | 11.01 |
| Full Titration | 28.55 | 608 | 14.87 | 26.78 |

Data File Descriptions

Slidemapname: the name of the array. The current data related to version 5 of array 4 (Proteomics 4.5).

AnalyteName: the name of the measured analyte. BLANK is a negative control feature.

MSIBarcode: sample barcode per MSI operation.

Run day: the consecutive day number in which the samples were run. For example, d1 is day 1.

MFI: mean fluorescence intensity, on a linear scale.

Client Sample_ID, PatientNumber, PatIni, ClientDescription have been provided by the client.

Note: Samples with ICUControl prefix in Client Sample_ID field represent non-sepsis, critically ill, hospitalized control patients provided by MSI.

DX: diagnosis (sepsis or sick for ICU controls).

Type: Source of data. Sample for Sepsis and ICU controls, CurveC for anchor points and CurveDB for titrations.

Conc: the concentration of analytes in pg/ml.

Summary of Final Array 5 Dataset 480 sepsis and 57 ICU control patient samples were assayed in triplicate on MSI Array 5, which contains 27 analytes.

507 samples passed in triplicate, 30 samples passed in duplicate (Table 17). One hundred percent of samples passed in duplicate or triplicate, exceeding the 85% minimum acceptable pass rate, indicative of successful completion of Array 5.

TABLE 17

Statistics For Passed Replicates

| Passed replicates | Number of Samples | Percentage (%) |
|---|---|---|
| 0 | 0 | 0 |
| 1 | 0 | 0 |
| 2 | 30 | 5.59 |
| 3 | 507 | 94.41 |
| Total | 537 | 100 |

Data Processing and Experimental Set Up

Three replicates for each sample were run on 3 consecutive days on three different microarray lots. A four-point concentration titration curve ("anchor points", Type=CurveC in attached dataset) was run on every slide for normalization and quality control purposes. The four-point concentration titration curve comprised four wells on each slide that were interrogated with a standard buffer supplemented with 12, 37, 333 and 1000 pg/mL of each array 1 analyte. In addition, expanded 16- or 8-point concentration curves (full-titration, Type=CurveD) were run on up to 9 slides.

Individual sample values were normalized using linear regression of that slide's anchor points within a day to reduce slide to slide imprecision. Day-to-day imprecision was reduced using regression-based normalization of day-to-day averages of anchor points. Between-day variability (CV) was 25%, on average, for samples, 11% for the anchor points, and 19% for the full-titration wells, respectively (Table 18). These values are consistent with standard platform performance.

TABLE 18

Day-to-day Variability On A Linear Scale (CV in %)

| Sample Type | <CV> | N | Std Dev | Median CV |
|---|---|---|---|---|
| Sample | 25.37 | 14909 | 15.62 | 22.69 |
| Anchor Point | 11.13 | 112 | 6.78 | 8.95 |
| Full Titration | 19.79 | 448 | 16.90 | 16.53 |

Data File Descriptions

Slidemapname: the name of the array. The current data related to version 3I of array 5 (Proteomics 5.3I).

AnalyteName: the name of the measured analyte. BLANK is a negative control feature.

MSIBarcode: sample barcode per MSI operation.

Run day: the consecutive day number in which the samples were run. For example, d1 is day 1.

MFI: mean fluorescence intensity, on a linear scale.

Client Sample_ID, PatientNumber, PatIni, ClientDescription have been provided by the client.

Note: Samples with ICUControl prefix in Client Sample_ID field represent non-sepsis, critically ill, hospitalized control patients provided by MSI.

DX: diagnosis (sepsis or sick for ICU controls).

Type: Source of data. Sample for Sepsis and ICU controls, CurveC for anchor points and CurveDB for titrations.

Conc: the concentration of analytes in pg/ml.

The invention claimed is:

1. A method of diagnosing sepsis in a human subject suspected of having sepsis, comprising:
   determining a concentration of at least one analyte in a fluid test sample from said human subject;
   comparing the concentration of each said analyte(s) to a corresponding reference concentration selected to indicate the presence or absence of sepsis, wherein said reference concentration is determined using one or more control samples obtained from one or more human subjects not suffering from sepsis, provided that at least one of said analyte(s) is myeloid progenitor inhibitory factor-1 ("MPIF-1"), wherein an elevation in concentration of said analyte(s) in the test sample of at least about two fold relative to the reference concentration is indicative of the presence of sepsis in the human; and
   diagnosing sepsis in the human subject using the result(s) of said comparing step.

2. The method of claim 1 wherein said samples comprise blood.

3. The method of claim 1 wherein said samples comprise serum.

4. The method of claim 1 wherein said samples comprise plasma.

5. The method of claim 1 wherein further provided that at least one analyte is interleukin 1 receptor antagonist ("IL-1 Ra").

6. The method of claim 1 wherein further provided that at least one analyte is monocyte chemotactic protein-1 ("MCP-1").

7. The method of claim 1 wherein further provided that at least one analyte is tumor necrosis factor receptor-1 ("TNF-R1").

8. The method of claim 1 wherein sepsis is diagnosed if the concentrations of at least two of said analytes in said test sample are elevated at least about two fold relative to the corresponding reference concentrations.

9. The method of claim 1 wherein an elevation in concentration of MPIF-1 in the test sample of at least about four fold relative to the reference concentration is indicative of the presence of sepsis in said human.

* * * * *